(12) United States Patent
Caroon et al.

(10) Patent No.: US 6,319,920 B1
(45) Date of Patent: Nov. 20, 2001

(54) 2-ARYLETHYL-(PIPERIDIN-4-YLMETHYL) AMINE DERIVATIVES

(75) Inventors: Joan Marie Caroon, Mountain View; Robin Douglas Clark, Palo Alto; Michael Patrick Dillon, San Carlos; Ralph New Harris, III, Redwood City; Sharathchandra Surendra Hegde, Sunnyvale; Clara Jeou Jen Lin, Palo Alto; Hans Maag, Menlo Park; David Bruce Repke, Milpitas, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/241,816

(22) Filed: Feb. 1, 1999

Related U.S. Application Data
(60) Provisional application No. 60/076,113, filed on Feb. 27, 1998, and provisional application No. 60/109,097, filed on Nov. 19, 1998.

(51) Int. Cl.[7] ............... A61K 31/535; A61K 31/445; C07D 413/00; C07D 471/02; C07D 211/22
(52) U.S. Cl. ............... 514/235.5; 514/300; 514/318; 514/326; 514/329; 514/330; 514/331; 544/129; 546/123; 546/194; 546/199; 546/207; 546/212; 546/214; 546/221; 546/223; 546/224; 546/225; 546/229; 546/232; 546/233
(58) Field of Search ................ 546/229, 225, 546/194, 199, 207, 214, 221, 212, 223, 224, 232, 233, 123; 544/129; 514/330, 235.5, 300, 318, 326, 329, 331

(56) References Cited

U.S. PATENT DOCUMENTS

| | | | |
|---|---|---|---|
| 5,089,507 | 2/1992 | Vecchietti et al. | 514/321 |
| 5,286,735 | 2/1994 | Bonnaud et al. | 514/321 |
| 5,310,743 | 5/1994 | Schilling et al. | 514/311 |
| 5,541,195 | 7/1996 | Schilling et al. | 514/311 |
| 5,646,144 | 7/1997 | Schilling et al. | 514/241 |

FOREIGN PATENT DOCUMENTS

| | | |
|---|---|---|
| 0 532 398 | 3/1993 | (EP) . |
| WO 97/10212 | 3/1997 | (WO) . |

OTHER PUBLICATIONS

Goodman & Gilman's, *The Pharmacological Basic of Therapeutics*, ninth edition, McGraw–Hill, New York, Chapter 7:148–160 (1996).

*Primary Examiner*—D. Margaret Seaman
*Assistant Examiner*—Raymond Covington
(74) *Attorney, Agent, or Firm*—Janet Kaku; Gloria Pfister

(57) ABSTRACT

This invention relates to muscarinic receptor antagonist compounds selected from the group of compounds represented by Formula I:

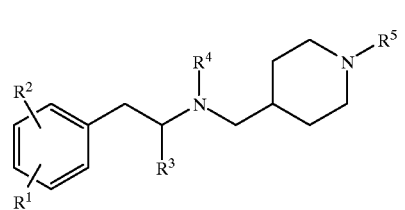

I wherein the substituents are as defined in the specification; and their pharmaceutically acceptable salts, individual isomers or a racemic or non-racemic mixture; pharmaceutical compositions containing them; and methods for their use as therapeutic agents.

35 Claims, No Drawings

2-ARYLETHYL-(PIPERIDIN-4-YLMETHYL) AMINE DERIVATIVES

CROSS REFERENCE TO RELATED APPLICATIONS

This application claims benefit under Title 35 U.S.C. 119(e) of U.S. Provisional Application Nos. 60/076,113, filed Feb. 27, 1998, and 60/109,097, filed Nov. 19, 1998; both applications are incorporated herein by reference.

BACKGROUND OF THE INVENTION

1. Field of the Invention

This invention relates to muscarinic receptor antagonists, especially certain 2-arylethyl-(piperidin-4-ylmethyl)amine derivatives, pharmaceutical compositions containing them, and methods for their use as therapeutic agents.

2. Background of the Invention

Muscarinic receptor antagonists prevent the effects of acetylcholine by blocking its binding to muscarinic cholinoceptors at neuroeffector sites on smooth muscle, cardiac muscle, and gland cells in peripheral ganglia and in the central nervous system, and predominantly have been employed to inhibit effects of parasympathetic nervous system activity. Thus, muscarinic receptor antagonists have far reaching physiological effects, and drugs which selectively interact with muscarinic receptors have an array of therapeutic applications. For example, muscarinic receptor antagonists have been employed in the treatment of various disorders in the gastrointestinal tract, genitourinary tract, respiratory tract, cardiovascular system, central nervous system, and have been shown to be useful in anesthesiology and ophthalmology.

Muscarinic receptor antagonists have been shown to be useful in treating various gastrointestinal disorders, including a wide variety of conditions that involve increased spasticity or motility of the gastrointestinal tract, for example diarrhea. These agents can reduce tone and motility if the conditions are due to excessive smooth muscle contractions.

Muscarinic receptor antagonists have been shown to be useful in treating various genitourinary tract disorders. These agents have been shown to lower intravesical pressure, increase bladder capacity, and reduce the frequency of urinary bladder contractions by antagonizing the parasymathetic control of this organ.

Muscarinic receptor antagonists have been shown to be useful in treating various respiratory tract disorders, particularly including those conditions that reduce secretion in both the upper and lower respiratory tracts and induce bronchial dilation. These agents can have beneficial effects when obstruction of the airway is associated with, for example, chronic bronchitis, chronic obstructive pulmonary disease, bronchial asthma or emphysema.

Muscarinic receptor antagonists have been shown to be useful in treating various cardiovascular disorders, for example, including those conditions where excessive vagal tone causes sinus or nodal bradycardia.

Muscarinic receptor antagonists have been shown to be useful in treating central nervous system disorders. These agents have been shown to be efficacious in previous dystonias or Parkinsonian symptoms, and have been highly effective in preventing motion sickness.

Muscarinic receptor antagonists have been shown to be useful in anesthesiology, particularly by inhibiting excessive salivation and secretions of the respiratory tract induced by administration of general anesthetic agents, and their concomitant bronchodilator action. They have also been shown to be useful in ophthalmology to produce mydriasis and cycloplegia when applied locally to the eye.

These and other therapeutic uses are described in *Goodman & Gillman's, The Pharmacological Basis of Therapeutics*, ninth edition, McGraw-Hill, New York, 1996; Chapter 7, pages 148–160.

DESCRIPTION OF THE RELATED ART

Certain piperidineamine compounds have been exemplified in the chemical patent literature. For example, U.S. Pat. Nos. 5,310,743; 5,541,195; and 5,646,144 (Schilling et al.) disclose 1-acyl-N-(2-chlorophenyl)ethyl-4-piperidineamine derivatives having substance P antagonistic properties. Other piperidine derivatives are described in U.S. Pat. No. 5,286,735 (Bonnaud and Bigg) useful as serotoninergic receptor ligands and for the treatment of anxiety or depression; U.S. Pat. No. 5,089,507 (Vecchietti et al.) for the treatment of pain or hyponatremic disease states; European Published Application No. EP 532 398 (assigned to Synthelabo) for treatment of psychoses, anxiety, hypertension and migraine; and PCT Published Application No. WO 97/10212 (assigned to Neurosearch A/S) for treatment of stroke, anoxia, ischemia, migraine, psychosis, epilepsy or other convulsive disorders.

The disclosures of these and other documents referred to throughout this application are incorporated herein by reference.

SUMMARY OF THE INVENTION

This invention provides compounds selected from the group of compounds represented by Formula I:

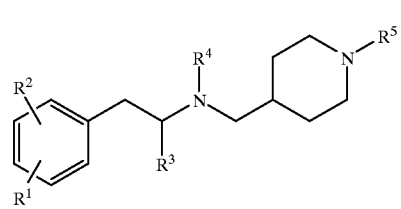

wherein
$R^1$ is independently in each occurrence: hydrogen, alkyl, alkyloxy, halogen, haloalkyl, or amino;
$R^2$ is independently in each occurrence:
(1) alkyl,
(2) alkyloxy,
(3) halogen,
(4) haloalkyl,
(5) nitro,
(6) heterocyclyl, unsubstituted or heterocyclyl optionally substituted with oxo,
(7) —O(CH$_2$)$_p$X wherein p is 0–6 and X is independently selected from haloalkyl or aryl,
(8) —NR$^7$R$^8$,
(9) —NR$^6$COR$^9$,
(10) —NR$^6$CONR$^7$R$^8$,
(11) —NR$^6$CSR$^9$,
(12) —NR$^6$CSNR$^7$R$^8$,
(13) —NR$^6$SO$_2$R$^9$,
(14) —NR$^6$SO$_2$NR$^7$R$^8$,
(15) —SR$^9$,
(16) —SOR$^9$,

(17) —SO$_2$R$^9$,
(18) —SO$_2$NR$^7$R$^8$; or

R$^1$ and R$^2$ taken together with the ring to which they are attached form a 5- or 6-membered monocyclic saturated or unsaturated ring optionally containing 0, 1 or 2 heteroatoms independently selected from nitrogen, oxygen or sulfur;

R$^3$ and R$^4$ are independently in each occurrence: lower alkyl, alkenyl, or cycloalkyl;

R$^5$ is independently in each occurrence:
(1) hydrogen,
(2) —COR$^9$,
(3) —COOR$^7$,
(4) —CONR$^7$R$^8$,
(5) —CO(CH$_2$)$_n$COR$^9$,
(6) —CO(CH$_2$)$_n$SO$_2$R$^9$,
(7) —CO(CH$_2$)$_n$CONR$^7$R$^8$,
(8) —CO(CH$_2$)$_n$SO$_2$NR$^7$R$^8$,
(9) —CO(CH$_2$)$_n$NR$^6$COR$^9$,
(10) —CO(CH$_2$)$_n$NR$^6$SO$_2$R$^9$,
(11) —CO(CH$_2$)$_n$NR$^6$CONR$^7$R$^8$,
(12) —CO(CH$_2$)$_n$NR$^6$SO$_2$NR$^7$R$^8$,
(13) —CSR$^9$,
(14) —CSNR$^7$R$^8$,
(15) —SO$_2$R$^9$,
(16) —SO$_2$NR$^7$R$^8$,
(17) —SO$_2$(CH$_2$)$_n$NR$^6$SO$_2$R$^9$, or
(18) —SO$_2$NR$^6$(CH$_2$)$_n$COOR$^7$;

wherein
n is 1–6;

R$^6$ and R$^7$ are independently in each occurrence: hydrogen or lower alkyl;

R$^8$ is independently in each occurrence: hydrogen, lower alkyl, cycloalkyl, aryl, or heteroaryl;

R$^9$ is independently in each occurrence:
(1) alkyl,
(2) cycloalkyl,
(3) arylalkyl,
(4) aryl, unsubstituted or mono-, di-, or tri-substituted aryl, the substituents being independently selected from lower alkyl, alkyloxy, halogen, hydroxyalkyl, haloalkyl, cyano, nitro, —CONR$^7$R$^8$, —COR$^7$, —COOR$^7$, —NR$^7$R$^8$, —NCOR$^9$, —SO$_2$R$^9$, —SO$_2$NR$^7$R$^8$, or —O(CH$_2$)$_p$X wherein p is 0–6 and X is haloalkyl or aryl,
(5) heterocyclyl, unsubstituted or mono- or di-substituted heterocyclyl, the substitutents independently selected from lower alkyl, hydroxy, hydroxyalkyl, oxo, —COR$^7$, or —COOR$^7$, or
(6) heteroaryl, unsubstituted or mono-, di-, or tri-substituted heteroaryl, the substituents being independently selected from lower alkyl, alkyloxy, halogen, hydroxyalkyl, haloalkyl, cyano, nitro, —CONR$^7$R$^8$, —COR$^7$, —COOR$^7$, —NR$^7$R$^8$, —NCOR$^9$, —SO$_2$R$^9$, —SO$_2$NR$^7$R$^8$, or —O(CH$_2$)$_p$X wherein p is 0–6 and X is haloalkyl or aryl;

as an individual isomer or as a racemic or non-racemic mixture of isomers, or a pharmaceutically acceptable salt thereof.

This invention further provides a pharmaceutical composition containing a therapeutically effective amount of a compound of Formula I in admixture with one or more suitable carriers.

This invention further provides a method of treating conditions which can be ameliorated by blocking the muscarinic receptors, including diseases and disorders of the gastrointestinal tract, genitourinary tract, and respiratory tract by administering a therapeutically effective amount of a compound of Formula I to a subject afflicted with such a condition.

DETAILED DESCRIPTION OF THE INVENTION

Definitions

Unless otherwise stated, the following terms used in the specification and claims have the meanings given below:

"Alkyl" means a monovalent branched or unbranched saturated hydrocarbon radical of one to twelve carbon atoms inclusive, such as methyl, ethyl, propyl, 1-ethylpropyl, 2-propyl, butyl, tert-butyl, n-octyl, n-nonyl, and the like.

"Lower alkyl" means an alkyl radical of one to six carbon atoms inclusive.

"Alkyloxy" means the group —O—R wherein R is alkyl as defined above.

"Cycloalkyl" means a monovalent saturated carbocyclic radical having from three to fourteen carbon atoms inclusive, e.g., cyclopropylmethyl, cyclopropylethyl, cyclobutyl, 3-ethylcyclobutyl, cyclopentyl, cyclohexyl, cycloheptyl, and the like.

"Alkenyl" means a linear monovalent hydrocarbon radical of two to six carbon atoms inclusive or a branched monovalent hydrocarbon radical of three to six carbon atoms inclusive containing a double bond, such as ethenyl, allyl, 1-propenyl, 2-butenyl, and the like.

"Halogen" means fluoro, chloro, bromo, or iodo.

"Haloalkyl" means alkyl as defined above substituted with one, two or three halogen atoms as defined above in any position, such as 1,2-difluoropropyl, 1,2-dichloropropyl, trifluoromethyl, 2,2,2-trifluoroethyl, 2,2,2-trichloroethyl, and the like.

"Hydroxyalkyl" means alkyl substituted by 1, 2 or 3 hydroxy groups, such as hydroxymethyl, 1-hydroxyethyl, 2-hydroxyethyl, 1,3-dihydroxybutyl, and the like.

"Aryl" means a monocyclic aromatic ring or a 9 to 14 membered bicyclic or tricyclic ring system in which at least one ring is aromatic in nature. Examples of aryl radicals include, but are not limited to, phenyl, naphthyl, biphenyl, diphenylmethyl, 9H-fluorenyl, indanyl, and the like.

"Arylalkyl" means the radical R$^a$R$^b$ where R$^a$ is aryl as defined above, and R$^b$ is alkyl as defined above, for example benzyl, phenylethyl, 3-phenylpropyl, and the like.

"Heteroaryl" means a monocyclic aromatic ring or a 9 to 14-membered bicyclic ring system in which at least one ring is aromatic in nature, and includes heterocycles having one, two or three heteroatoms within the ring, chosen from nitrogen, oxygen, and sulfur. Examples of heteroaryl radicals include, but are not limited to, furyl, 3,3-dimethyl-2,3-dihydrobenzofuryl, benzofuryl, 2,3-dihydrobenzofuryl, pyranyl, benzo[1,3]dioxolyl, 2,3-dihydrobenzo[1,4] dioxinyl, indolyl, 2,3-dihydroindolyl, pyridyl, pyrazolyl, pyrazinyl, quinolyl, 1,2,3,4-tetrahydroquinolyl, isoquinolyl, 1,2,3,4-tetrahydroisoquinolyl, pyrrolyl, imidazolyl, 1,2,3,4-tetrahydro[1,5]naphthyridinyl, 2H-3,4-dihydrobenzo[1,4] oxazine, thienyl, benzo[b]thienyl, and the like.

"Heterocyclyl" means a monovalent saturated carbocyclic radical having five, six or seven ring atoms of which one or two are selected from nitrogen, oxygen or sulfur. Examples of heterocyclyl radicals include, but are not limited to, tetrahydrofuranyl, tetrahydropyranyl, piperidinyl, piperazinyl, morpholino, thiomorpholino, 1,1-dioxothiomorpholino, imidazolidinyl, pyrrolidinyl, pyrrolidin-2-one, pyrrolidin-2,3-dione, and the like.

"Amino-protecting group" or "N-protecting group" means a protecting group that refers to those organic groups intended to protect the nitrogen atom against undesirable reactions during synthetic procedures and includes, but is not limited to benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by mild acids in the case of BOC, e.g., trifluoroacetic acid or hydrochloric acid in ethyl acetate, or by catalytic hydrogenation in the case of CBZ.

"Optional" or "optionally" means that the subsequently described event or circumstance may but need not occur, and that the description includes instances where the event or circumstance occurs and instances in which it does not. For example, "optionally substituted aryl" means that the aryl moiety may or may not be substituted and that the description includes both substituted and unsubstituted aryl.

"Inert organic solvent" or "inert solvent" means a solvent inert under the conditions of the reaction being described in conjunction therewith including, for example, benzene, toluene, acetonitrile, tetrahydrofuran, chloroform ($CHCl_3$), methylene chloride or dichloromethane ($CH_2Cl_2$), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The compounds of this invention may possess one or more asymmetric centers; such compounds can therefore be produced as mixtures of stereoisomers or as the individual isolated or purified (R)- or (S)-stereoisomers. The individual enantiomers may be obtained by resolving a racemic or non-racemic mixture of an intermediate at some appropriate stage of the synthesis followed by completion of the synthesis in a way that preserves chirality, or by resolution of the compound of Formula I by conventional means. The individual enantiomers as well as racemic or non-racemic mixtures thereof are encompassed within the scope of the present invention, all of which are intended to be depicted by the structures of this specification unless otherwise specifically indicated. The use of the symbol "(R)" or "(S)" preceding a substituent designates the absolute stereochemistry of that substituent according to the Cahn-Ingold-Prelog rules (Cahn et al. *Angew. Chem. Inter. Edit.* 1966, 5, 385; errata 511; Cahn et al. *Angew. Chem.* 1966, 78, 413; Cahn and Ingold *J. Chem. Soc.* (London) 1951, 612; Cahn et al. *Experientia* 1956, 12, 81; Cahn, *J. Chem. Educ.* 1964, 41, 116).

A "pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like, or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-napthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, tearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. The preferred pharmaceutically acceptable salts are the salts formed from hydrochloric acid, phosphoric acid, trifluoroacetic acid, and dibenzoyl-L-tartaric acid.

"Mammal" includes humans and all domestic and wild animals, including without limitation, cattle, horses, swine, sheep, goats, dogs, cats, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, and disease state being treated, the severity of the disease treated, the age and relative health of the subject, the route and form of administration, the judgement of the attending medical practitioner, and other factors.

Nomenclature

The naming and numbering of the compounds of this invention is illustrated below.

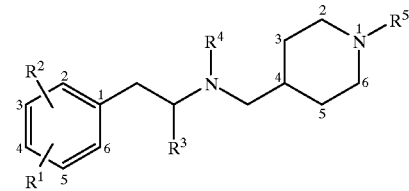

In general, the nomenclature used in this application is based on Autonom, a Beilstein Institute computerized system for the generation of IUPAC systematic nomenclature. However, because a strict adherence to these recommendations would result in the names changing substantially when only a single substituent is changed, compounds have been named in a form that maintains consistency of nomenclature for the basic structure of the molecule.

For example, a compound of Formula I wherein $R^1$ is hydrogen, $R^2$ is trifluoromethyl, $R^3$ is methyl, $R^4$ is cyclopropylmethyl, and $R^5$ is methanesulfonyl, is named N-[2-(4-trifluorophenyl)-1-methylethyl]-N-cyclopropylmethyl-(1-methanesulfonylpiperidin-4-ylmethyl)amine.

For example, a compound of Formula I wherein $R^1$ and $R^2$ taken together with the ring to which they are attached form 2,3-dihydrobenzofuran-5-yl, $R^3$ is methyl, $R^4$ is ethyl, and $R^5$ is dimethylaminocarbonyl, is named N-[2-(2,3-dihydrobenzofuran-5-yl)-1-methylethyl]-N-ethyl-[1-(dimethylaminocarbonyl)piperidin-4-ylmethyl]amine.

For example, a compound of Formula I wherein $R^1$ is hydrogen, $R^2$ is 4-methoxyphenylcarbonylamino, $R^3$ is methyl, $R^4$ is propyl, and $R^5$ is morpholine-4-carbonyl, is named N-{2-[3-(4-methoxyphenylcarbonylamino)phenyl]-1-methylethyl]-N-propyl-[1-(morpholine-4-carbonyl)piperidin-4-ylmethyl]amine.

Preferred Compounds

Among the family of compounds of the present invention set forth in the Summary of the Invention, certain compounds of Formula I are preferred. For example, preferred compounds of Formula I include those where $R^3$ and $R^4$ are each independently lower alkyl or cycloalkyl, more preferably $R^3$ and $R^4$ are each independently methyl, ethyl, propyl, isopropyl or cyclopropylmethyl; most preferably $R^3$ is methyl and $R^4$ is ethyl, propyl, isopropyl or cyclopropylmethyl.

Within this category, one preferred group includes the compounds where $R^5$ is —$SO_2R^9$ wherein $R^9$ is alkyl, more preferably methyl, ethyl, or propyl, most preferably methyl, where $R^5$ is —$COR^9$ wherein $R^9$ is heterocyclyl or heteroaryl, more preferably morpholino, piperidinyl or 1,2,3,4-tetrahydro[1,5]naphthyridinyl; where $R^5$ is $CONR^7R^8$ wherein $R^7$ and $R^8$ are each independently lower alkyl, more preferably methyl, ethyl, or propyl; where $R^5$ is —CO($CH_2)_n NR^6SO_2R^9$ wherein n is 1–6, $R^6$ is hydrogen and $R^9$ is lower alkyl, $R^9$ is more preferably methyl, ethyl, or propyl.

Another preferred group includes the compounds where $R^1$ and $R^2$ taken together with the ring to which they are attached form a 5- or 6-membered monocyclic saturated or unsaturated ring optionally containing 0, 1 or 2 heteroatoms independently selected from nitrogen, oxygen or sulfur, and in which the ring is unsubstituted or optionally mono- or di-substituted with lower alkyl or oxo; more preferably $R^1$ and $R^2$ taken together with the ring to which they are attached form a 5- or 6-membered monocyclic saturated ring optionally containing 0, 1 or 2 oxygen heteroatoms; most preferably $R^1$ and $R^2$ taken together with the ring to which they are attached form indanyl, 2,3-dihydrobenzofuran-5-yl, 2,3-dihydrobenzofuran-6-yl, 3,3-dimethyl-2,3-dihydrobenzofuran-6-yl, or 2,3-dihydrobenzo[1,4]dioxin-6-yl.

Another preferred group includes the compounds where $R^1$ is hydrogen and $R^2$ is alkyloxy, haloalkyl, or halogen; more preferably $R^2$ is methoxy, ethoxy, trifluoromethyl, chloro, or fluoro; or where $R^2$ is —$NR^6COR^9$ wherein $R^6$ is hydrogen and $R^9$ is aryl, unsubstituted or mono-, di-, or tri-substituted with lower alkyl, alkyloxy, halogen, or haloalkyl; more preferably $R^7$ is hydrogen and $R^9$ is phenyl, unsubstituted or mono-, di-, or tri-substituted with methyl, ethyl, methoxy, ethoxy, chloro, or trifluoromethyl.

Another preferred group includes the pharmaceutically acceptable salts of the compounds of the present invention where the pharmaceutically acceptable salts are formed from hydrochloric acid, phosphoric acid, or dibenzoyl-L-tartaric acid, more preferably the salts are formed from hydrochloric acid or phosphoric acid.

Exemplary particular preferred compounds are:
N-[2-(2,3,-Dihydrobenzofuran-5-yl)-1-methylethyl]-N-ethyl-(1-methanesulfonylpiperidin-4-ylmethyl)amine;
N-[2-(2,3-Dihydrobenzofuran-5-yl)-1-methylethyl]-N-propyl-(1-methanesulfonylpiperidin-4-ylmethyl)amine;
N-[2-(2,3-Dihydrobenzofuran-6-yl)-1-methylethyl]-N-propyl-[1-(morpholine-4-carbonyl)piperidin-4-ylmethyl]amine;
N-[2-(2,3-Dihydrobenzofuran-6-yl)-1-methylethyl]-N-cyclopropylmethyl-[1-(morpholine-4-carbonyl)piperidin-4-ylmethyl)amine;
N-[2-(2,3-Dihydrobenzofuran-5-yl)-1-methylethyl]-N-ethyl-[1-(morpholine-4-carbonyl)piperidin-4-ylmethyl]amine;
N-[2-(2,3-Dihydrobenzofuran-5-yl)-1-methylethyl]-N-propyl-[1-(morpholine-4-carbonyl)piperidin-4-ylmethyl]amine;
N-[2-(2,3-Dihydrobenzo[1,4]dioxin-6-yl)-1-methylethyl]-N-ethyl-[1-(morpholine-4-carbonyl)piperidin-4-ylmethyl]amine;
(S)-N-{3-[4-({[2-(2,3-Dihydrobenzofuran-5-yl)-1-methylethyl]ethylamino}methyl)piperidin-1-yl]-3-oxopropyl}methanesulfonamide;
N-[2-(Indan-5-yl)-1-methylethyl]-N-ethyl-(1-methanesulfonylpiperidin-4-ylmethyl)amine;
N-[2-(Indan-5-yl)-1-methylethyl]-N-propyl-(1-methanesulfonylpiperidin-4-ylmethyl)amine;
N-[2-(3,3-Dimethyl-2,3-dihydrobenzofuran-6-yl)-1-methylethyl]-N-ethyl-[1-(morpholine-4-carbonyl)piperidin-4-ylmethyl]amine;
N-[2-(3,3-Dimethyl-2,3,-dihydrobenzofuran-6-yl)-1-methylethyl]-N-ethyl-(1-methanesulfonylpiperidin-4-ylmethyl)amine;
N-[2-(4-Methoxyphenyl)-1-methylethyl]-N-ethyl-[1-(dimethylaminocarbonyl)piperidin-4-ylmethyl]amine;
N-[2-(3-Trifluoromethylphenyl)-1-methylethyl]-N-ethyl-[1-(dimethylaminocarbonyl)piperidin-4-ylmethyl]amine;
N-[2-(3-Trifluoromethylphenyl)-1-methylethyl]-N-ethyl-[1-(piperidine-1-carbonyl)piperidin-4-ylmethyl]amine;
N-[2-(4-Trifluoromethylphenyl)-1-methylethyl]-N-ethyl-[1-(piperidine-1-carbonyl)piperidin-4-ylmethyl]amine;
N-[2-(4-Trifluoromethylphenyl)-1-methylethyl]-N-ethyl-[1-(dimethylaminocarbonyl)piperidin-4-ylmethyl]amine;
N-[2-(3-Trifluoromethylphenyl)-1-methylethyl]-N-ethyl-[1-(morpholine-4-carbonyl)piperidin-4-ylmethyl]amine;
N-[2-(3-Trifluoromethylphenyl)-1-methylethyl]-N-ethyl-[1-(1,2,3,4-tetrahydro[1,5]naphthyridine-1-carbonyl)piperidin-4-ylmethyl]amine;
N-[2-(3-Chlorophenyl)-1-methylethyl]-N-ethyl-[1-(piperidine-1-carbonyl)piperidin-4-ylmethyl]amine;
N-[2-(3-Trifluoromethylphenyl)-1-methylethyl]-N-propyl-[1-(morpholine-4-carbonyl)piperidin-4-ylmethyl]amine;
N-{2-[3-(4-Methoxyphenylcarbonylamino)phenyl]-1-methylethyl}-N-propyl-[1-(morpholine-4-carbonyl)piperidin-4-ylmethyl]amine; and
N-{2-[3-(4-Methylphenylcarbonylamino)phenyl]-1-methylethyl}-N-propyl-[1-(morpholine-4-carbonyl)piperidin-4-ylmethyl]amine.

GENERAL SYNTHETIC SCHEME

Compounds of this invention can be made by the methods depicted in the reaction schemes shown below.

The starting materials and reagents used in preparing these compounds are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C., and most preferably at about room (or ambient) temperature, e.g., about 20° C.

In general, the compounds of Formula I are prepared by reacting an aldehyde (piperidine-4-carboxaldehyde) with an $R^4$-substituted amine under reductive amination conditions to form the corresponding ethyl-piperidin-4-ylmethyl amines or by acylation of an $R^4$-substituted amine under acylation conditions followed by reduction. Schemes A and B describe methods to generate the $R^4$-substituted amines and piperidine-4-carboxaldehydes, respectively. Schemes C to K describe methods to generate the compounds of Formula I with varying $R^5$. Schemes to P describe methods to generate the compounds of Formula I with varying $R^2$.

Scheme A
Scheme A describes methods of preparing $R^4$-substituted amines of formula 4 where $R^1$, $R^2$, $R^3$ and $R^4$ are as defined in the Summary of the Invention.

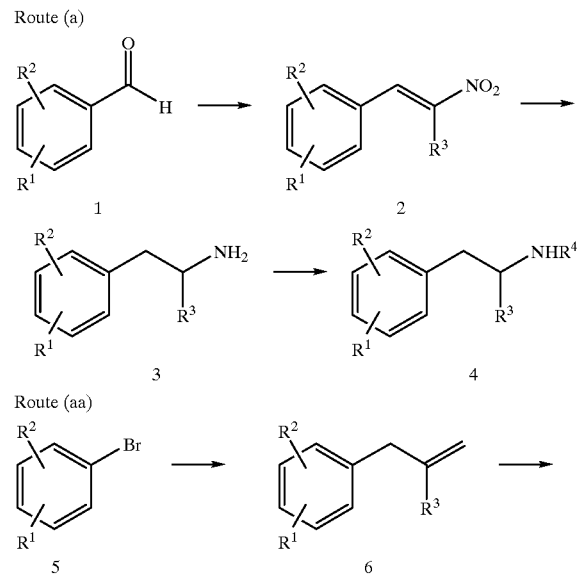

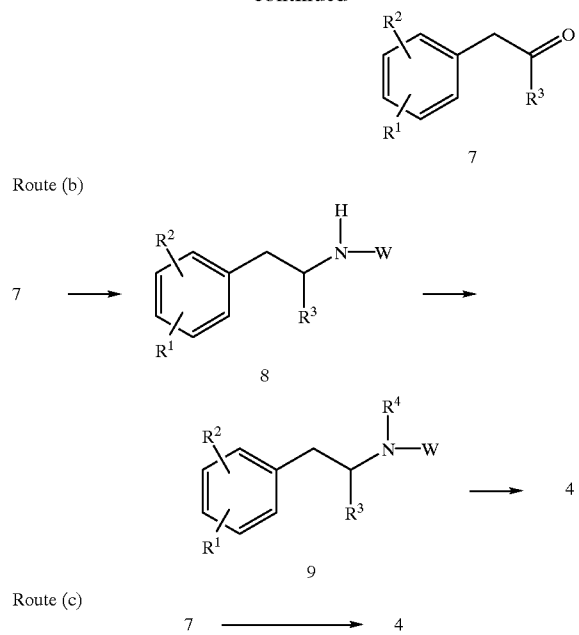

In route (a), an $R^4$-substituted amine 4 can be prepared from the corresponding aldehyde 1 by methods known to one of ordinary skill in the art. The aldehyde 1 is commercially available or can be synthesized by one of ordinary skill in the art. A nitrostyrene 2 can be prepared by reacting the corresponding aldehyde 1 with a nitroalkane under Knoevenagel or Henry reaction conditions, for example as described by Hass and Riley *Chem. Reviews* 1943, 22, 406. A primary amine 3 can be prepared by reducing the nitrostyrene 2 to a saturated amine. Suitable reducing conditions include lithium aluminum hydride in diethyl ether or tetrahydrofuran, or borane/sodium borohydride in tetrahydrofuran.

An $R^4$-substituted amine 4 can be prepared by reacting compound 3 with an aldehyde $R^4$CHO under reductive amination conditions; or with an acylating agent $R^4$C(O)L where L is a leaving group, such as chloro, followed by reduction; or with an alkylating agent $R^4$L where L is a leaving group such as chloro, under alkylating conditions.

In route (aa), a ketone 7 can be prepared, for example from a bromo compound 5. A bromo compound 5 is converted to an organometallic reagent, for example a Grignard reagent, by methods known in the art. The reaction proceeds in the presence of a metal such as magnesium, zinc or aluminum, preferably magnesium, and an activating agent such as 1,2-dibromoethane. Suitable inert organic solvents for the reaction include tetrahydrofuran, benzene, toluene and the like, preferably tetrahydrofuran. An alkene compound 6 is prepared by coupling the organometallic compound with an alkenyl halide, for example 3-bromo-2-methylpropene. The ketone 7 is formed upon oxidation of the alkene compound 6, for example, by ozonolysis followed by treatment with a reducing agent such as thiourea, dimethyl sulfide, trimethyl phosphite, preferably thiourea. The reaction is carried out in a mixture of suitable organic solvents such as dichloromethane and methanol. Alternatively, a ketone 7 is commercially available or can be synthesized by one of ordinary skill in the art, for example as described by Stoemer and Stroh *Chemische Berichte* 1935, 68, 2112.

Alternatively, in route (b), a $R^4$-substituted amine 4 or its enantiomerically pure isomers can be prepared from the corresponding ketone 7 by methods described in the chemical literature, for example Nichols et al. *J. Med. Chem.* 1973, 16, 480–483; *J. Med. Chem.* 1986, 29, 2009–2015; and *J. Med. Chem.* 1991, 34, 1662–1668.

A compound 8 where W is a removable chiral auxiliary group is formed by reacting a corresponding ketone 7 with a chiral auxiliary such as 1-phenylethylamine or 1-(2-naphthalenyl)ethylamine under reducing conditions. Suitable reducing conditions include for example hydrogen and a hydrogenation catalyst such as Raney nickel, platinum or palladium catalysts (e.g., $PtO_2$ or Pd/C), or other reducing agents such as sodium cyanoborohydride, sodium triacetoxyborohydride, sodium borohydride, and the like. Suitable solvents for sodium cyanoborohydride include alcoholic solvents such as methanol or ethanol, preferably ethanol. Suitable solvents for sodium triacetoxyborohydride include aprotic organic solvents such as tetrahydrofuran, acetonitrile or dichloroethane.

An $R^4$-substituted compound 9 is prepared by treating an amine compound 8 with an aldehyde under reductive amination conditions, an acylating agent followed by reduction, or an alkylating agent.

An $R^4$-substituted amine 4 is prepared by removing the chiral auxiliary group W from compound 9 by catalytic hydrogenolysis. Suitable catalytic hydrogenolysis conditions include platinum or palladium catalyst, in the presence of hydrogen donors, for example ammonium formate. Suitable solvents for the reaction include alcoholic solvents such as methanol or ethanol.

Alternatively, in route (c), an $R^4$-substituted amine 4 can be prepared from the corresponding ketone 7 by methods generally known in the chemical literature. The ketone 7 is reacted with a primary amine $R^4NH_2$ such as ethylamine under reductive amination reaction conditions. Suitable reductive amination procedures are described in the chemical literature. For example, Magid, A. et al. *J. Org. Chem.* 1996, 61, 3849–386 describes a method utilizing sodium triacetoxyborohydride as the reducing agent; and Borch, R. et al. *J. Am. Chem. Soc.* 1971, 93, 2897–2904 describes a method utilizing sodium cyanoborohydride as the reducing agent.

Exemplary preparations of a compound of formula 7 utilizing the reaction conditions described in Scheme A, route (aa) is given in Preparation 1; a compound of formula 4 described in routes (b) and (c) are given in Preparations 2 and 3, respectively.

Scheme B
Scheme B describes a method of preparing piperidine-4-carboxaldehydes of formula 13 or 17 where P is an amino-protecting group.

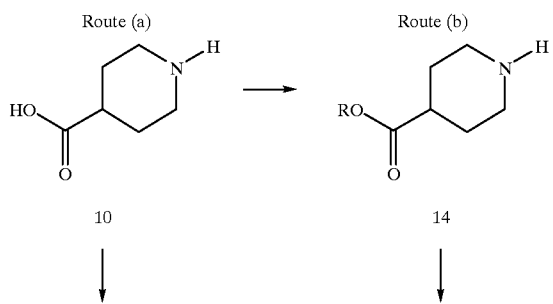

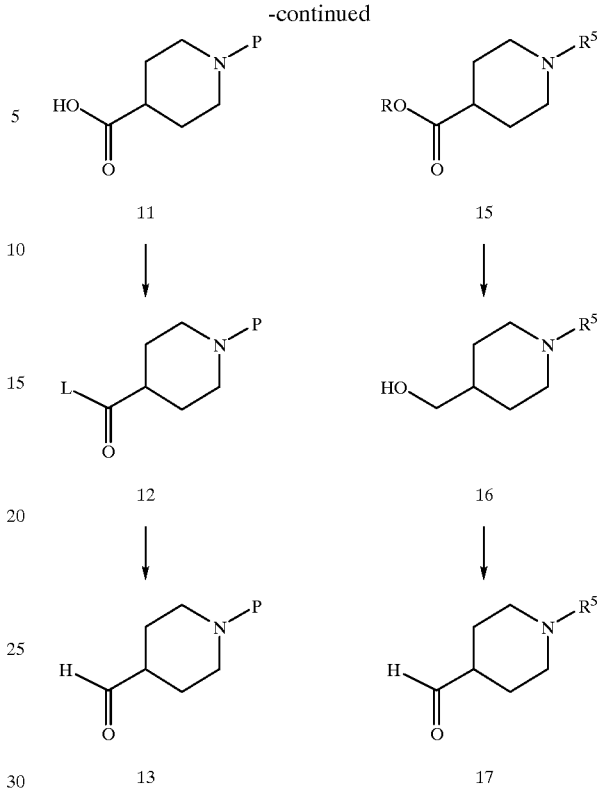

The piperidine carboxylic acid 10, the N-protected activated derivative 12, and the piperidine carboxylic acid ester 14 are commercially available or can be synthesized by one of ordinary skill in the art.

In route (a), an N-protected piperidine-4-carboxylic acid 11 where P is an amino-protecting group is prepared by attaching a suitable amino-protecting group such as benzyl, tert-butoxycarbonyl (BOC) or carbobenzyloxy (CBZ) to the 4-piperidinecarboxylic acid 10 by methods known to one of ordinary skill in the art. Suitable solvents for the reaction include dichloromethane, dichloroethane, xylenes and the like.

An N-protected activated derivative 12 where L is a leaving group such as N-methoxy-N-methylamino is prepared by treating compound 11 with N,O-dimethylhydroxylamine hydrochloride by methods known to one of ordinary skill in the art.

An N-protected piperidine-4-carboxaldehyde 13 is prepared by treating compound 12 with a reducing agent such as lithium aluminum hydride, sodium aluminum hydride or diisobutylaluminum hydride. Suitable solvents for the reaction include aprotic organic solvents such as diethyl ether, dioxane, tetrahydrofuran, and the like.

Alternatively, in route (b), an N-substituted 4-piperidine carboxylic acid ester 15 is prepared by treating compound 14 with a sulfonylating agent $R^5SO_2L$ or an acylating agent $R^5COL$ where L is a leaving group such as halo, preferably chloro. The reaction is carried out in the presence of a base, for example triethylamine, in a suitable inert organic solvent such as dichloromethane, dichloroethane, carbon disulfide, and the like, preferably dichloromethane.

An N-substituted 4-hydroxymethylpiperidine 16 is prepared by treating compound 15 with a reducing agent such as lithium aluminum hydride, diisobutylaluminum hydride, lithium triborohydride, preferably lithium aluminum hydride. Suitable inert organic solvents for the reaction include aprotic organic solvents such as diethyl ether, dioxane, tetrahydrofuran, and the like.

An N-substituted piperidine-4-carboxaldehyde 17 is prepared by treating the 4-hydroxymethylpiperidine 16 with an oxidizing agent such as dimethylsulfoxide in the presence of oxalyl chloride. Suitable solvents for the reaction include inert organic solvents such as halogenated hydrocarbons, for example dichloromethane or dichloroethane.

Exemplary preparations of compounds of formula 13 and 17 utilizing the reaction conditions described in Scheme B are given in Preparations 4 and 5, respectively.

Scheme C

Scheme C, in general, describes methods of preparing a compound of Formula I where $R^5$ is hydrogen. This compound is designated as a compound of Formula Ia.

Route (a)

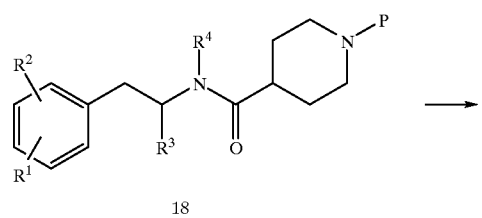

18

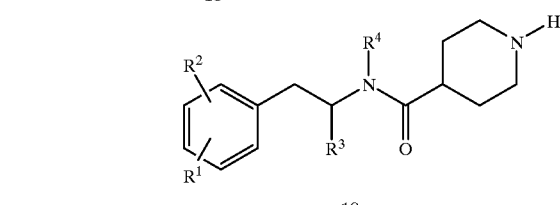

19

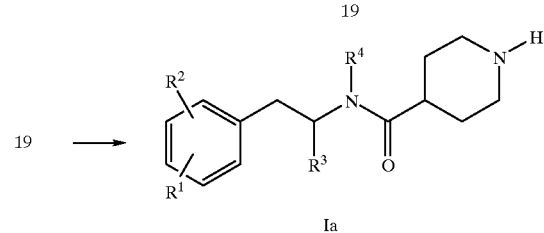

Ia

Route (b)

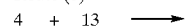

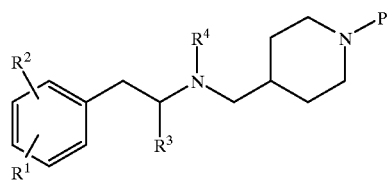

20

In route (a), an N-protected piperidine-4-carboxamide 18 where P is an amino-protecting group, preferably CBZ, is prepared by reacting an $R^4$-substituted amine 4 with an activated derivative 12 under acylating conditions where L is chloro. The reaction proceeds in the presence of a base such as aqueous potassium carbonate or aqueous sodium carbonate. Suitable solvents for the reaction include inert organic solvents such as dichloromethane, dichloroethane, toluene or ethyl acetate, preferably toluene.

A piperidine-4-carboxamide 19 is prepared by removing the N-protecting group from compound 18. When the N-protecting group is CBZ, compound 19 is prepared under hydrogenation conditions such as Raney nickel or a platinum or palladium catalyst in alcoholic solvents such as methanol or ethanol. When the N-protecting group is BOC, compound 19 is prepared by treatment with a strong organic acid such as trifluoroacetic acid in an inert organic solvent such as halogenated hydrocarbons, for example dichloromethane or dichloroethane, preferably dichloromethane.

A compound of Formula Ia is prepared by treating compound 19 with a reducing agent such as lithium aluminum hydride, diborane, and the like, preferably lithium aluminum hydride. The reaction proceeds at reflux temperature in an inert organic solvent such as diethyl ether, dioxane, tetrahydrofuran, and the like, preferably tetrahydrofuran.

Alternatively, in route (b) an N-protected piperidin-4-ylmethyl amine 20 where P is preferably BOC, is prepared by reacting a $R^4$-substituted amine 4 with a piperidine-4-carboxaldehyde 13 under reductive amination reaction conditions. The reaction proceeds in the presence of a reducing agent such as sodium triacetoxyborohydride. Suitable solvents for the reaction are inert organic solvents such as halogenated hydrocarbons, for example dichloromethane or dichloroethane, preferably dichloroethane.

A compound of Formula Ia is prepared by deprotecting compound 20 in the presence of a strong organic acid such as trifluoroacetic acid. The reaction proceeds at ambient temperature. Suitable solvents for the reaction include halogenated hydrocarbons such as dichloromethane, dichloroethane, and the like, preferably dichloromethane.

Exemplary preparations of a compound of Formula la utilizing the reaction conditions described in Scheme C is given in Example 1.

Scheme D

Scheme D describes an alternative method of preparing a compound of Formula I where $R^5$ is hydrogen. This compound is designated as a compound of Formula Ia.

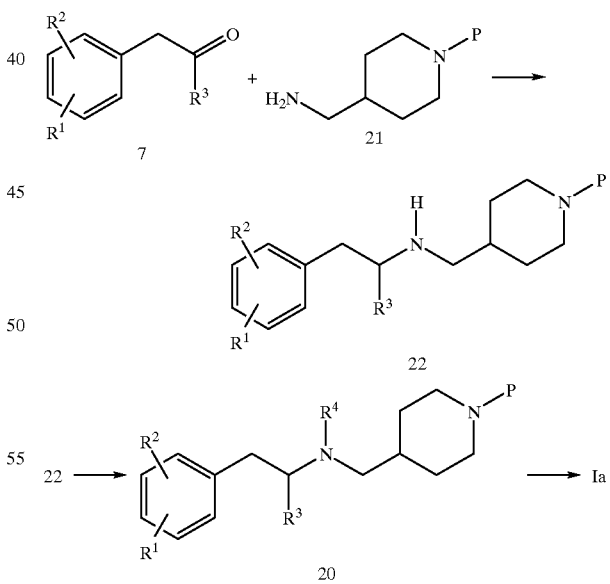

The ketone 7 can be prepared as previously described in Scheme A, route (aa).

An N-protected 4-aminomethylpiperidine 21 where P is an amino-protecting group, particularly BOC, is prepared by the method described in Prugh, J. D. *Synth. Commun.* 1992, 22, 2357–2360.

An N-protected amine 22 is prepared by coupling the ketone 7 with compound 21 under reductive amination conditions. The reaction proceeds in the presence of a reducing agent such as sodium cyanoborohydride. Suitable solvents for the reaction are alcoholic solvents such as methanol or ethanol.

An $R^4$-substituted amine 20 is prepared by reacting compound 22 with an aldehyde $R^4$CHO under reductive amination conditions in the presence of a reducing agent such as sodium triacetoxyborohydride. Suitable solvents for the reaction include inert organic solvents such as dichloromethane, dichloroethane, tetrahydrofuran or acetonitrile.

A compound of Formula Ia is prepared by removing the N-protecting group from compound 20. When the N-protecting group is CBZ, compound 20 is prepared under hydrogenation conditions such as Raney nickel, or a platinum or palladium catalyst in alcoholic solvents such as methanol or ethanol. When the N-protecting group is BOC, compound 20 is prepared by treatment with a strong organic acid such as trifluoroacetic acid in an inert organic solvent such as dichloromethane or dichloroethane, preferably dichloromethane. The reaction proceeds at ambient temperature.

Exemplary preparations of a compound of Formula Ia utilizing the reaction conditions described in Scheme D are given in Example 2.

Scheme E
Scheme E describes an alternative method of preparing a compound of Formula I where $R^5$ is ——$COR^9$ or ——$CSR^9$. This compound is designated as a compound of Formula Ib.

Route (a)

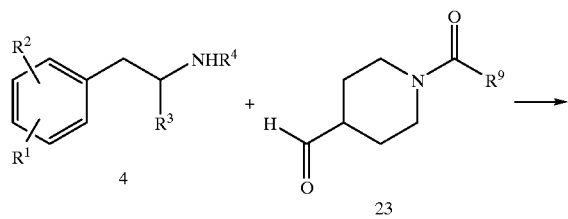

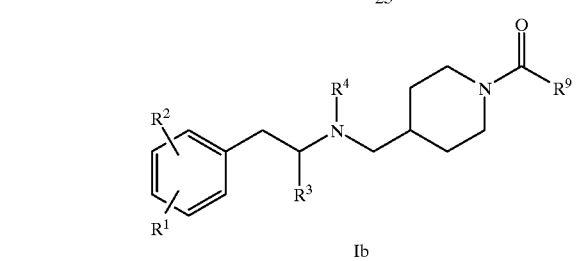

Route (b)

-continued

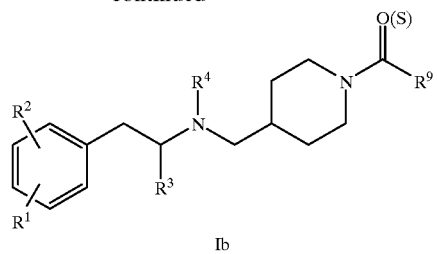

In route (a), a compound of Formula Ib is prepared by reacting an $R^4$-substituted amine 4 with a piperidine-4-carboxaldehyde 23 under reductive amination conditions described in Scheme C.

Alternatively, in route (b), a compound of Formula Ib is prepared by reacting a compound of Formula Ia with an acylating reagent $R^9C(O)L/R^9C(S)L$ where L is a leaving group, particularly chloro. The reaction is carried out in the presence of a base such as aqueous sodium or aqueous potassium carbonate in an inert organic solvent such as aromatic hydrocarbons, for example toluene, benzene and the like.

Exemplary preparations of a compound of Formula Ib utilizing the reaction conditions described in Scheme E are given in Example 3.

Scheme F
Scheme F describes an alternative method of preparing a compound of Formula I where $R^5$ is ——$CONR^7R^8$ or ——$CSNR^7R^8$. This compound is designated as a compound of Formula Ic.

Route (a)

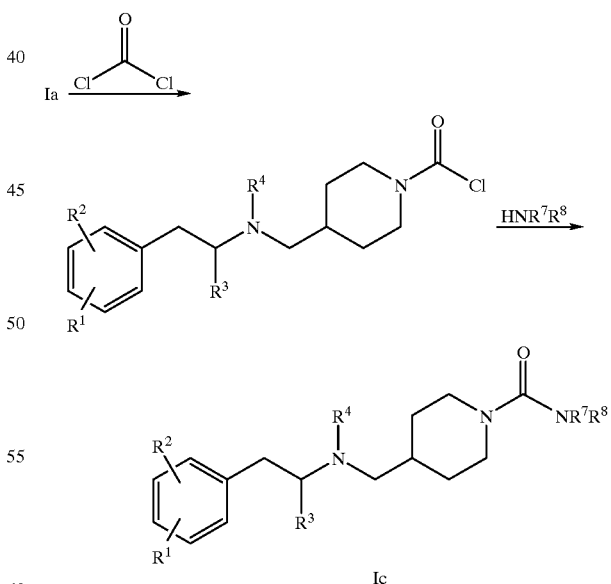

Route (b)

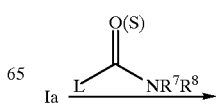

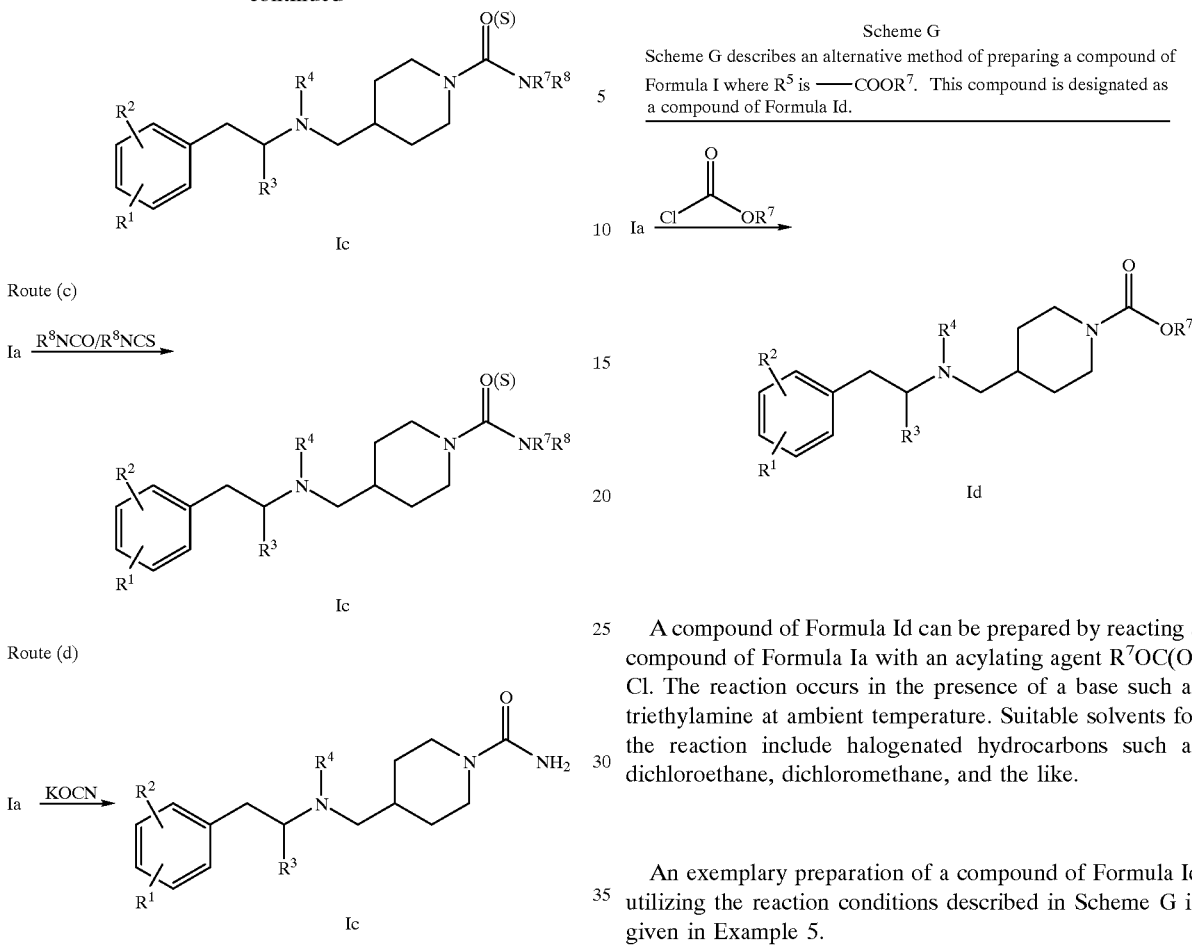

Route (c)

Route (d)

In route (a), a compound of Formula Ic is prepared by reacting a compound of Formula Ia with phosgene or a phosgene equivalent compound such as triphosgene, followed by treatment with a primary or secondary amine. The reaction occurs at ambient temperature. Suitable solvents include aprotic organic solvents such as diethyl ether, dioxane, tetrahydrofuran, and the like.

Alternatively, in route (b), a compound of Formula Ic is prepared by reacting a compound of Formula Ia with a carbamyl/thiocarbamyl halide. The reaction occurs in the presence of a base, such as triethylamine, at ambient temperature. Suitable solvents include halogenated hydrocarbons such as dichloroethane or dichloromethane.

Alternatively, in route (c), a compound of Formula Ic is prepared by reacting a compound of Formula Ia with an isocyanate/isothiocyanate in an aprotic organic solvent such as diethyl ether, tetrahydrofuran, toluene, and the like.

Alternatively, in route (d), a compound of Formula Ic is prepared by reacting a compound of Formula Ia with an aqueous solution of a cyanate/thiocyanate salt such as potassium cyanate/thiocyanate or sodium cyanate/thiocyanate under Wohler reaction conditions. The reaction occurs at reflux temperature.

Exemplary preparations of a compound of Formula Ic utilizing the reaction conditions described in Scheme F are given in Example 4.

Scheme G

Scheme G describes an alternative method of preparing a compound of Formula I where $R^5$ is ―――$COOR^7$. This compound is designated as a compound of Formula Id.

A compound of Formula Id can be prepared by reacting a compound of Formula Ia with an acylating agent $R^7OC(O)$Cl. The reaction occurs in the presence of a base such as triethylamine at ambient temperature. Suitable solvents for the reaction include halogenated hydrocarbons such as dichloroethane, dichloromethane, and the like.

An exemplary preparation of a compound of Formula Id utilizing the reaction conditions described in Scheme G is given in Example 5.

Scheme H

Scheme H describes an alternative method of preparing a compound of Formula I where $R^5$ is ―――$CO(CH_2)_nNR^6SO_2R^9$ or ―――$CO(CH_2)_nNR^6COR^9$ where $R^6$ is hydrogen. This compound is designated as a compound of Formula Ie.

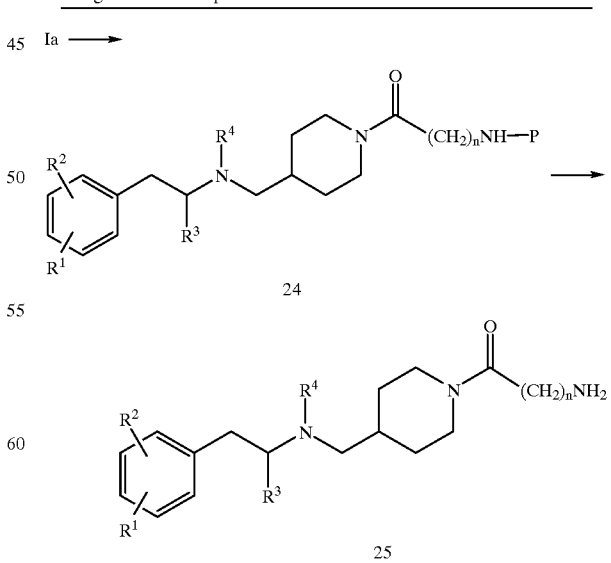

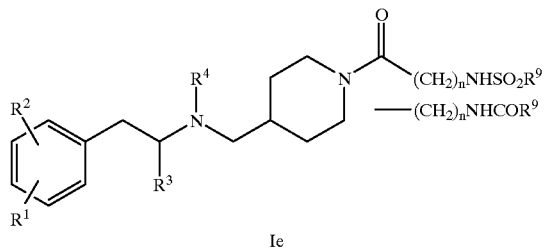

Ie

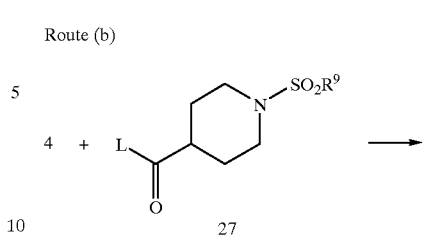

Route (b)

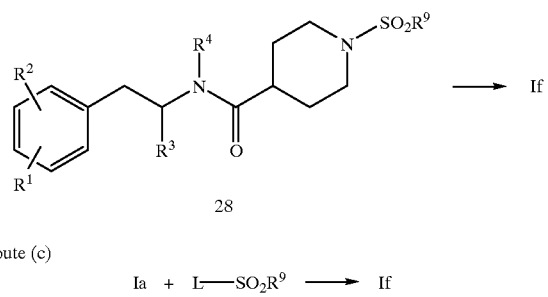

28

Route (c)

Ia + L—SO₂R⁹ ⟶ If

An N-protected compound of formula 24 is prepared by reacting a compound of Formula Ia with an N-protected amino acid in the presence of a peptide coupling reagent such as carbonyldiimidazole. The reaction occurs at ambient temperature. Suitable solvents for the reaction include halogenated hydrocarbons such as dichloromethane or dichloroethane.

A deprotected compound of formula 25 is prepared by either treating compound 24 with a strong organic acid such as trifluoroacetic acid at ambient temperature when the amino-protecting group is BOC; or utilizing hydrogenation conditions when the amino-protecting group is CBZ.

A compound of Formula Ie is prepared by reacting a compound 25 with a sulfonyl halide or acyl halide in the presence of a base, such as diisopropylethylamine. Suitable solvents for the reaction include halogenated organic solvents such as dichloromethane, dichloroethane, and the like.

An exemplary preparation of a compound of Formula Ie utilizing the reaction conditions described in Scheme H is given in Example 6.

Scheme I

Scheme I describes an alternative method of preparing a compound of Formula I where R⁵ is ——SO₂R⁹. This compound is designated as a compound of Formula If.

Route (a)

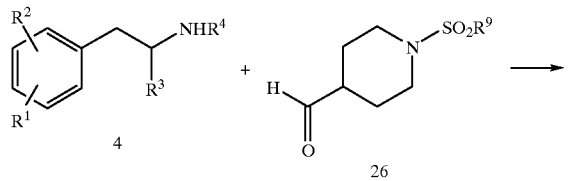

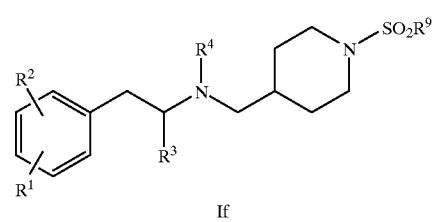

If

In route (a), a compound of Formula If is prepared by reacting an R⁴-substituted amine 4 with a piperidine-4-carboxaldehyde 26, and utilizing the reductive amination conditions described in Scheme C.

Alternatively, in route (b), a carboxamide 28 is prepared by reacting an R⁴-substituted amine 4 with an activated derivative 27 where L is a leaving group, particularly chloro, in the presence of a base such as triethylamine. Suitable solvents for reaction include dichloromethane, dichloroethane or pyridine.

A compound of Formula If is prepared by treating compound 28 with a reducing agent such as lithium aluminum hydride or diborane. The reaction proceeds at a temperature of about 0° C. under an inert atmosphere. Suitable solvents for the reaction include aprotic organic solvents such as diethyl ether, dioxane or tetrahydrofuran.

Alternatively, in route (c), a compound of Formula If is prepared by reacting a compound of Formula Ia with a sulfonyl halide R⁹SO₂L where L is a leaving group, particularly chloro. Sulfonyl halides are commercially available or may be prepared by methods such as those described in Langer, R. F. Can. J. Chem. 1983, 61, 1583–1592; Aveta, R. et al. Gazetta Chimica Italiana 1986, 116, 649–652; King, J. F. and Hillhouse, J. H. Can. J. Chem. 1976, 498; and Szymonifka, M. J. and Heck, J. V. Tetrahedron Lett. 1989, 2860–2872. The reaction is carried out in the presence of a base such as triethylamine in a suitable solvent such as dichloromethane, dichloroethane, and the like.

An exemplary preparation of a compound of Formula If utilizing the reaction conditions described in Scheme I is given in Example 7.

Scheme J

Scheme J describes an alternative method of preparing a compound of Formula I where $R^5$ is ——$SO_2NR^7R^8$ or ——$SO_2NR^6(CH_2)_nCOOR^7$. These compounds are designated as a compound of Formula Ig and Formula Ig', respectively.

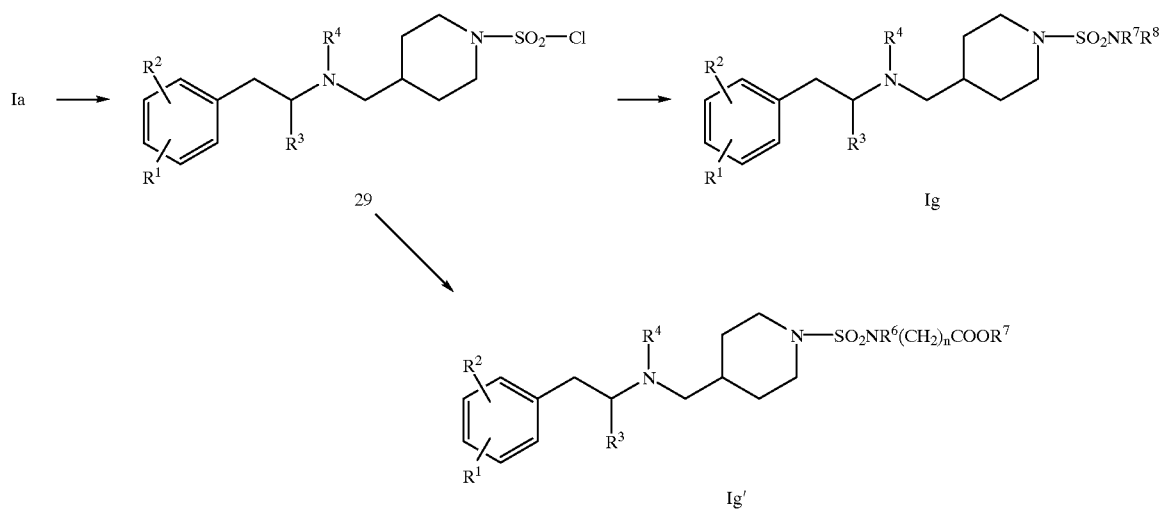

A sulfonylated compound 29 is prepared by reacting a compound of Formula Ia with chlorosulfonic acid followed by phosphorus pentachloride. The reaction proceeds in the presence of a base such as triethylamine. Suitable solvents for the reaction include halogenated hydrocarbons such as dichloromethane, dichloroethane, and the like.

A compound of Formula Ig is prepared by reacting a compound 29 with a primary or secondary amine. The reaction occurs in the presence of a base such as diisopropylethylamine. Suitable solvents for the reaction include aprotic solvents such as tetrahydrofuran, methylene chloride, and the like.

Optionally, a compound of Formula Ig' can be prepared by reacting a compound 29 with an amino acid. The reaction proceeds at reflux temperature in the presence of alkylsilyl cyanide. Suitable solvents for the reaction include aprotic polar solvents such as acetonitrile, tetrahydrofuran, and the like.

Exemplary preparations of a compound of Formula Ig or Formula Ig' utilizing the reaction conditions described in Scheme J are given in Example 8.

Scheme K

Scheme K describes an alternative method of preparing a compound of Formula I where $R^5$ is ——$SO_2(CH_2)_2NR^6SO_2R^9$ where $R^6$ is hydrogen. This compound is designated as a compound of Formula Ih.

Ia ⟶

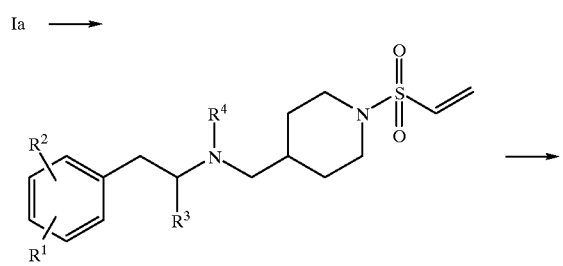

-continued

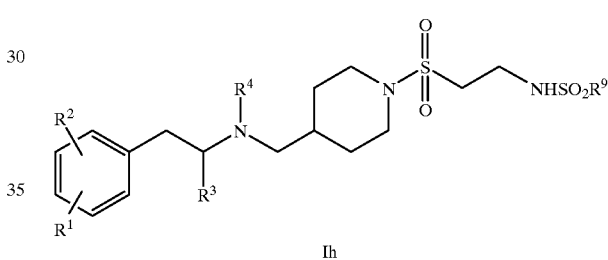

A vinyl sulfonamide compound 30 is prepared by reacting a compound of Formula Ia with a sulfonylating agent such as 2-chloroethylsulfonyl chloride in a suitable solvent such as dichloromethane or dichloroethane.

A compound of Formula Ih is prepared by reacting compound 30 with a sulfonamide $H_2NSO_2R^9$ in the presence of a strong base such as sodium hydride. Suitable solvents for the reaction include aprotic polar solvents such as tetrahydrofuran or dimethylformamide.

Exemplary preparations of a compound of Formula Ih utilizing the reaction conditions described in Scheme K are given in Example 9.

Scheme L

Scheme L describes an alternative method of preparing a compound of Formula I where $R^2$ is ——$NR^6COR^9$ where $R^6$ is hydrogen. This compound is designated as a compound of Formula Ij.

Route (a)

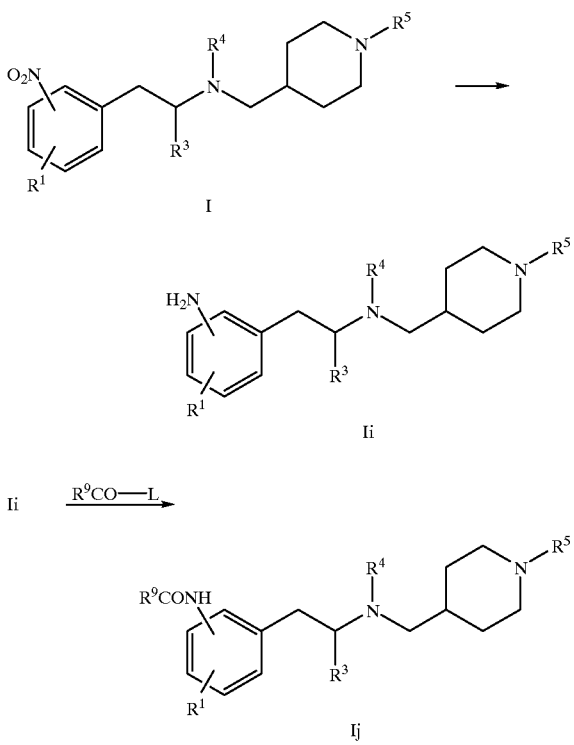

Route (b)

Route (c)

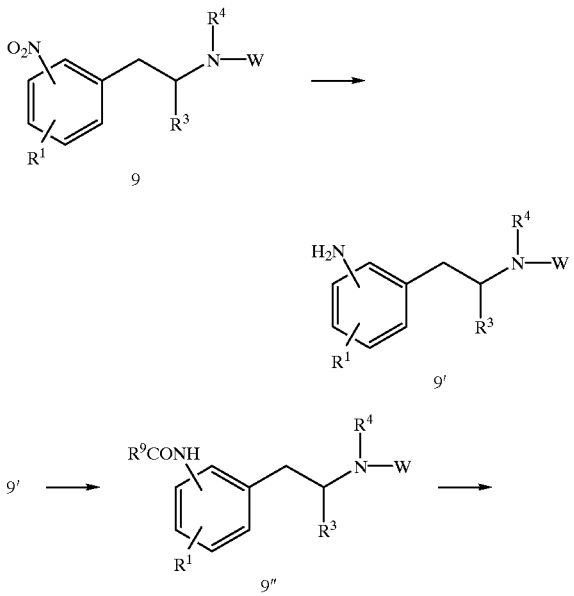

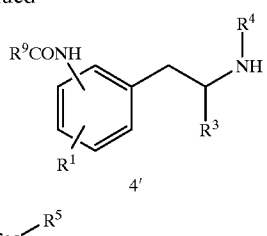

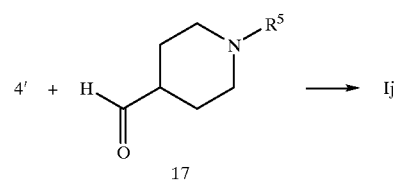

In general, the aniline compounds of Formula Ii or Formula 9' can be prepared by reducing the nitro group to an amino group by utilizing the reaction conditions described in Scheme A.

In route (a), a compound of Formula Ij can be prepared by reacting the aniline of Formula Ii with an acylating reagent $R^9C(O)L$ where L is a leaving group, particularly chloro, and utilizing the reaction conditions described in Scheme E.

Alternatively, in route (b), a compound of Formula Ij can be prepared by coupling a compound of Formula Ii with a carboxylic acid derivative $R^9COOH$ in the presence of a coupling reagent such as N,N'-carbonyl-diimidazole (CDl), dicyclohexyl-carbodiimide (DCC) or 1-(3-dimethylaminopropyl)-3-ethylcarbodiimide hydrochloride (EDCl). The reaction proceeds in conjunction with an additive such as 1-hydroxybenzotriazole hydrate. Suitable solvents for the reaction include aprotic organic solvents such as tetrahydrofuran, N,N-dimethylformamide, and the like.

Alternatively, in route (c), a compound of formula 4' is prepared by removing the chiral auxiliary group W from compound 9" by utilizing the reaction conditions described in Scheme A, route (b). The compound of Formula Ij is then prepared by reacting the amine 4' with a piperidine-4-carboxaldehyde 17, and utilizing the reductive amination conditions described in Scheme C, route (b).

Exemplary preparations of a compounds of Formula Ij, utilizing the reaction conditions described in Scheme L are given in Example 10.

Scheme M

Scheme M describes methods of preparing a compound of Formula I where $R^2$ is ——$NR^6CONR^7R^8$ or ——$NR^6CSNR^7R^8$ where $R^6$ is hydrogen. This compound is designated as a compound of Formula Ik.

Route (a)

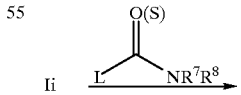

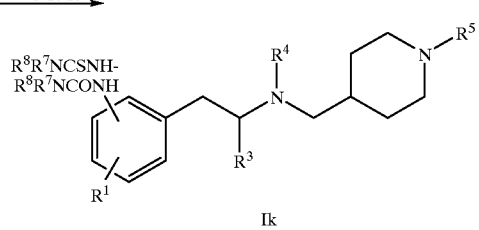

Route (b)

Ii 

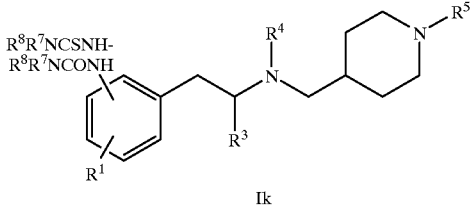

Ik

Route (c)

Ii 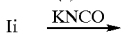

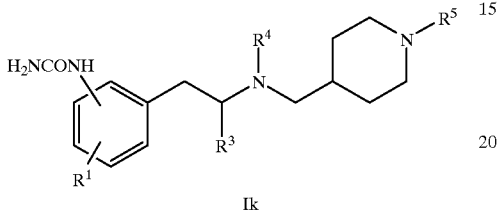

Ik

In route (a), a compound of Formula Ik is prepared by reacting an aniline compound of Formula Ii with a carbamyl/thiocarbamyl halide, and utilizing the reaction conditions described in Scheme F, route (b).

Alternatively, in route (b), a compound of Formula Ik is prepared by reacting an aniline compound of Formula Ii with an isocyanate/isothiocyanate, and utilizing the reaction conditions described in Scheme F, route (c).

Alternatively, in route (c), a compound of Formula Ik is prepared by reacting an aniline compound of Formula Ii with an aqueous solution of a cyanate/thiocyanate salt such as potassium cyanate/thiocyanate, and utilizing the reaction conditions described in Scheme F, route (d).

Exemplary preparations of compounds of Formula Ik utilizing the reaction conditions described in Scheme M are given in Example 11.

Scheme N

Scheme N describes a method of preparing a compound of Formula I where $R^2$ is ——$NR^6SO_2R^9$ where $R^6$ is hydrogen. This compound is designated as a compound of Formula Il.

Ii 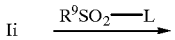

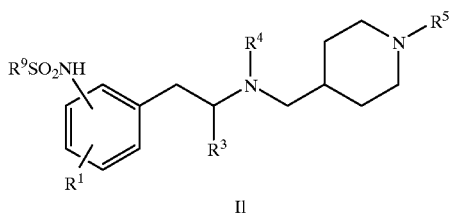

Il

A compound of Formula Il, can be prepared by reacting an aniline compound of Formula Ii with a sulfonylating agent $R^9SO_2L$ where L is a leaving group, particularly chloro, and utilizing the reaction conditions described in Scheme I, route (c).

Exemplary preparations of compounds of Formula Il utilizing the reaction conditions described in Scheme N are given in Example 12.

Scheme O

Scheme O describes a method of preparing a compound of Formula I where $R^2$ is ——$NR^6SO_2NR^7R^8$ where $R^6$ is hydrogen. This compound is designated as a compound of Formula Im.

Ii 

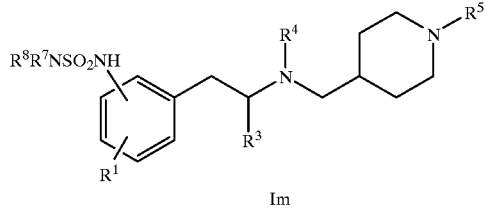

Im

A compound of Formula Im can be prepared by reacting an aniline compound of Formula Ii with a sulfonylating agent $R^8R^7NSO_2L$ where L is a leaving group, particularly chloro, and utilizing the reaction conditions described in Scheme J.

Exemplary preparations of compounds of Formula Im, utilizing the reaction conditions described in Scheme O are given in Example 13.

Scheme P

Scheme P describes a method of preparing a compound of Formula I where $R^2$ is ——$NR^7R^8$ where $R^7$ and $R^8$ are each methyl. This compound is designated as a compound of Formula In Ii 

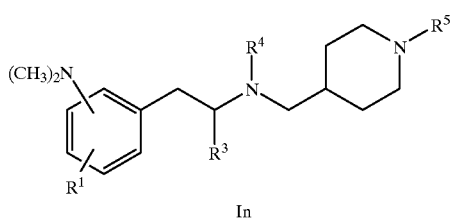

In

A compound of Formula In can be prepared by reacting an aniline compound of Formula Ii with formic acid and formaldehyde under reductive methylation conditions, for example under Eschweiler-Clarke conditions. The reaction proceeds at a temperature of about 50–120° C.

Exemplary preparations of a compound of Formula In, utilizing the reaction conditions described in Scheme P are given in Example 14.

General Utility

Muscarinic receptors mediate the cellular actions of acetylcholine in the central nervous system and in peripheral tissues innervated by the parasympathetic nervous system (Caufield, M. P. *Pharmacol. Ther.* 1993, 58, 319–379). Muscarinic receptors play a key role in regulating smooth muscle function in the lower urogenital, gastrointestinal and respiratory tract (Eglen, R. M. et al. *Pharmacol. Rev.* 1996, 48, 531–565). Accordingly, the muscarinic receptor antagonists, such as those described in the invention, are useful for treating conditions which can be ameliorated by blocking the muscarinic receptors. Such conditions include diseases and disorders associated with altered motility and/or tone of smooth muscle of the gastrointestinal tract, genitourinary tract, and respiratory tract.

Gastrointestinal tract disorders treatable with compounds of this invention specifically include irritable bowel syndrome, diverticular disease, achalasia, gastrointestinal hypermotility disorders, and diarrhea. Genitourinary tract disorders treatable with compounds of this invention specifically include overactive bladder (and its symptoms such as urgency, frequency, and urge incontinence) and stress incontinence. Respiratory tract disorders treatable with compounds of this invention specifically include chronic obstructive pulmonary disease, asthma and pulmonary fibrosis.

Additionally, as muscarinic receptors in the heart play a key role in regulating sinus rhythm, the compounds of the present invention would be expected to be useful in the treatment of various forms of bradyarrythmias including sinus bradycardia. As muscarinic receptors play an important role in mediating synaptic transmission in the central nervous system, the present compounds would also be expected to be useful in the treatment of nervous system disorders including Parkinson's disease, Alzheimer's disease, and motion sickness. Finally, the compounds of the present invention would also be useful in anesthesia, for example as pre-anesthetic medication, and in ophthalmology to produce mydriasis and cycloplegia.

Testing

The compounds of this invention are muscarinic receptor antagonists. The muscarinic receptor affinity of test compounds can be determined by an in vitro receptor binding assay which utilizes a cell membrane preparation from the Chinese hamster ovary cells expressing the recombinant human muscarinic receptors ($m_1$–$m_5$), and is described in more detail in Example 16.

The muscarinic antagonist properties of the test compounds can be identified by an in vivo assay which determines inhibitory activity against muscarinic receptor mediated bladder contraction and saliva secretion in anesthetized rats, and is described in more detail in Example 17.

The muscarinic antagonist properties of the test compounds can be identified by an in vivo assay which determines inhibitory activity against muscarinic receptor mediated bladder contraction and saliva secretion in anesthetized dogs, and is described in more detail in Example 18.

Administration and Pharmaceutical Composition

The invention includes a pharmaceutical composition comprising a compound of the present invention or a pharmaceutically acceptable salt or derivative thereof together with one or more pharmaceutically acceptable carriers, and optionally other therapeutic and/or prophylactic ingredients.

In general, the compounds of this invention will be administered in a therapeutically effective amount by any of the accepted modes of administration for agents that serve similar utilities. Suitable dosage ranges are 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of this invention for a given disease.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is oral using a convenient daily dosage regimen which can be adjusted according to the degree of affliction.

The compounds of the invention, together with a conventional adjuvant, carrier, or diluent, may be placed into the form of pharmaceutical compositions and unit dosages. The pharmaceutical compositions and unit dosage forms may comprise conventional ingredients in conventional proportions, with or without additional active compounds or principles, and the unit dosage forms may contain any suitable effective amount of the active ingredient commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing one (1) milligram of active ingredient or, more broadly, 0.01 to one hundred (100) milligrams, per tablet, are accordingly suitable representative unit dosage forms.

The compounds of the present invention may be formulated in a wide variety of oral administration dosage forms. The pharmaceutical compositions and dosage forms may comprise the compounds of the invention or its pharmaceutically acceptable salt as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid that is a mixture with the finely divided active component. In tablets, the active component is mixed with the carrier having the necessary binding capacity in suitable proportions and compacted in the shape and size desired. The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be, as solid forms, suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion), and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, or stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base, and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth, pastilles comprising the active ingredient in an inert base such as gelatin and glycerin or sucrose and acacia, and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract, and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in Example 15.

EXAMPLES

The following preparations and examples are given to enable those skilled in the art to more clearly understand and to practice the present invention. They should not be considered as limiting the scope of the invention, but merely as being illustrative and representative thereof.

PREPARATION 1

Preparation of a Compound of Formula 7 as Described in Scheme A

A. 5-(2-Methylallyl)-2,3-dihydrobenzofuran

A solution of 5-bromo-2,3-dihydrobenzofuran (50 grams, 0.251 mole), and 1,2-dibromoethane (2.2 ml) in tetrahydrofuran (250 ml) was added dropwise to a stirred suspension of magnesium turnings (7.5 grams, 0.31 gram-atoms) in tetrahydrofuran (50 ml) over a period of 45 minutes. During the addition the reaction temperature was maintained at 30° C. The solution was cooled in an ice-bath and 3-bromo-2-methylpropene was added all at once. After stirring overnight, the reaction was quenched with cold 2% hydrochloric acid and the mixture was extracted with ether. Evaporation of solvent gave 5-(2-methylallyl)-2,3-dihydrobenzofuran as an oil (43.4 grams, 99%). M$^+$ 174.

B. 1-(2,3-Dihydrobenzofuran-5-yl)propan-2-one

A solution of 5-(2-methylallyl)-2,3-dihydrobenzofuran (58 grams, 0.333 mole) and pyridine (27 ml) in methylene chloride (450 ml) and methanol (150 ml) was cooled in a dry ice/acetone bath and a stream of ozone passed through for 1.0 hour. Thiourea (18 grams, 0.24 mole) was added and the mixture was warmed to room temperature. The resultant precipitate was filtered and the mother liquor evaporated to give an oil which was distilled under reduced pressure to give 1-(2,3-dihydrobenzofuran-5-yl)propan-2-one (32 grams, 54%), bp. 110° C. @ 120 mT.

PREPARATION 2

Preparation of a Compound of Formula 4 as Described in Scheme A

The compound of formula 4 is prepared utilizing the procedures described by Nichols et al. J. Med. Chem. 1973, 16, 480–483; J. Med. Chem. 1986, 29, 2009–2015; and J. Med. Chem. 1991, 34, 1662–1668.

A. (S,S)-N-[2-(2,3-Dihydrobenzofuran-5-yl)-1-methylethyl]-1-phenylethylamine hydrochloride (S)-(–)-1-Phenylethylamine (17.5 ml, 0.136 mole) was added to a stirred solution of 1-(2,3-dihydrobenzofuran-5-yl)-propan-2-one (32 grams, 0.18 mole) in benzene (300 ml) and refluxed for 4 hours with water separation. The solution was evaporated to an oil and the resultant imine was dissolved in ethanol (300 ml). Activated Raney nickel catalyst (6 grams) was added and the mixture was hydrogenated at 50 psi for 24 hours. The catalyst was filtered off and the solution was acidified with 1.0 M hydrogen chloride in ether. The salt was filtered and dried to give (S,S)-N-[2-(2,3-dihydrobenzofuran-5-yl)-1-methylethyl]-1-phenylethylamine hydrochloride (26 grams), m.p. 151° C.

B. (S,S)-N-[2-(2,3-Dihydrobenzofuran-5-yl)-1-methylethyl]-N-ethyl-(1-phenylethyl)amine Sodium triacetoxyborohydride (26 grams, 0.123 mole) was added to a suspension of (S,S)-N-[2-(2,3-dihydrobenzofuran-5-yl)-1-methylethyl]-1-phenylethylamine hydrochloride (26 grams, 0.08 mole) in dichloroethane (300 ml) and triethylamine (11.5 ml). After stirring for 5 minutes, acetaldehyde (4.8 ml, 0.086 mole) was added and the mixture was stirred for another 2 hours. Aqueous 5% sodium carbonate (400 ml) was added and the mixture was extracted with methylene chloride. Evaporation of the solvent gave (S,S)-N-[2-(2,3-dihydrobenzofuran-5-yl)-1-methylethyl]-N-ethyl-(1-phenylethyl)amine as an oil (23 grams, 91%), M+ 309.

C. (S)-N-[2-(2,3-Dihydrobenzofuran-5-yl)-1-methylethyl]ethylamine

A mixture of (S,S)-N-[2-(2,3-dihydrobenzofuran-5-yl)-1-methylethyl]-N-ethyl-(1-phenylethyl)amine (23 grams, 0.074 mole) and ammonium formate (30 grams, 0.48 mole) and 10% palladium on carbon (3.7 grams) in ethanol (300 ml) was heated under reflux for 2 hours. The mixture was filtered and the solvent was evaporated to give a residue which was partitioned between 5% sodium hydroxide and ether. Evaporation of the organic phase gave (S)-N-[2-(2,3-dihydrobenzofuran-5-yl)-1-methylethyl]ethylamine as an oil (14 grams, 92%), M+ 205.

PREPARATION 3

An Alternative Preparation of a Compound of formula 4 as Described in Scheme A A. [2-(1-Methyl-2-(3-nitrophenyl)ethyl]ethylamine hydrochloride In dichloromethane (50 ml) was combined 1-(3-nitrophenyl)propan-2-one (1.44 grams, 8 mmole), ethylamine hydrochloride (0.42 grams, 8 mmole), and triethylamine (1.1 ml, 11 mmole). The mixture was stirred under nitrogen at room temperature for 30 minutes. Then sodium triacetoxyborohydride (2.5 grams, 11.7 mmole) was added in one portion. The mixture was stirred under nitrogen 18 hours. Additional ethylamine hydrochloride (0.4 grams) was added. After another 18 hours the mixture was diluted with ethyl ether, washed with 10% sodium hydroxide solution (50 ml), dried over anhydrous magnesium sulfate and the solvent removed under vacuum to give an oil. This oil was taken up into methanol, acidified with 1M hydrochloric acid in ether and the salt was precipitated by further addition of ether. The resulting solid was filtered and air dried to give [2-(1-methyl-2-(3-nitrophenyl)ethyl]ethylamine hydrochloride (1.4 grams, 85%), m.p. 173–175° C., M+H 208.

B. [2-(4-Bromophenyl)-1-methylethyl]ethylamine hydrochloride

A mixture of 1-(4-bromophenyl)propan-2-one (5 grams, 23.5 mmole), ethylamine hydrochloride (19 grams, 0.23 mole) and sodium cyanoborohydride (2.22 grams, 0.035 mole) in methanol (100 ml) was stirred at 22° C. for 16 hours. The mixture was concentrated under reduced pressure and the residue was partitioned between 1.0N sodium hydroxide (25 ml) and ethyl ether (60 ml). The organic phase was dried (anhydrous magnesium sulfate) and concentrated under reduced pressure. The oily base was converted to the hydrochloride salt and recrystallized from ethanol/ethyl ether to give [2-(4-bromophenyl)-1-methylethyl]ethylamine hydrochloride (3.8 grams, 58%), m.p. 175–176° C.

C. Similarly, substituting 1-(4-bromophenyl)propan-2-one or 1-(3-nitrophenyl)propan-2-one with other ketones and optionally replacing ethylamine with other amines, and following the procedures described above in Preparation 3B, the following compounds of formula 4 were prepared:

[2-(2-Fluorophenyl)-1-methylethyl]ethylamine hydrochloride, m.p. 146° C.;

(S)-[2-(4-Chlorophenyl)-1-methylethyl]propylamine hydrochloride, m.p. 184–185° C.;

(R)-[2-(3-Trifluoromethylphenyl)-1-methylethyl] propylamine hydrochloride, m.p. 180–181° C.;

[2-(2,3-Dihydrobenzo[1,4]dioxin-6-yl)-1-methylethyl] propylamine hydrochloride, m.p. 151–152° C.

PREPARATION 4

Preparation of a Compound of Formula 13 as Described in Scheme B

A. 1-(tert-Butoxycarbonyl)piperidine-4-carboxylic acid

To a solution of piperidine-4-carboxylic acid (10 grams, 0.08 mole) in 3N sodium hydroxide (52 ml), water (48 ml), and dioxane (100 ml) was added di-tert-butyl dicarbonate (18.6 grams, 0.085 mole) and magnesium oxide (3.4 grams, 0.084 mole). The mixture was stirred at room temperature for 16 hours. The mixture was filtered and the filtrate was acidified with sodium bisulfate and extracted with dichloromethane. The organic layer was dried over magnesium sulfate and concentrated under reduced pressure to give 1-(tert-butoxycarbonyl)piperidine-4-carboxylic acid as a white solid (17.7 g, 99%).

B. 1-(tert-Butoxycarbonyl)piperidine-4-(N-methoxy-N-methyl)-carboxamide

To a solution of 1-(tert-butoxycarbonyl)piperidine-4-carboxylic acid (17.7 grams, 0.08 mole) in dichloromethane (200 ml) was added N,O-dimethylhydroxylamine hydrochloride (9.2 grams, 0.094 mole), diisopropylethylamine (12.17 grams, 0.094 mole), dicyclohexylcarbodiimide (16.2 grams, 0.079 mole) and dimethylaminopyridine (4.8 grams, 0.048 mole). The mixture was stirred at room temperature for 16 hours. The insoluble solid was removed by filtration, and the filtrate was concentrated under reduced pressure to leave a residue which was purified by flash chromatography on silica gel eluting with 40% ethyl acetate in hexane to give 1-(tert-butoxycarbonyl)piperidine-4-(N-methoxy-N-methyl)-carboxamide as an oil (17.51 grams, 82%), M⁺H 273.

C. 1-(tert-Butoxycarbonyl)piperidine-4-carboxaldehyde

To a cold solution of 1-(tert-butoxycarbonyl)piperidine-4-(N-methoxy-N-methyl)-carboxamide (7.0 grams, 0.026 mole) in dry tetrahydrofuran (50 ml) was added lithium aluminum hydride (2.5 grams, 0.066 mole) in portions at 0° C. The reaction mixture was stirred for 30 minutes then ethyl ether (100 ml) was added followed by 20% citric acid (100 ml). Stirring was continued for another 30 minutes. The organic layer was separated and the aqueous layer was extracted with ethyl ether. The combined organic extract was washed with saturated sodium bicarbonate solution, water, 10% citric acid and water; dried over sodium sulfate and concentrated under reduced pressure to give 1-(tert-butoxycarbonyl)piperidine-4-carboxaldehyde as an oil (5.02 grams, 92%), M⁺H=213.

PREPARATION 5

Preparation of a Compound of Formula 17 as Described in Scheme B

A. 1-Methanesulfonylpiperidine-4-carboxylic acid ethyl ester

A solution of methanesulfonyl chloride (28 ml, 0.36 mole) in dichloromethane (50 ml) was added dropwise to a solution of piperidine-4-carboxylic acid ethyl ester (50 grams, 0.32 mole) and triethylamine (53 ml, 0.38 mole) in dichloromethane (350 ml) at 0° C. The reaction mixture was stirred at 0–5° C. for 3 hours. The solution was washed with 2×100 ml water, dried (anhydrous magnesium sulfate) and concentrated under reduced pressure. The solid residue was triturated with 100 ml ethyl ether, collected by filtration and dried to give 1-methanesulfonylpiperidine-4-carboxylic acid ethyl ester (68 grams, 90%), m.p. 91–92° C.

B. 1-Methanesulfonylpiperidine-4-methanol

A solution of 1.0 M lithium aluminum hydride (200 ml, 0.2 mole) in tetrahydrofuran was added dropwise to a solution of 1-methanesulfonylpiperidine-4-carboxylic acid ethyl ester (68 grams, 0.29 mole) in tetrahydrofuran (500 ml) at about +5° C. The reaction mixture was stirred at 5–10° C. for 15 minutes. Water (10 ml) was added dropwise and the mixture was filtered. The filtrate was concentrated under reduced pressure and triturated with 50% ethyl ether-hexane (100 ml). The resulting white solid was collected and dried to give 1-methanesulfonylpiperidine-4-methanol (46 grams, 82%), m.p. 96–97° C.

C. 1-Methanesulfonylpiperidine-4-carboxaldehyde

A solution of dimethylsulfoxide (39 ml, 0.55 mole) in dichloromethane (300 ml) was added slowly to a solution of oxalyl chloride (22.7 ml, 0.264 mole) in dichloromethane (700 ml) at −60° C. After 10 minutes a solution of 1-methanesulfonylpiperidine-4-methanol (46 grams, 0.238 mole) in dichloromethane (500 ml) was added slowly. After 30 minutes at −60° C., triethylamine (167 ml) was added. The mixture was concentrated under reduced pressure and the residue was partitioned between ethyl acetate (1.2 liters) and water (200 ml). The organic phase was dried (anhydrous magnesium sulfate) and concentrated under reduced pressure. The residue was recrystallized from ethyl acetate/hexane to give 1-methanesulfonylpiperidine-4-carboxaldehyde (34 grams), m.p. 97° C.

D. Similarly, substituting methanesulfonyl chloride with other chlorides, and following the procedures described above in Preparation 5A, the following compounds of formula 17 were prepared:

1-(Morpholine-4-carbonyl)piperidine-4-carboxaldehyde. m.p. 78–79° C.; and 1-(Cyclohexanecarbonyl)piperidine-4-carboxaldehyde. M⁺ 223.

Example 1

Preparation of Compounds of Formula Ia as Described in Scheme C Route (a)

1A. N-[2-(4-Methoxyphenyl)-1-methylethyl]-N-ethyl-(piperidin-4-ylmethyl)amine dihydrochloride hemihydrate To a mixture of N-[2-(4-methoxyphenyl)-1-methylethyl] ethylamine hydrochloride (2.0 grams, 8.71 mole) and sodium carbonate (3.2 grams, 30 mole) in toluene (75 ml) and water (50 ml) was added dropwise to a solution of 1-benzyloxycarbonylpiperidine-4-carbonyl chloride (2.67 grams, 9.5 mmole) in toluene (25 ml). The reaction mixture was stirred at 22° C. for 16 hours. The mixture was diluted with ethyl acetate (100 ml), the organic phase was dried (anhydrous magnesium sulfate) and concentrated under reduced pressure. The residue was subjected to flash column chromatography over silica gel eluting with 30% ethyl acetate in hexane. The N-[2-(4-methoxyphenyl)-1-methylethyl]-N-ethyl-[1-(benzyloxycarbonyl)piperidin-4-ylcarbonyl]amine was obtained as an oil, (3.5 grams, 95%), M⁺H 439.

A mixture of N-[2-(4-methoxyphenyl)-1-methylethyl]-N-ethyl-[1-(benzyloxycarbonyl)piperidin-4-ylcarbonyl]amine (3.5 grams, 8.3 mmole) and 10% palladium on carbon (0.7 grams) in ethanol (40 ml) was hydrogenated at 22° C. and 50 p.s.i. for 2.5 hours. The catalyst was removed by filtration and the filtrate was concentrated under reduced pressure to leave N-[2-(4-methoxyphenyl)-1-methylethyl]-N-ethyl-(piperidin-4-ylcarbonyl)amine as a syrup (2.11 grams, 84%), M⁺H 305.

A solution of lithium aluminum hydride (30 mmole) in tetrahydrofuran (120 ml) was heated under reflux. A solution of N-[2-(4-methoxyphenyl)-1-methylethyl]-N-ethyl-(piperidin-4-ylcarbonyl)amine (7.8 grams, 25.6 mmole) in tetrahydrofuran (40 ml) was added dropwise. After 30 minutes excess water was added at 22° C. The mixture was filtered and the filtrate was concentrated under reduced pressure to give N-[2-(4-methoxyphenyl)-1-methylethyl]-N-ethyl-(piperidin-4-ylmethyl)amine, which was isolated as the hydrochloride salt from acetonitrile (7.0 grams, 75%), m.p. 144–146° C., M⁺H 405.

1B. Similarly, substituting N-[2-(4-methoxyphenyl)-1-methylethyl]ethylamine hydrochloride with (S)-N-[2-(4-methoxyphenyl)-1-methylethyl]ethylamine hydrochloride and following the procedure described above in Example 1A, (S)-N-[2-(4-methoxyphenyl)-1-methylethyl]-N-ethyl-(piperidin-4-ylmethyl)amine, M⁺H 291 was prepared.

Route (b)

1C. (S)-N-[2-(2,3-Dihydrobenzofuran-5-yl)-1-methylethyl]-N-ethyl-(piperidin-4-ylmethyl)amine To a solution of (S)-N-[2-(2,3-dihydrobenzofuran-5-yl)-1-methylethyl]ethylamine (2.38 grams, 11.6 mmol) and 1-(tert-butoxycarbonyl)piperidine-4-carboxaldehyde (2.47 grams, 11.6 mmol) in dichloroethane (20 ml) was added sodium triacetoxyborohydride (3.67 grams,17.4 mmole). The reaction mixture was stirred for 16 hours at room temperature. The solvent was removed under reduced pressure and the residue was partitioned between dichloromethane and saturated sodium bicarbonate solution. The organic layer was washed with water, dried over potassium carbonate and concentrated under reduced pressure to leave a residue, which was purified by flash chromatography on silica gel using 30% ethyl acetate in hexane. Appropriate fractions were combined and concentrated to give (S)-N-[2-(2,3-dihydrobenzofuran-5-yl)-1-methylethyl]-N-ethyl-[1-(tert-butoxycarbonyl)piperidin-4-ylmethyl]amine as a oil (3.78 g, 82%), M⁺H 403.

To (S)-N-[2-(2,3-dihydrobenzofuran-5-yl)-1-methylethyl]-N-ethyl-[1-(tert-butoxycarbonyl)piperidin-4-ylmethyl]amine (3.78 grams, 9.4 mmol) was added 20% trifluoroacetic acid (50 ml) in dichloromethane. The solution was stirred at room temperature for 4 hours. The solution was concentrated under reduced pressure and the residue was partitioned between dichloromethane and 1N sodium hydroxide. The organic layer was washed with water, dried over potassium carbonate and concentrated to give (S)-N-[2-(2,3-dihydrobenzofuran-5-yl)-1-methylethyl]-N-ethyl-(piperidin-4-ylmethyl)amine as an oil (2.42 grams, 85%), M⁺H 303.

Example 2

An Alternative Preparation of a Compound of Formula Ia as Described in Scheme D

2A. N-[2-(4-Methoxyphenyl)-1-methylethyl]-N-propyl-[1-(tert-butoxycarbonyl)piperidin-4-ylmethyl]amine A solution of sodium cyanoborohydride (1.07 grams, 17 mmole), 4-aminomethyl-1-(tert-butoxycarbonyl)piperidine (3.0 grams, 14.3 mole) and 1-(4-methoxyphenyl)propan-2-one (2.35 grams, 14.31 mmole) in methanol (50 ml) was stirred at 22° C. for 17 hours. The mixture was concentrated under reduced pressure and the residue was partitioned between ethyl acetate and water. The dried (anhydrous magnesium sulfate) organic phase was concentrated under reduced pressure to leave N-[2-(4-methoxyphenyl)-1-methylethyl]-[1-(tert-butoxycarbonyl)piperidin-4-ylmethyl] amine as an oil (4.28 grams, 82%); hydrochloride, m.p. 198–199° C. (methanol/ethyl ether), M⁺H 391.

A mixture of N-[2-(4-methoxyphenyl)-1-methylethyl]-[1-(tert-butoxycarbonyl)piperidin-4-ylmethyl]amine (0.87 grams, 2.4 mmole), propionaldehyde (0.2 ml, 2.5 mmole) and sodium triacetoxyborohydride (0.763 grams, 3.6 mmole) in 1,2-dichloroethane (25 ml) was stirred at 22° C. for 16 hours. The mixture was concentrated under reduced pressure and the residue was partitioned between 100 ml ethyl ether and 25 ml 10% aqueous sodium carbonate. The dried (anhydrous magnesium sulfate) and concentrated organic phase was subjected to flash chromatography over silica gel 230–400 mesh eluting with 10% ethyl acetate/hexane. Product fractions were concentrated under reduced pressure to give N-[2-(4-methoxyphenyl)- 1-methylethyl]-N-propyl-(1-tert-butoxycarbonylpiperidin-4-ylmethyl) amine as a syrup (0.93 grams, 95%), M⁺H 405.

2B. Similarly, substituting propionaldehyde with acetaldehyde and following the procedure described above in Example 2A, N-[2-(4-methoxyphenyl)-1-methylethyl]-N-ethyl-[1-(tert-butoxycarbonyl)piperidin-4-ylmethyl]amine was prepared.

Example 3

Preparation of Compounds of Formula Ib as Described in Scheme E Route (a)

3A. N-[2-(4-Fluorophenyl)-1-methylethyl]-N-ethyl-[1-(cyclohexanecarbonyl)piperidin-4-ylmethyl]amine dibenzoyl-L-tartrate hemihydrate A mixture of N-[2-(4-fluorophenyl)-1-methylethyl] ethylamine (0.5 grams, 2.76 mmole), 1-(cyclohexanecarbonyl)piperidine-4-carboxaldehyde (0.616 grams, 2.76 mmole) and sodium triacetoxyborohydride (0.88 grams, 4.15 mmole) in 1,2-dichloroethane (20 ml) was stirred for 16 hours. The solution was concentrated under reduced pressure and the residue was partitioned between 1.0N sodium hydroxide (20 ml) and ethyl acetate (50 ml). The organic phase was dried (anhydrous magnesium sulfate) and concentrated under reduced pressure. The product was obtained as the dibenzoyl-L-tartrate salt from ethyl ether to give N-[2-(4-fluorophenyl)-1-methylethyl]-N-ethyl-[1-(cyclohexanecarbonyl)piperidin-4-ylmethyl]amine dibenzoyl-L-tartrate hemihydrate (1.9 grams, 92%), m.p. 121–12° C.

3B. Similarly, substituting N-[2-(4-fluorophenyl)-1-methylethyl]ethylamine with other compounds of formula 4, optionally substituting 1-(cyclohexanecarbonyl)piperidine-4-carboxaldehyde with other compounds of formula 23, and following the procedures described above in Example 3A, the following compounds of Formula Ib were prepared:

N-[2-(3-Phenoxyphenyl)-1-methylethyl]-N-ethyl-[1-(cyclohexanecarbonyl)piperidin-4-ylmethyl]amine hydrochloride, M⁺H 463;

N-[2-(4-Methoxyphenyl)-1-methylethyl]-N-butyl-[1-(cyclohexanecarbonyl)piperidin-4-ylmethyl]amine hydrochloride, M⁺H 429;

N-[2-(3,4-Dichlorophenyl)-1-methylethyl]-N-ethyl-[1-(cyclohexanecarbonyl)piperidin-4-ylmethyl]amine dibenzoyl-L-tartrate hemihydrate, M⁺H 439;

N-[2-(3-Chlorophenyl)-1-methylethyl]-N-ethyl-[1-(cyclohexanecarbonyl)piperidin-4-ylmethyl]amine dibenzoyl-L-tartrate hemihydrate, M⁺H 405;

N-[2-(4-Trifluoromethylphenyl)-1-methylethyl]-N-ethyl-[1-(cyclohexanecarbonyl)piperidin-4-ylmethyl]amine dibenzoyl-L-tartrate hemihydrate, M⁺H 439;

N-[2-(2,3-Dihydrobenzo[1,4]dioxin-6-yl)-1-methylethyl]-N-ethyl-[1-(cyclohexanecarbonyl) piperidin-4-ylmethyl]amine hydrochloride, M⁺H 429;

N-[2-(4-Methoxyphenyl)-1-methylethyl]-N-ethyl-[1-(morpholine-4-carbonyl)piperidin-4-ylmethyl]amine dibenzoyl-L-tartrate hemihydrate, M⁺H 404;

N-{2-[4-(2,2,2-Trifluoroethoxy)phenyl]-1-methylethyl}-N-propyl-[1-(cyclohexanecarbonyl)piperidin-4-ylmethyl]amine dibenzoyl-L-tartrate hemihydrate, M⁺H 483;

N-{2-[4-(2,2,2-Trifluoroethoxy)phenyl]-1-methylethyl}-N-ethyl-[1-(cyclohexanecarbonyl)piperidin-4-ylmethyl]amine dibenzoyl-L-tartrate hemihydrate, M⁺H 483;

N-[2-(4-Phenoxyphenyl)-1-methylethyl]-N-ethyl-[1-(cyclohexanecarbonyl)piperidin-4-ylmethyl]amine dibenzoyl-L-tartrate hemihydrate, M⁺H 463;

N-[2-(2,3-Dihydrobenzo[1,4]dioxin-6-yl)-1-methylethyl]-N-ethyl-[1-(morpholine-4-carbonyl) piperidin-4-ylmethyl]amine hydrochloride, M⁺H 432;

N-[2-(3-Trifluoromethylphenyl)-1-methylethyl]-N-ethyl-[1-(morpholine-4-carbonyl)piperidin-4-ylmethyl] amine hydrochloride, M⁺H 442;

N-[2-(3-Chlorophenyl)-1-methylethyl]-N-ethyl-[1-(morpholine-4-carbonyl)piperidin-4-ylmethyl]amine hydrochloride, M⁺H 408;

N-[2-(3-Chlorophenyl)-1-methylethyl]-N-cyclopropylmethyl-[1-(morpholine-4-carbonyl) piperidin-4-ylmethyl)amine hydrochloride, M⁺H 434;

N-[2-(3-Nitrophenyl)-1-methylethyl]-N-propyl-[1-(morpholine-4-carbonyl)piperidin-4-ylmethyl]amine hydrochloride, M⁺H 419;

N-[2-(3-Aminophenyl)-1-methylethyl]-N-propyl-[1-(morpholine-4-carbonyl)piperidin-4-ylmethyl]amine dihydrochloride, M+H 403;

N-[2-(3-Trifluoromethylphenyl)-1-methylethyl]-N-propyl-[1-(morpholine-4-carbonyl)piperidin-4-ylmethyl]amine hydrochloride, M+H 456;

N-[2-(2,3-Dihydrobenzofuran-6-yl)-1-methylethyl]-N-ethyl-[1-(morpholine-4-carbonyl)piperidin-4-ylmethyl]amine hydrochloride, M+H 416;

N-[2-(2,3-Dihydrobenzofuran-6-yl)-1-methylethyl]-N-propyl-[1-(morpholine-4-carbonyl)piperidin-4-ylmethyl]amine hydrochloride, M+H 430;

N-[2-(2,3-Dihydrobenzofuran-5-yl)-1-methylethyl]-N-ethyl-[1-(morpholine-4-carbonyl)piperidin-4-ylmethyl]amine hydrochloride, M+H 416;

(S)-N-[2-(2,3-Dihydrobenzofuran-5-yl)-1-methylethyl]-N-ethyl-[1-(morpholine-4-carbonyl)piperidin-4-ylmethyl]amine hydrochloride, $[\alpha]_D^{25}$ +15° (c 1.0 CHCl$_3$), M+H 416;

N-[2-(2,3-Dihydrobenzofuran-5-yl)-1-methylethyl]-N-propyl-[1-(morpholine-4-carbonyl)piperidin-4-ylmethyl]amine hydrochloride, M+H 429;

N-[2-(3-Oxo-4H-benzo[1,4]oxazin-6-yl)-1-methylethyl]-N-propyl-[1-(morpholine-4-carbonyl)piperidin-4-ylmethyl]amine hydrochloride, M+H 459;

N-[2-(4-Nitrophenyl)-1-methylethyl]-N-propyl-[1-(morpholine-4-carbonyl)piperidin-4-ylmethyl]amine, M+H 433;

(S)-N-[2-(3-Nitrophenyl)-1-methylethyl]-N-ethyl-[1-(morpholine-4-carbonyl)piperidin-4-ylmethyl]amine hydrochloride, M+H 419;

N-[2-(3,3-Dimethyl-2,3-dihydrobenzofuran-6-yl)-1-methylethyl]-N-ethyl-[1-(morpholine-4-carbonyl)piperidin-4-ylmethyl]amine hydrochloride, m.p. 203–204° C.; and (S)-N-[2-(2,2-Dimethyl-2,3-dihydrobenzofuran-5-yl)-1-methylethyl]-N-ethyl-[1-(morpholine-4-carbonyl)piperidin-4-ylmethyl]amine hydrochloride, M+H 444.

Route (b)

3C. N-[2-(4-methoxyphenyl)-1-methylethyl]-N-ethyl-[1-(cyclohexanecarbonyl)piperidin-4-ylmethyl]amine di-p-toluyl-L-tartrate hydrate A solution of N-[2-(4-methoxyphenyl)-1-methylethyl]-N-ethyl-[1-(tert-butyloxycarbonyl)-piperidin-4-ylmethyl]amine (0.28 grams, 0.72 mmole) in trifluoroacetic acid (5 ml) was concentrated under reduced pressure. The residue was mixed with 10% aqueous sodium carbonate (15 ml), toluene (10 ml) and cyclohexanecarbonyl chloride (0.134 ml, 1.0 mmole). The mixture was reacted at 22° C. for 15 hours and extracted with ethyl acetate (25 ml). The organic phase was dried (anhydrous magnesium sulfate) and concentrated under reduced pressure. The product was isolated as the di-p-toluyl-L-tartrate salt to give N-[2-(4-methoxyphenyl)-1-methylethyl]-N-ethyl-1-(cyclohexanecarbonyl)piperidin-4-ylmethyl]amine di-p-toluyl-L-tartrate hydrate (0.29 grams, 51%), m.p. 119–120° C., M+H 401.

3D. (S)-N-[2-(4-methoxyphenyl)-1-methylethyl]-N-ethyl-[1-(cyclohexanecarbonyl)piperidin-4-ylmethyl]amine hydrochloride To a mixture of (S)-N-[2-(4-methoxyphenyl)-1-methylethyl]-N-ethyl-(piperidin-4-ylmethyl)amine (1.54 grams, 5.3 mmole) and sodium carbonate (1.6 grams, 15 mmole) in toluene (50 ml) and water (30 ml) was added cyclohexanecarbonyl chloride (0.74 ml, 5.5 mmole). After 16 hours the reaction mixture was extracted with ethyl acetate (100 ml), the organic phase was dried (anhydrous magnesium sulfate) and concentrated under reduced pressure. The product was isolated as the hydrochloride salt from ethyl acetate/ethyl ether to give (S)-N-[2-(4-methoxyphenyl)-1-methylethyl]-N-ethyl-[1-(cyclohexanecarbonyl)piperidin-4-ylmethyl]amine hydrochloride (1.25 grams, 54%), m.p. 159–160° C.

3E. Similarly, substituting (S)-N-[2-(4-methoxyphenyl)-1-methylethyl]-N-ethyl-(piperidin-4-ylmethyl)amine with other compounds of Formula Ia, optionally substituting cyclohexanecarbonyl chloride with other carbonyl chlorides, and following the procedures described above in Example 3D, the following compounds of Formula Ib were prepared:

N-[2-(4-Methoxyphenyl)-1-methylethyl]-N-ethyl-(1-isobutyrylpiperidin-4-ylmethyl)amine dibenzoyl-L-tartrate hydrate, m.p. 119–120° C. (ethyl ether);

N-[2-(4-Methoxyphenyl)-1-methylethyl]-N-ethyl-[1-(cyclopentanecarbonyl)piperidin-4-ylmethyl]amine dibenzoyl-L-tartrate hemihydrate, m.p. 121–123° C. (ethyl ether);

N-[2-(4-Methoxyphenyl)-1-methylethyl]-N-ethyl-[1-(tetrahydropyran-4-carbonyl)piperidin-4-ylmethyl]amine dibenzoyl-L-tartrate hemihydrate, m.p. 116–118° C. (ethyl ether);

N-[2-(4-Methoxyphenyl)-1-methylethyl]-N-ethyl-(1-acetylpiperidin-4-ylmethyl)amine dibenzoyl-L-tartrate hemihydrate, m.p. 114–115° C. (ethyl ether);

N-(2-(4-Methoxyphenyl)-1-methylethyl]-N-ethyl-[1-(diphenylmethylcarbonyl)piperidin-4-ylmethyl]amine dibenzoyl-L-tartrate hydrate, M+H 485;

N-[2-(3-Trifluoromethylphenyl)-1-methylethyl]-N-ethyl-[1-(cyclohexanecarbonyl)piperidin-4-ylmethyl]amine dibenzoyl-L-tartrate hydrate, M+H 439;

N-[2-(2,3-Dihydrobenzo[1,4]dioxin-6-yl)-1-methylethyl]-N-ethyl-[1-(tetrahydropyran-4-carbonyl)piperidin-4-ylmethyl]amine hydrochloride, M+H 431;

N-[2-(2,3-Dihydrobenzo[1,4]dioxin-6-yl)-1-methylethyl]-N-ethyl-[1-(tetrahydropyran-4-carbonyl)piperidin-4-ylmethyl]amine dibenzoyl-L-tartrate hydrate, M+H 431;

N-[2-(3-Trifluoromethylphenyl)-1-methylethyl]-N-ethyl-[1-(tetrahydropyran-4-carbonyl)piperidin-4-ylmethyl]amine hydrochloride, M+H 441;

N-[2-(3-Chlorophenyl)-1-methylethyl]-N-ethyl-[1-(tetrahydropyran-4-carbonyl)piperidin-4-ylmethyl)amine hydrochloride, M+H 407;

N-[2-(2,3-Dihydrobenzofuran-6-yl)-1-methylethyl]-N-cyclopropylmethyl-[1-(tetrahydropyran-4-carbonyl)piperidin-4-ylmethyl)amine hydrochloride, M+H 442;

N-[2-(2,3-Dihydrobenzofuran-5-yl)-1-methylethyl]-N-cyclopropylmethyl-[1-(tetrahydropyran-4-carbonyl)piperidin-4-ylmethyl)amine hydrochloride, M+H 442;

N-[2-(4-Nitrophenyl)-1-methylethyl]-N-propyl-[1-(tert-butoxycarbonyl)piperidin-4-ylmethyl]amine hydrochloride, M+H 420;

N-[2-(4-Nitrophenyl)-1-methylethyl]-N-propyl-[1-(piperidine-4-carbonyl)piperidin-4-ylmethyl]amine dihydrochloride, M+H 431;

N-[2-(4-Nitrophenyl)-1-methylethyl]-N-propyl-[1-(1-trifluoroacetylpyridine-4-carbonyl)piperidin-4-ylmethyl]amine dihydrochloride, M+H 527;

N-[2-(2,3-Dihydrobenzofuran-5-yl)-1-methylethyl]-N-ethyl-[1-(2-hydroxy-1-phenylcarbonyl)piperidin-4-ylmethyl]amine trifluoroacetate, M$^+$H 451;

N-{2-[3-(4-tert-Butylphenylcarbonylamino)phenyl]-1-methylethyl}-N-propyl-[1-(4-methanesulfonylphenylcarbonyl)piperidin-4-ylmethyl)amine hydrochloride, M$^+$H 632;

N-{2-[3-(4-tert-Butylphenylcarbonylamino)phenyl]-1-methylethyl}-N-propyl-[1-(furan-2-carbonyl)piperidin-4-ylmethyl)amine trifluoroacetate, M$^+$H 544;

N-{2-[3-(4-tert-Butylphenylcarbonylamino)phenyl]-1-methylethyl}-N-propyl-[1-(ethoxydicarbonyl)piperidin-4-ylmethyl)amine trifluoroacetate, M$^+$H 550;

N-{2-[3-(4-tert-Butylphenylcarbonylamino)phenyl]-1-methylethyl}-N-propyl-[1-(pyridine-4-carbonyl)piperidin-4-ylmethyl)amine trifluoroacetate, M$^+$H 555;

N-{2-[3-(4-tert-Butylphenylcarbonylamino)phenyl]-1-methylethyl}-N-propyl-[1-(tert-butylcarbonyl)piperidin-4-ylmethyl)amine trifluoroacetate, M$^+$H 534;

N-{2-[3-(4-tert-Butylphenylcarbonylamino)phenyl]-1-methylethyl}-N-propyl-[1-(cyclohexylcarbonyl)piperidin-4-ylmethyl)amine trifluoroacetate, M$^+$H 560;

N-{2-[3-(4-tert-Butylphenylcarbonylamino)phenyl]-1-methylethyl}-N-propyl-[1-(pyridine-3-carbonyl)piperidin-4-ylmethyl)amine trifluoroacetate, M$^+$H 555;

N-{2-[3-(4-tert-Butylphenylcarbonylamino)phenyl]-1-methylethyl}-N-propyl-[1-acetylpiperidin-4-ylmethyl)amine trifluoroacetate, M$^+$H 492;

N-{2-[3-(4-tert-Butylphenylcarbonylamino)phenyl]-1-methylethyl}-N-propyl-[1-(ethylcarbonyl)piperidin-4-ylmethyl)amine trifluoroacetate, M$^+$H 506;

N-{2-[3-(4-tert-Butylphenylcarbonylamino)phenyl]-1-methylethyl}-N-propyl-[1-(2-methylphenylcarbonyl)piperidin-4-ylmethyl)amine trifluoroacetate, M$^+$H 568;

N-{2-[3-(4-tert-Butylphenylcarbonylamino)phenyl]-1-methylethyl}-N-propyl-[1-(cyclobutylcarbonyl)piperidin-4-ylmethyl)amine trifluoroacetate, M$^+$H 532;

N-{2-[3-(4-tert-Butylphenylcarbonylamino)phenyl]-1-methylethyl}-N-propyl-[1-(4-cyanophenylcarbonyl)piperidin-4-ylmethyl)amine trifluoroacetate, M$^+$H 579;

N-{2-[3-(4-tert-Butylphenylcarbonylamino)phenyl]-1-methylethyl}-N-propyl-[1-(isobutylcarbonyl)piperidin-4-ylmethyl)amine trifluoroacetate, M$^+$H 534; and N-{2-[3-(4-tert-Butylphenylcarbonylamino)phenyl]-1-methylethyl}-N-propyl-[1-(isoxazole-5-carbonyl)piperidin-4-ylmethyl)amine trifluoroacetate, M$^+$H 545.

Example 4

Preparation of Compounds of Formula Ic as Described in Route (a)

4A. N-[2-(4-Methoxyphenyl-1-methylethyl]-N-ethyl-[1-(pyrrolidine-1-carbonyl)piperidin-4-ylmethyl]amine dibenzoyl-L-tartrate hydrate To a solution of 2 M phosgene/toluene (2.0 ml, 4 mmole) in ethyl ether (20 ml) was added a solution of N-[2-(4-methoxyphenyl-1-methylethyl]-N-ethyl-(piperidin-4-ylmethyl)amine (0.23 grams, 0.79 mmole) in ethyl ether (30 ml). After 30 minutes the precipitate was collected by filtration and dried in vacuo to give N-[2-(4-methoxyphenyl-1-methylethyl]-N-ethyl-(1-chlorocarbonylpiperidin-4-ylmethyl)amine hydrochloride (0.238 grams, 77%), m.p. 144–145° C.

To a suspension of N-[2-(4-methoxyphenyl)-1-methylethyl]-N-ethyl-(1-chlorocarbonylpiperidin-4-ylmethyl)amine hydrochloride (0.1 grams, 0.257 mmole) in ethyl ether (10 ml) was added pyrrolidine (0.1 ml, 1.2 mmole). The mixture was stirred at 22° C. for 15 hours. The mixture was shaken with 10% aqueous sodium carbonate (10 ml), the organic phase was dried (anhydrous magnesium sulfate) and concentrated under reduced pressure. The residue was subjected to flash column chromatography over silica gel eluting with ethyl acetate. The product was isolated as the dibenzoyl-L-tartrate from ethyl ether to give N-[2-(4-methoxyphenyl)-1-methylethyl]-N-ethyl-[1-(pyrrolidine-1-carbonyl)piperidin-4-ylmethyl]amine dibenzoyl-L-tartrate hydrate (0.087 gram, 45%), m.p. 110–112° C.

4B. Similarly, substituting N-[2-(4-methoxyphenyl)-1-methylethyl]-N-ethyl-(piperidin-4-ylmethyl)amine with other compounds of Formula Ia, optionally substituting pyrrolidine with other amines, and following the procedures described above in Example 4A, the following compounds of Formula Ic were prepared:

(S)-N-[2-(4-Methoxyphenyl)-1-methylethyl]-N-ethyl-[1-(3-hydroxypyrrolidine-1-carbonyl)piperidin-4-ylmethyl]amine dibenzoyl-L-tartrate hydrate, m.p. 101–102° C.;

N-[2-(4-Methoxyphenyl)-1-methylethyl]-N-ethyl-[1-(4-tert-butoxycarbonylpiperazine-1-carbonyl)piperidin-4-ylmethyl]amine dibenzoyl-L-tartrate hydrate, m.p. 108–109° C., M$^+$H 503;

N-[2-(3-Trifluoromethylphenyl]-1-methylethyl]-N-ethyl-[1-(2-hydroxymethylpiperidine-1-carbonyl)piperidin-4-ylmethyl]amine hydrochloride, M$^+$H 470; and (S)-N-[2-(3-Chlorophenyl)-1-methylethyl]-N-ethyl-[1-(pyrrolidine-1-carbonyl)piperidin-4-ylmethyl]amine hydrochloride, M$^+$H 392.

Route (b)

4C. N-[2-(4-Methoxyphenyl)-1-methylethyl]-N-ethyl-[1-(diisopropylaminocarbonyl)piperidin-4-ylmethyl]amine dibenzoyl-L-tartrate hemihydrate A solution of N-[2-(4-methoxyphenyl)-1-methylethyl]-N-ethyl-(piperidin-4-ylmethyl)amine hydrochloride (0.205 grams, 0.564 mmole), triethylamine (0.5 ml, 3.6 mmole) and diisopropylcarbamyl chloride (0.115 grams, 0.7 mmole) in dichloromethane (25 ml) was stirred at 22° C. for 15 hours. The residue obtained upon concentration under reduced pressure was partitioned between 5% aqueous sodium carbonate and ethyl ether. The free base obtained from the dried (anhydrous magnesium sulfate) and concentrated organic phase was converted to the dibenzoyl-L-tartrate salt to give N-[2-(4-methoxyphenyl)-1-methylethyl]-N-ethyl-[1-(diisopropylaminocarbonyl)piperidin-4-ylmethyl]amine dibenzoyl-L-tartrate hemihydrate (0.3 grams, 69%), mp. 105–106° C.

4D. Similarly, substituting N-[2-(4-methoxyphenyl)-1-methylethyl]-N-ethyl-(piperidin-4-ylmethyl)amine with other compounds of Formula Ia, optionally substituting diisopropyl carbamyl chloride with other carbamyl chlorides, and following the procedures described above in Example 4C, the following compounds of Formula Ic were prepared:

N-[2-(4-Methoxyphenyl)-1-methylethyl]-N-ethyl-[1-(dimethylaminocarbonyl)piperidin-4-ylmethyl]amine hydrochloride, M$^+$H 362;

N-[2-(4-Methoxyphenyl)-1-methylethyl]-N-ethyl-[1-(dimethylaminocarbonyl)piperidin-4-ylmethyl]amine dibenzoyl-L-tartrate hemihydrate, M$^+$H 362;

N-[2-(4-Methoxyphenyl)-1-methylethyl]-N-ethyl-(1-propanoylpiperidin-4-ylmethyl)amine dibenzoyl-L-tartrate, m.p. 106–107° C., M$^+$H 347;

N-[2-(4-Methoxyphenyl)-1-methylethyl]-N-ethyl-[1-(isopropylaminocarbonyl)piperidin-4-ylmethyl]amine, m.p. 123–124° C.;

N-[2-(3-Trifluoromethylphenyl)-1-methylethyl]-N-ethyl-[1-(dimethylaminocarbonyl)piperidin-4-ylmethyl]amine dibenzoyl-L-tartrate, M$^+$H 400;

N-[2-(4-Methoxyphenyl)-1-methylethyl]-N-ethyl-[1-(diethylaminocarbonyl)piperidin-4-ylmethyl]amine hydrochloride, m.p. 68–70° C.;

N-[2-(2,3-Dihydrobenzo[1,4]dioxin-6-yl)-1-methylethyl]-N-ethyl-[1-(diethylaminocarbonyl)piperidin-4-ylmethyl)amine hydrochloride, M$^+$H 418;

N-[2-(2,3-Dihydrobenzo[1,4]dioxin-6-yl)-1-methylethyl]-N-ethyl-[1-(dimethylaminocarbonyl)piperidin-4-ylmethyl]amine hydrochloride, M$^+$H 390;

N-{2-[4-(2,2,2-Trifluoroethoxy)phenyl]-1-methylethyl}-N-propyl-[1-(dimethylaminocarbonyl)piperidin-4-ylmethyl]amine dibenzoyl-L-tartrate, M$^+$H 444;

N-{2-[4-(2,2,2-Trifluoroethoxy)phenyl]-1-methylethyl}-N-ethyl-[1-(dimethylaminocarbonyl)piperidin-4-ylmethyl]amine dibenzoyl-L-tartrate, M$^+$H 430;

N-[2-(4-Methoxyphenyl)-1-methylethyl]-N-propyl-[1-(dimethylaminocarbonyl)piperidin-4-ylmethyl]amine dibenzoyl-L-tartrate, m.p. 109–110° C.;

N-[2-(3-Trifluoromethylphenyl)-1-methylethyl]-N-ethyl-[1-(piperidine-1-carbonyl)piperidin-4-ylmethyl]amine hydrochloride, M$^+$H 440;

N-[2-(3-Trifluoromethylphenyl)-1-methylethyl]-N-ethyl-[1-(piperidine-1-carbonyl)piperidin-4-ylmethyl]amine dibenzoyl-L-tartrate, M$^+$H 440;

N-[2-(3-Chloromethylphenyl)-1-methylethyl]-N-ethyl-[1-(dimethylaminocarbonyl)piperidin-4-ylmethyl]amine dibenzoyl-L-tartrate, M$^+$H 366;

N-[2-(4-Trifluoromethylphenyl)-1-methylethyl]-N-ethyl-[1-(piperidine-1-carbonyl)piperidin-4-ylmethyl]amine dibenzoyl-L-tartrate, M$^+$H 440;

N-[2-(4-Trifluoromethylphenyl)-1-methylethyl]-N-ethyl-[1-(dimethylaminocarbonyl)piperidin-4-ylmethyl]amine dibenzoyl-L-tartrate, M$^+$H 400;

N-[2-(4-Methoxyphenyl)-1-methylethyl]-N-ethyl-[1-(tert-butylaminocarbony)piperidin-4-ylmethyl]amine, m.p. 96–97° C.;

N-[2-(3-Trifluoromethylphenyl)-1-methylethyl]-N-ethyl-[1-(pyridine-3-methylaminocarbonyl)piperidin-4-ylmethyl]amine dihydrochloride, M$^+$H 463;

N-[2-(3-Trifluoromethylphenyl)-1-methylethyl]-N-ethyl-[1-(1,2,3,4-tetrahydro[1,5]naphthyridine-1-carbonyl)piperidin-4-ylmethyl]amine dihydrochloride, M$^+$H 486;

N-[2-(3-Chlorophenyl)-1-methylethyl]-N-ethyl-[1-(piperidine-1-carbonyl)piperidin-4-ylmethyl]amine hydrochloride, M$^+$H 406;

N-[2-(3-Trifluoromethylphenyl)-1-methylethyl]-N-ethyl-[1-(1,2,3,4-tetrahydroquinoline-1-carbonyl)piperidin-4-ylmethyl]amine hydrochloride, M$^+$H 488;

N-[2-(3-Trifluoromethylphenyl)-1-methylethyl]-N-ethyl-[1-(3,4-dihydroquinoline-2H-benzo[1,4]oxazine-4-carbonyl)piperidin-4-ylmethyl]amine hydrochloride, M$^+$H 490; and N-[2-(3-Trifluoromethylphenyl) 1-methylethyl]-N-ethyl-[1-(2-methylcarboxylpiperidine-1-carbonyl)piperidin-4-ylmethyl]amine hydrochloride, M$^+$H 498;

N-{2-[3-(4-tert-Butylphenylcarbonylamino)phenyl]-1-methylethyl}-N-propyl-[1-(4-methylpiperazine-1-carbonyl)piperidin-4-ylmethyl]amine dihydrochloride, m.p. 182–183° C., M$^+$H 576;

N-{2-[3-(4-tert-Butylphenylcarbonylamino)phenyl]-1-methylethyl}-N-propyl-[1-thiomorpholine-4-carbonyl)piperidin-4-ylmethyl]amine hydrochloride, m.p. 137–138° C., M$^+$H 579;

N-{2-[3-(4-tert-Butylphenylcarbonylamino)phenyl]-1-methylethyl}-N-propyl-[1-(diethylaminocarbonyl)piperidin-4-ylmethyl)amine trifluoroacetate, M$^+$H 549;

N-{2-[3-(4-tert-Butylphenylcarbonylamino)phenyl]-1-methylethyl}-N-propyl-[1-(dimethylaminocarbonyl)piperidin-4-ylmethyl)amine trifluoroacetate, M$^+$H 521;

N-{2-[3-(4-tert-Butylphenylcarbonylamino)phenyl]-1-methylethyl}-N-propyl-[1-(diisopropylaminocarbonyl)piperidin-4-ylmethyl)amine trifluoroacetate, M$^+$H 577; and N-{2-[3-(4-tert-Butylphenylcarbonylamino)phenyl]-1-methylethyl}-N-propyl-[1-(phenylaminocarbonyl)piperidin-4-ylmethyl)amine trifluoroacetate, M$^+$H 569.

Route (c)

4E. N-[2-(4-Methoxyphenyl)-1-methylethyl]-N-ethyl-[1-(methylaminocarbonyl)piperidin-4-ylmethyl]amine To a solution of N-[2-(4-methoxyphenyl)-1-methylethyl]-N-ethyl-(piperidin-4-ylmethyl)amine (0.23 grams, 0.79 mmole) in ethyl ether (10 ml) was added methyl isocyanate (0.2 ml, 3.4 mmole). After 1.0 hour at 22° C., the solution was concentrated under reduced pressure and the residue was recrystallized from ethyl ether/hexane to give N-[2-(4-methoxyphenyl)-1-methylethyl]-N-ethyl-[1-(methylaminocarbonyl)piperidin-4-ylmethyl]amine (0.249 grams, 91%) m.p. 97–98° C.

4F. Similarly, substituting N-[2-(4-methoxyphenyl)-1-methylethyl]-N-ethyl-(piperidin-4-ylmethyl)amine with other compounds of Formula Ia, optionally substituting methyl isocyanate with other isocyanates, and following the procedures described above in Example 4E, the following compounds of Formula Ic were prepared:

N-[2-(3-Chlorophenyl)-1-methylethyl]-N-ethyl-[1-(isopropylaminocarbonyl)piperidin-4-ylmethyl]amine dibenzoyl-L-tartrate, M$^+$H 380;

N-[2-(3-Chlorophenyl)-1-methylethyl]-N-ethyl-[1-(cyclohexylaminocarbonyl)piperidin-4-ylmethyl]amine dibenzoyl-L-tartrate, M$^+$H 420;

N-[2-(4-Methoxyphenyl)-1-methylethyl]-N-ethyl-[1-(methylaminothiocarbonyl)piperidin-4-ylmethyl]amine dibenzoyl-L-tartrate, M$^+$H 364;

N-{2-[3-(4-tert-Butylphenylcarbonylamino)phenyl]-1-methylethyl}-N-propyl-[1-(tert-butylaminocarbonyl)piperidin-4-ylmethyl]amine, m.p. 155–160° C., M$^+$H 549;

N-{2-[3-(4-tert-Butylphenylcarbonylamino)phenyl]-1-methylethyl}-N-propyl-[1-(tert-butylaminocarbonyl)piperidin-4-ylmethyl)amine trifluoroacetate, M$^+$H 549;

N-{2-[3-(4-tert-Butylphenylcarbonylamino)phenyl]-1-methylethyl}-N-propyl-[1-(isopropylaminocarbonyl)piperidin-4-ylmethyl)amine trifluoroacetate, M$^+$H 535; and N-{2-[3-(4-tert-Butylphenylcarbonylamino)phenyl]-1-methylethyl}-N-propyl-[1-(methylaminocarbonyl)piperidin-4-ylmethyl)amine trifluoroacetate, M$^+$H 507.

Route (d)

4G. N-[2-(4-Methoxyphenyl)-1-methylethyl]-N-ethyl-(1-aminocarbonylpiperidin-4-ylmethyl)amine A mixture of N-[2-(4-methoxyphenyl)-1-methylethyl]-N-ethyl-(piperidin-4-ylmethyl)amine hydrochloride (0.42 grams, 1.16 mmole) and potassium cyanate (1.5 grams, 18.5 mmole) in water (5 ml) was heated under reflux for about 20 minutes. The white solid which formed upon cooling was collected and recrystallized from chloroform/hexane to give N-[2-(4-methoxyphenyl)-1-methylethyl]-N-ethyl-(1-aminocarbonylpiperidin-4-ylmethyl)amine (0.3 grams, 77%), m.p. 104–10° C.

4H. N-[2-(4-Methoxyphenyl)-1-methylethyl]-N-ethyl-[1-(4-acetylpiperazine-1-carbonyl)piperidin-4-ylmethyl]amine dibenzoyl-L-tartrate hydrate A solution of N-[2-(4-methoxyphenyl)-1-methylethyl]-N-ethyl-[1-(4-tert-butoxycarbonylpiperazin-1-ylcarbonyl)piperidin-4-ylmethyl]amine (0.325 grams, 0.65 mmole) in trifluoroacetic acid (2.0 ml) was kept at 22° C. for 45 minutes. The solution was concentrated under reduced pressure, the residue was partitioned between 1N sodium hydroxide and ethyl ether. The dried (anhydrous magnesium sulfate) organic phase was concentrated under reduced pressure. The residue was dissolved in a mixture of pyridine (5 ml) and acetic anhydride (1.0 ml) and the solution was kept at 22° C. for 15 hours. The solution was concentrated under reduced pressure and the residue was partitioned between 0.5N sodium hydroxide and ethyl ether. The organic phase was dried (anhydrous magnesium sulfate) and concentrated. The product was isolated as the dibenzoyl-L-tartrate salt from ethyl ether to give N-[2-(4-methoxyphenyl)-1-methylethyl]-N-ethyl-[1-(4-acetylpiperazine-1-carbonyl)piperidin-4-ylmethyl]amine dibenzoyl-L-tartrate hydrate (0.13 grams, 26%), m.p. 117–119° C., M$^+$H 445.

4I. Similarly, substituting N-[2-(4-methoxyphenyl)-1-methylethyl]-N-ethyl-(piperidin-4-ylmethyl)amine hydrochloride with other compounds of Formula Ia and following the procedures described above in Example 4H the following compounds of Formula Ic were prepared:

N-{2-[3-(4-tert-Butylphenylcarbonylamino)phenyl]-1-methylethyl}-N-propyl-(1-carbamoylpiperidin-4-ylmethyl)amine, m.p. 182–183° C., M$^+$H 493; and N-{2-[3-(4-tert-Butylphenylcarbonylamino)phenyl]-1-methylethyl}-N-propyl-[1-(1,1-dioxo-thiomorpholine-4-carbonyl)piperidin-4-ylmethyl)amine hydrochloride, M$^+$H 611.

Example 5

Preparation of Compounds of Formula Id as Described in Scheme G

5A. N-[2-(4-Methoxyphenyl)-1-methylethyl]-N-ethyl-[1-(isopropyloxycarbonyl)piperidin-4-ylmethyl]amine dibenzoyl-L-tartrate To a mixture of N-[2-(4-methoxyphenyl)-1-methylethyl]-N-ethyl-(piperidin-4-ylmethyl)amine hydrochloride (0.2 grams, 0.55 mmole) and triethylamine (0.4 ml, 2.9 mmole) in dichloromethane (10 ml) was added 1.0M isopropyl chloroformate (0.83 ml, 0.83 mmole) in toluene. The reaction mixture was stirred at 22° C. for 16 hours, then concentrated under reduced pressure. The residue was partitioned between ethyl acetate (20 ml) and 5% aqueous sodium bicarbonate (20 ml). The dried (anhydrous magnesium sulfate) organic phase was concentrated under reduced pressure and the residue was subjected to flash column chromatography over silica gel eluting with 1% methanol in chloroform containing 0.5% ammonium hydroxide. The product was isolated as the dibenzoyl-L-tartrate salt (ethyl ether) to give N-[2-(4-methoxyphenyl)-1-methylethyl]-N-ethyl-[1-(isopropyloxycarbonyl)piperidin-4-ylmethyl] amine dibenzoyl-L-tartrate (0.345 grams, 85%), m.p. 96–98° C., M$^+$H 377.

5B. Similarly, substituting N-[2-(4-methoxyphenyl)-1-methylethyl]-N-ethyl-(piperidin-4-ylmethyl)amine hydrochloride with other compounds of Formula Ia and isopropyl chloroformate with other chloroformates, and following the procedures described above in Example 5A, the following compounds of Formula Id was prepared:

N-{2-[3-(4-tert-Butylphenylcarbonylamino)phenyl]-1-methylethyl}-N-propyl-[1-(ethoxycarbonyl)piperidin-4-ylmethyl]amine trifluoroacetate, M$^+$H 522.

Example 6

Preparation of a Compound of Formula Ie as Described in Scheme H 6A. (S)-N-{3-[4-({[2-(2,3-Dihydrobenzofuran-5-yl)-1-methylethyl]-ethylamino}methyl)piperidin-1-yl]-3-oxopropyl}methanesulfonamide To a solution of N-tert-butoxycarbonyl-β-alanine (0.31 grams, 165 mmole) in dichloromethane (5 ml) was added N,N'-carbonyldiimidazole (0.3 grams, 185 mmole). The reaction mixture was stirred at room temperature for 2 hours. To the reaction mixture was added a solution of (S)-N-[2-(2,3-dihydrobenzofuran-5-yl)-1-methylethyl]-N-ethyl-(piperidine-4-ylmethyl)amine (0.5 grams, 1.65 mmole) in dichloromethane (2 ml). The reaction mixture was stirred for 16 hours. The solvent was evaporated and the residue was purified by flash chromatography on silica gel using 2% methanol in dichloromethane containing 0.1% ammonium hydroxide. Appropriate fractions were combined and concentrated to give (S)-3-tert-butoxycarbonylamino-1-[4-({[2-(2,3-dihydrobenzofuran-5-yl)-1-methylethyl]-ethylamino}methyl)piperidin-1-yl]propan-1-one as a solid (0.76 grams, 97%).

To (S)-3-tert-Butoxycarbonylamino-1-[4-({[2-(2,3-dihydrobenzofuran-5-yl)-1-methylethyl]ethylamino}methyl)piperidin-1-yl]-propan-1-one (0.76 grams, 1.60 mmol) was added 20% trifluroacetic acid (20 ml). The reaction mixture was stirred at room temperature for 4 hours. The mixture was concentrated under reduced pressure and the residue was partitioned between dichloromethane and 1N sodium hydroxide. The organic layer was washed with water, dried over potassium carbonate and concentrated to give (S)-3-amino-1-[4-({[2-(2,3-dihydrobenzofuran-5-yl)-1-methylethyl]ethylamino}methyl)piperidin-1-yl]-propan-1-one as an oil (0.59 grams, 99%), M$^+$H 373.

To (S)-3-amino-1-[4-({[2-(2,3-dihydrobenzofuran-5-yl)-1-methylethyl]ethylamino}-methyl)piperidin-1-yl]propan-1-one (0.4 grams, 1.07 mmol) and diisopropylethylamine (0.21 grams, 1.62 mmole) in dichloromethane (10 ml) at 0° C. was added methanesulfonyl chloride (0.16 grams, 1.39 mmole). The reaction mixture was stirred at room temperature for 3 hours. The mixture was washed with water, dried over potassium carbonate and concentrated to give a residue which was purified by flash chromatography on silica gel using 3% methanol in dichloromethane containing 0.1% ammonium hydroxide. Appropriate fractions were combined and evaporated to give (S)-N-{3-[4-({[2-(2,3-dihydrobenzofuran-5-yl)-1-methylethyl] ethylamino}methyl)piperidin-1-yl]-3-oxopropyl}methanesulfonamide as an oil (0.32 grams, 66%), M$^+$H 452. Analysis % of the hydrochloride salt: Found: C, 51.83; H, 7.38; N, 7.87. Requires: C, 51.82; H, 7.56; N, 7.88.

6B. Similarly, substituting (S)-N-[2-(2,3-dihydrobenzofuran-5-yl)-1-methylethyl]-N-ethyl- (piperidine-4-ylmethyl)amine with other compounds of Formula Ia, optionally substituting methanesulfonyl chloride with other chlorides, and following the procedures described above in Example 6A, the following compounds of Formula Ie were prepared:

N-{1-[4-({[2-(3-Trifluoromethylphenyl)-1-methylethyl]ethylamino}methyl)piperidin-1-yl]-3-oxo-propyl}-methanesulfonamide hydrochloride, M+H 478;

N-{1-[4-({[2-(3-Trifluoromethylphenyl)-1-methylethyl]ethylamino}methyl)piperidin-1-yl]-3-oxo-propyl}-N-methyl-methanesulfonamide hydrochloride, M+H 492;

N-{1-[4-({[2-(3-Trifluoromethylphenyl)-1-methylethyl]ethylamino}methyl)piperidin-1-yl]-3-oxo-propyl}-N,N-dimethyl-methanesulfonamide hydrochloride, M+H 507;

(S)-N-{1-[4-({[2-(3-Trifluoromethylphenyl)-1-methylethyl]ethylamino}methyl)piperidin-1-yl]-3-oxo-propyl}-4-methylphenylsulfonamide hydrochloride, M+H 554;

N-{1-[4-({[2-(3-Trifluoromethylphenyl)-1-methylethyl]ethylamino}methyl)piperidine-1-carbonyl]-2-methanesulfonyl-ethyl}-methanesulfonamide hydrochloride, M+H 571;

(S)-N-{1-[4-({[2-(3-Chlorophenyl)-1-methylethyl]ethylamino}methyl)piperidine-1-carbonyl]-3-methanesulfonyl-propyl}-methanesulfonamide hydrochloride, M+H 536;

(S)-N-{1-[4-({[2-(3-Chlorophenyl)-1-methylethyl]ethylamino}methyl)piperidine-1-carbonyl]-3-methanesulfinyl-propyl}-methanesulfonamide hydrochloride, M+H 520;

(S)-N-{1-[4-({[2-(3-Chlorophenyl)-1-methylethyl]ethylamino}methyl)piperidine-1-carbonyl]-3-methanesulfonyl-propyl}-methanesulfonamide hydrochloride, M+H 536; and (S)-N-{2-[4-({[2-(2,3-Dihydrobenzofuran-5-yl)-1-methylethyl]ethylamino}methyl)piperidine-1-yl]-1,1-dimethyl-2-oxo-ethyl}-methanesulfonamide hydrochloride, M+H 466.

Example 7

Preparation of Compounds of Formula If as Described in Scheme I Route (a)

7A. (S)-N-[2-(2,3,-Dihydrobenzofuran-5-yl)-1-methylethyl]-N-ethyl-(1-methanesulfonylpiperidin-4-ylmethyl)amine (S)-N-[2-(2,3-dihydrobenzofuran-5-yl)-1-methylethyl]ethylamine (24 grams, 0.117 mole) was dissolved in dichloroethane (300 ml) and sodium triacetoxyborohydride (37.2 grams, 0.176 mole) was added. After stirring for 5 minutes N-methanesulfonylpiperidine-4-carboxaldehyde (22.4 grams, 0.117 mole) was added and the mixture was stirred for another 2 hours. 5% sodium carbonate (600 ml) was added and the mixture was extracted with dichloromethane. Evaporation of the solvent gave an oil which was recrystallized from ether to give (S)-N-[2-(2,3,-dihydrobenzofuran-5-yl)-1-methylethyl]-N-ethyl-(1-methanesulfonylpiperidin-4-ylmethyl)amine (28 grams, 63%), m.p. 99–101° C.

7B. (S)-N-[2-(2,3,-Dihydrobenzofuran-5-yl)-1-methylethyl]-N-ethyl-(1-methanesulfonylpiperidin-4-ylmethyl)amine hydrochloride (S)-N-[2-(2,3,-Dihydrobenzofuran-5-yl)-1-methylethyl]-N-ethyl-(1-methanesulfonylpiperidin-4-ylmethyl)amine (0.913 grams, 2.4 mmole) was dissolved in warm methanol (20 ml). To this solution was added 1.0M hydrogen chloride (2.5 ml) in ethyl ether. The solvent was removed under reduced pressure. The residue was dissolved in warm 2-butanone (3.0 ml). After 15 hours at 22° C., the crystals were collected and dried in vacuo to give (S)-N-[2-(2,3,-dihydrobenzofuran-5-yl)-1-methylethyl]-N-ethyl-(1-methanesulfonylpiperidin-4-ylmethyl)amine hydrochloride (0.99 grams, 99%), m.p. 112–114° C., M+H 381.

7C. (S)-N-[2-(2,3,-Dihydrobenzofuran-5-yl)-1-methylethyl]-N-ethyl-(1-methanesulfonylpiperidin-4-ylmethyl)amine phosphate (S)-N-[2-(2,3,-Dihydrobenzofuran-5-yl)-1-methylethyl]-N-ethyl-(1-methanesulfonylpiperidin-4-ylmethyl)amine (0.4 grams, 1.05 mmole) was dissolved in (10 ml) hot 10% aqueous ethanol. To this solution was added 85% phosphoric acid (0.122 grams, 1.06 mmole). The solution was stored at 22° C. for 16 hours. The deposited crystals were collected and dried in vacuo at 70° C. to give (S)-N-[2-(2,3,-dihydrobenzofuran-5-yl)-1-methylethyl]-N-ethyl-(1-methanesulfonylpiperidin-4-ylmethyl)amine phosphate (0.454 grams, 97%), m.p. 209–210° C.

7D. Similarly, substituting (S)-N-[2-(2,3-dihydrobenzofuran-5-yl)-1-methylethyl]-N-ethyl-(piperidine-4-ylmethyl)amine with other compounds of formula 4, optionally substituting methanesulfonyl chloride with other chlorides, and following the procedures described above in Examples 7A, 7B, or 7C, the following compounds of Formula If were prepared:

N-{2-[4-(2,2,2-Trifluoroethoxy)phenyl]-1-methylethyl}-N-propyl-(1-methanesulfonylpiperidin-4-ylmethyl)amine dibenzoyl-L-tartrate hydrate, M+H 451;

N-[2-(3-Trifluoromethylphenyl)-1-methylethyl]-N-ethyl-(1-methanesulfonyl-piperidin-4-ylmethyl)amine hydrochloride, M+H 407;

(S)-N-[2-(3-Trifluoromethylphenyl)-1-methylethyl]-N-ethyl-(1-methanesulfonylpiperidin-4-ylmethyl)amine hydrochloride, $[\alpha]_D^{25}$+10.2° (c 1.0 CH$_3$OH); M+H 407;

(R)-N-[2-(3-Trifluoromethylphenyl)-1-methylethyl]-N-ethyl-(1-methanesulfonylpiperidin-4-ylmethyl)amine hydrochloride, $[\alpha]_D^{25}$−8.86° (c 1.0 CH$_3$OH); M+H 407;

N-[2-(3-Trifluoromethylphenyl)-1-methylethyl]-N-ethyl-(1-methanesulfonylpiperidin-4-ylmethyl)amine dibenzoyl-L-tartrate hydrate, M+H 407;

N-[2-(2,3-Dihydrobenzo[1,4]dioxin-6-yl)-1-methylethyl]-N-ethyl-(1-methanesulfonylpiperidin-4-ylmethyl)amine hydrochloride, M+H 397;

(S)-N-[2-(2,3-Dihydrobenzo[1,4]dioxin-6-yl)-1-methylethyl]-N-ethyl-(1-methanesulfonylpiperidin-4-ylmethyl)amine hydrochloride, $[\alpha]_D^{25}$+11.2° (c 1.0 CH$_3$OH); M+H 397;

N-[2-(2,3-Dihydrobenzo[1,4]dioxin-6-yl)-1-methylethyl]-N-ethyl-(1-methanesulfonylpiperidin-4-ylmethyl)amine dibenzoyl-L-tartrate hydrate, M+H 397;

N-[2-(3-Trifluoromethylphenyl)-1-methylethyl]-N-ethyl-(1-methanesulfonylpiperidin-4-ylmethyl)amine dibenzoyl-L-tartrate hydrate, M+H 407;

N-[2-(3-Chlorophenyl)-1-methylethyl]-N-ethyl-(1-methanesulfonylpiperidin-4-ylmethyl)amine hydrochloride, M+H 373;

(S)-N-[2-(3-Chlorophenyl)-1-methylethyl]-N-ethyl-(1-methanesulfonylpiperidin-4-ylmethyl)amine hydrochloride, $[\alpha]_D^{25}$+11.20° (c 1.36 CH$_3$OH), M+H 373;

(R)-N-[2-(3-Chlorophenyl)-1-methylethyl]-N-ethyl-(1-methanesulfonylpiperidin-4-ylmethyl)amine hydrochloride, $[\alpha]_D^{25}$ –9.4° (c 0.42 CH$_3$OH), M$^+$H 373;

N-[2-(3-Aminosulfonyl-4-methoxyphenyl)-1-methylethyl]-N-propyl-[1-(tert-butoxycarbonyl)piperidin-4-ylmethyl]amine hydrochloride, M$^+$H 484;

N-[2-(3-Nitrophenyl)-1-methylethyl]-N-propyl-(1-methanesulfonylpiperidin-4-ylmethyl)amine hydrochloride, M$^+$H 384;

N-[2-(3-Aminosulfonyl-4-methoxyphenyl)-1-methylethyl]-N-propyl-(1-methanesulfonylpiperidin-4-ylmethyl)amine hydrochloride, M$^+$H 462;

(R)-N-[2-(2,3,-Dihydrobenzofuran-5-yl)-1-methylethyl]-N-ethyl-(1-methanesulfonylpiperidin-4-ylmethyl)amine (28 grams, 63%), $[\alpha]_D^{25}$ –9° (c 1.0 CH$_3$OH); M$^+$H 381;

N-[2-(2,3-Dihydrobenzofuran-5-yl)-1-methylethyl]-N-cyclopropylmethyl-(1-methanesulfonylpiperidin-4-ylmethyl)amine hydrochloride, M$^+$H 407;

N-[2-(2,3-Dihydrobenzofuran-5-yl)-1-methylethyl]-N-propyl-(1-methanesulfonylpiperidin-4-ylmethyl)amine hydrochloride, M$^+$H 395;

(S)-N-[2-(2,3-Dihydrobenzofuran-5-yl)-1-methylethyl]-N-propyl-(1-methanesulfonylpiperidin-4-ylmethyl)amine hydrochloride, M$^+$H 395;

N-[2-(Benzo[1,3]dioxol-5-yl)-1-methylethyl]-N-ethyl-(1-methanesulfonylpiperidin-4-ylmethyl)amine hydrochloride, M$^+$H 383;

N-[2-(2,3-Dihydrobenzo[1,4]dioxin-6-yl)-1-methylethyl]-N-isopropyl-(1-methanesulfonylpiperidin-4-ylmethyl)amine hydrochloride, M$^+$H 411;

N-[2-(2,3-Dihydrobenzofuran-6-yl)-1-methylethyl]-N-propyl-(1-methanesulfonylpiperidin-4-ylmethyl)amine hydrochloride, M$^+$H 395;

N-[2-(2,3-Dihydrobenzofuran-6-yl)-1-methylethyl]-N-ethyl-(1-methanesulfonylpiperidin-4-ylmethyl)amine hydrochloride, M$^+$H 381;

N-[2-(2,3-Dihydrobenzofuran-6-yl)-1-methylethyl]-N-cyclopropylmethyl-(1-methanesulfonylpiperidin-4-ylmethyl)amine hydrochloride, M$^+$H 407;

N-[2-(3-Oxo-4H-benzo[1,4]oxazin-6-yl)-1-methylethyl]-N-ethyl-(1-methanesulfonylpiperidin-4-ylmethyl)amine hydrochloride, M$^+$H 424.1;

N-[2-(4-Methylthiophenyl)-1-methylethyl]-N-ethyl-(1-methanesulfonylpiperidin-4-ylmethyl)amine hydrochloride, m.p. 71–72° C.;

N-[2-(Indan-5-yl)-1-methylethyl]-N-cyclopropylmethyl-(1-methanesulfonylpiperidin-4-ylmethyl)amine hydrochloride, M$^+$H 405;

N-[2-(Indan-5-yl)-1-methylethyl]-N-ethyl-(1-methanesulfonylpiperidin-4-ylmethyl)amine hydrochloride, M$^+$H 379;

N-[2-(Indan-5-yl)-1-methylethyl]-N-propyl-(1-methanesulfonylpiperidin-4-ylmethyl)amine hydrochloride, M$^+$H 393;

(S)-N-[2-(3,4-Dimethoxyphenyl)-1-methylethyl]-N-ethyl-(1-methanesulfonylpiperidin-4-ylmethyl)amine hydrochloride, M$^+$H 399;

N-[2-(4-Nitrophenyl)-1-methylethyl]-N-propyl-(1-methanesulfonylpiperidin-4-ylmethyl)amine hydrochloride, M$^+$H 398;

N-[2-(3,3-Dimethyl-2,3,-dihydrobenzofuran-5-yl)-1-methylethyl]-N-ethyl-(1-methanesulfonylpiperidin-4-ylmethyl)amine hydrochloride, m.p. 67–69° C.;

N-[2-(3-Nitrophenyl)-1-methylethyl]-N-ethyl-(1-methanesulfonylpiperidin-4-ylmethyl)amine, M$^+$H 384;

(S)-N-[2-(2,2-Dimethyl-2,3-dihydrobenzofuran-5-yl)-1-methylethyl]-N-ethyl-(1-methanesulfonylpiperidin-4-ylmethyl)amine hydrochloride, M$^+$H 409;

N-[2-(Benzofuran-5-yl)-1-methylethyl]-N-ethyl-(1-methanesulfonylpiperidin-4-ylmethyl)amine hydrochloride, M$^+$H 379;

N-[2-(5,6,7,8-Tetrahydronaphthalene-2-yl)-1-methylethyl]-N-ethyl-(1-methanesulfonylpiperidin-4-ylmethyl)amine hydrochloride, M$^+$H 393;

N-[2-(Naphthalene-2-yl)-1-methylethyl]-N-ethyl-(1-methanesulfonylpiperidin-4-ylmethyl)amine hydrochloride, M$^+$H 389; and N-[2-(Chroman-6-yl)-1-methylethyl]-N-ethyl-(1-methanesulfonylpiperidin-4-ylmethyl)amine hydrochloride, M$^+$H 395.

Route (b)

7E. Alternative Preparation of (S)-N-[2-(2,3,-Dihydrobenzofuran-5-yl)-1-methylethyl]-N-ethyl-(1-methanesulfonylpiperidin-4-ylmethyl)amine hydrochloride A solution of 1-methanesulfonylpiperidine-4-carbonyl chloride in dichloromethane (10 ml) was added to a suspension of (S)-N-[2-(2,3,-dihydrobenzofuran-5-yl)-1-methylethyl]-ethylamine hydrochloride (1.21 grams, 5 mmole) in dichloromethane (10 ml). The mixture was cooled to 0° C., and triethylamine (1.7 ml, 12.2 mmol) was added dropwise. When the addition was complete, the mixture was warmed to room temperature and stirred for about 1 hour. Saturated ammonium chloride was added (20 ml) and the separated organic layer was extracted once with dichloromethane (20 ml). The combined organic layers were washed with 1N hydrochloric acid (25 ml), saturated sodium bicarbonate (25 ml), dried over magnesium sulfate, and concentrated to give (S)-N-[2-(2,3,-dihydrobenzofuran-5-yl)-1-methylethyl]-N-ethyl-(1-methanesulfonylpiperidin-4-ylcarbonyl)amine as an off white foam (2.21 g).

A solution of (S)-N-[2-(2,3,-dihydrobenzofuran-5-yl)-1-methylethyl]-N-ethyl-(1-methanesulfonylpiperidin-4-ylcarbonyl)amine (2.21 g, 5 mmol) in tetrahydrofuran (5 ml) was added dropwise to a suspension of lithium aluminum hydride (0.38 g, 10 mmol) in tetrahydrofuran (10 ml) at 0° C., under a nitrogen atmosphere. The mixture was heated at reflux temperature for 2 hours and cooled to room temperature. Water (380 ml) was added dropwise to the mixture, followed by 15% sodium hydroxide (380 ml), and additional water (1550 μL). The mixture was stirred at room temperature for about 15 minutes and filtered. The filtrate was washed and rinsed with dichloromethane. Evaporation of the solvent gave a colorless oil, which solidified upon standing. Recrystallization from ethyl acetate/hexane (1:1) gave (S)-N-[2-(2,3,-dihydrobenzofuran-5-yl)-1-methylethyl]-N-ethyl-(1-methanesulfonylpiperidin-4-ylmethyl)amine as colorless crystals (1.02 g).

Route (c)

7F. N-[2-(4-Methoxyphenyl)-1-methylethyl]-N-ethyl-(1-isopropylsulfonylpiperidin-4-ylmethyl)amine dibenzoyl-L-tartrate To a mixture of N-[2-(4-methoxyphenyl)-1-methylethyl]-N-ethyl-(piperidin-4-ylmethyl)amine hydrochloride (0.2 grams, 0.55 mmole) in dichloromethane (10 ml) was added triethylamine (0.4 ml, 3 mmole) and isopropylsulfonyl chloride (0.1 ml, 0.89 mmole). The reaction mixture was stirred at 22° C. for 16 hours. The residue was concentrated under reduced pressure and partitioned between ethyl acetate and 5% sodium bicarbonate solution. The dried (anhydrous magnesium sulfate) organic phase was concentrated under reduced pressure. The residue was subjected to column chromatography over silica gel eluting with 50% ethyl acetate/hexane containing 0.5% ammonium hydroxide. The product was obtained as a dibenzoyl-L-tartrate salt to give N-[2-(4-methoxyphenyl)-1-methylethyl]-N-ethyl-(1-isopropylsulfonylpiperidin-4-ylmethyl)amine dibenzoyl-L-tartrate (0.211 grams, 51%), M$^+$H 397 (free base).

7G. Similarly, substituting N-[2-(4-methoxyphenyl)-1-methylethyl]-N-ethyl-(piperidin-4-ylmethyl)amine with other compounds of Formula Ia, optionally substituting isopropyl sulfonyl chloride with other sulfonyl chlorides, and following the procedures described above in Example 7F, the following compounds of Formula If were prepared:

N-[2-(4-Methoxyphenyl)-1-methylethyl]-N-ethyl-(1-methanesulfonylpiperidin-4-ylmethyl)amine hydrochloride, m.p. 85–86° C.;

(S)-N-[2-(4-Methoxyphenyl)-1-methylethyl]-N-ethyl-(1-methanesulfonylpiperidin-4-ylmethyl)amine hydrochloride, $[\alpha]_D^{25}$+11.8° (c 1.0 CH$_3$OH);

(R)-N-[2-(4-Methoxyphenyl)-1-methylethyl]-N-ethyl-(1-methanesulfonylpiperidin-4-ylmethyl)amine hydrochloride, $[\alpha]_D^{25}$–12.0° (c 1.0 CH$_3$OH);

N-[2-(4-Methoxyphenyl)-1-methylethyl]-N-ethyl-(1-methanesulfonylpiperidin-4-ylmethyl)amine dibenzoyl-L-tartrate, m.p. 119–120° C.;

N-[2-(4-Methoxyphenyl)-1-methylethyl]-N-ethyl-(1-trifluoromethylsulfonylpiperidin-4-ylmethyl)amine dibenzoyl-L-tartrate, M$^+$H 423;

N-[2-(3-Trifluoromethylphenyl)-1-methylethyl]-N-ethyl-(1-isopropylsulfonylpiperidin-4-ylmethyl)amine dibenzoyl-L-tartrate, M$^+$H 435;

N-[2-(2,3-Dihydrobenzo[1,4]dioxin-6-yl)-1-methylethyl]-N-ethyl-(1-isopropylsulfonylpiperidin-4-ylmethyl)amine dibenzoyl-L-tartrate, M$^+$H 425;

N-{2-[3-(4-tert-Butylphenylcarbonylamino)phenyl]-1-methylethyl}-N-propyl-[1-(4-methylphenylsulfonyl)piperidin-4-ylmethyl]amine trifluoroacetate, M$^+$H 604;

N-{2-[3-(4-tert-Butylphenylcarbonylamino)phenyl]-1-methylethyl}-N-propyl-[1-(isopropylsulfonyl)piperidin-4-ylmethyl]amine trifluoroacetate, M$^+$H 556; and N-{2-[3-(4-tert-Butylphenylcarbonylamino)phenyl]-1-methylethyl}-N-propyl-[1-(methanesulfonyl)piperidin-4-ylmethyl]amine trifluoroacetate, M$^+$H 528.

7H. N-[2-(4-Methanesulfonylphenyl)-1-methylethyl]-N-ethyl-(1-methanesulfonylpiperidin-4-ylmethyl)amine hydrochloride A solution of N-[2-(4-methylthiophenyl)-1-methylethyl]-N-ethyl-(1-methanesulfonylpiperidin-4-ylmethyl)amine hydrochloride (0.25 grams, 0.6 mmole) in 30% aqueous methanol (7 ml) was added to a solution of Oxone® (0.73 grams, 1.2 mmole) in water (10 ml) at 0° C. after 2 hours at 0° C. the volume was reduced to 10 ml and the solution was made strongly basic with 3N sodium hydroxide. The mixture was extracted with ethyl ether (50 ml). The organic phase was dried (anhydrous magnesium sulfate) and concentrated under reduced pressure. The product was isolated as the hydrochloride salt from ethyl ether to give N-[2-(4-methanesulfonylphenyl)-1-methylethyl]-N-ethyl-(1-methanesulfonylpiperidin-4-ylmethyl)amine hydrochloride (0.25 grams, 92%), m.p. 92–93° C.

Example 8

Preparation of a Compound of Formula Ig as Described in Scheme J 8A. (S)-N-[2-(2,3-Dihydrobenzofuran-5-yl)-1-methylethyl]-N-ethyl-[1-(morpholine-4-sulfonyl)piperidin-4-ylmethyl]amine To a solution of (S)-N-[2-(2,3-dihydrobenzofuran-5-yl)-1-methylethyl]-N-ethyl-(piperidin-4-ylmethyl)amine (0.2 grams, 0.66 mmole) and triethylamine (0.15 grams, 1.48 mmole) in dichloromethane (4 ml) at 0° C. was added dropwise a solution of chlorosulfonic acid (0.08 grams, 0.66 mmol) in dichloromethane (0.5 ml). The mixture was stirred at room temperature for 16 hours, and the solvent was removed under reduced pressure. To the residue was added benzene (4 ml) and phosphorous pentachloride (0.14 grams, 0.67 mmole). The mixture was heated under reflux for 2 hours. The solvent was removed under reduced pressure and the residue was partitioned between ethyl acetate and 1N sodium hydroxide. The organic layer was washed with brine, dried over sodium sulfate and concentrated to give (S)-N-[2-(2,3-dihydrobenzofuran-5-yl)-1-methylethyl]-N-ethyl-(1-chlorosulfonylpiperidin-4-ylmethyl)amine as a viscous oil (0.18 grams, 70%), M$^+$H 401.

A mixture of (S)-N-[2-(2,3-dihydrobenzofuran-5-yl)-1-methylethyl]-N-ethyl-(1-chlorosulfonylpiperidin-4-ylmethyl)amine (0.18 grams, 0.45 mmole), morpholine (0.04 grams, 0.45 mmol) and diisopropylethylamine (0.12 grams, 0.93 mmole) in tetrahydrofuran (10 ml) was stirred at room temperature for 16 hours. The solvent was removed under reduced pressure and the residue was partitioned between dichloromethane and water. The organic layer was dried over potassium carbonate and evaporated to give a residue, which was purified by flash chromatography on silica gel using 40% ethyl acetate in hexane. Appropriate fractions were combined and evaporated to give (S)-N-[2-(2,3-dihydrobenzofuran-5-yl)-1-methylethyl]-N-ethyl-[1-(morpholine-4-sulfonyl)-piperidin- 4-ylmethyl]amine as an oil, (0.17 g, 85%), M$^+$H 452. Analysis % of the hydrochloride salt: Found: C, 54.06; H, 7.62; N, 8.24. Requires: C, 54.01; H, 8.00; N, 8.22.

8B. Similarly, substituting (S)-N-[2-(2,3-dihydrobenzofuran-5-yl)-1-methylethyl]-N-ethyl-(piperidin-4-ylmethyl)amine with other compounds of Formula Ia, optionally substituting morpholine with other amines, and following the procedures described above in Example 8A, the following compounds of Formula Ig were prepared:

N-[2-(3-Trifluoromethylphenyl)-1-methylethyl]-N-ethyl-[1-(dimethylaminosulfonyl)piperidin-4-ylmethyl]amine dibenzoyl-L-tartrate, M$^+$H 436;

N-[2-(2,3-Dihydrobenzo[1,4]dioxin-6-yl)-1-methylethyl]-N-ethyl-[1-(dimethylaminosulfonyl)piperidin-4-ylmethyl]amine dibenzoyl-L-tartrate, M$^+$H 426;

N-[2-(4-Trifluoromethylphenyl)-1-methylethyl]-N-ethyl-[1-(dimethylaminosulfonyl)piperidin-4-ylmethyl]amine dibenzoyl-L-tartrate, M$^+$H 436;

(S)-N-[2-(2,3-Dihydrobenzofuran-5-yl)-1-methylethyl]-N-ethyl-[1-(pyrrolidine-1-sulfonyl)piperidin-4-ylmethyl]amine hydrochloride. Analysis % : Found: C, 57.01; H, 7.93; N, 8.53. Requires: C, 56.99; H, 8.19; N, 8.67, M$^+$H 436;

(S)-N-[2-(2,3-Dihydrobenzofuran-5-yl)-1-methylethyl]-N-ethyl-[1-(1,1-dioxo-thiomorpholine-4-sulfonyl)piperidin-4-ylmethyl]amine hydrochloride, M$^+$H 500;

(S)-N-[2-(2,3-Dihydrobenzofuran-5-yl)-1-methylethyl]-N-ethyl-[1-(thiomorpholine-4-sulfonyl)piperidin-4-ylmethyl]amine hydrochloride. Analysis %: Found: C, 53.47; H, 7.56; N, 8.08; Requires: C, 53.46; H, 7.69; N,8.13; M$^+$H 468; and N-{2-[3-(4-tert-Butylphenylcarbonylamino)phenyl]-1-methylethyl}-N-propyl-[1-(dimethylaminosulfonyl)piperidin-4-ylmethyl]amine trifluoroacetate, M$^+$H 557.

8C. 3-[4-({[2-(2,3-Dihydrobenzofuran-5-yl)-1-methylethyl] ethylamino}methyl)piperidine-1-sulfonylamino]propionic acid A mixture of β-alanine (0.05 grams, 0.56 mmole) and trimethylsilylcyanide (0.11 grams, 1.1 mmole) in acetonitrile was heated under reflux for one hour. A solution of (S)-N-[2-(2,3-dihydrobenzofuran-5-yl)-1-methylethyl]-N-ethyl-(1-chlorosulfonylpiperidine-4-ylmethyl)amine (0.2 grams, 0.50 mmole) in acetonitrile was added and the mixture was heated under reflux for another 5 hours. The reaction mixture was quenched with methanol and evaporated to leave a residue which was purified by RP HPLC, Vydac C4 column using a gradient of 5–65% water/acetonitrile containing 0.1% trifluoroacetic acid. Appropriate fractions were combined and evaporated to give (S)-3-[4-({[2-(2,3-dihydrobenzofuran-5-yl)-1-methylethyl] ethylamino}methyl)piperidine-1-sulfonylamino]-propionic acid as a trifluroacetic acid salt (0.14 grams, 51%), $M^+H$ 454. Analysis %: Found: C, 48.22; H, 5.88; N, 7.00. Requires: C, 48.08; H, 5.89; N, 6.73.

Example 9

Preparation of a Compound of Formula Ih as Described in Scheme K 9A. (S)-N-{2-[4-({[2-(2,3-Dihydrobenzofuran-5-yl)-1-methylethyl]ethylamino}methyl)piperidine-1-sulfonyl] ethyl}methanesulfonamide To a cold solution of 2-chloroethylsulfonyl chloride (0.32 grams, 1.99 mmole) in dichloromethane (5 ml) was added dropwise a solution of (S)-N-[1-(2,3-dihydrobenzofuran-5-yl)-1-methylethyl]-N-ethyl-(piperidin-4-ylmethyl)amine (0.60 grams, 1.99 mmole) in dichloromethane (2 ml). The reaction mixture was stirred at room temperature for 16 hours, washed with water, dried over potassium carbonate, and the solvent evaporated to leave a residue. The residue was purified by flash chromatography on silica gel eluting with a gradient of 25–50% hexane in ethyl acetate. Appropriate fractions were combined and evaporated to give (S)-N-[2-(2,3-dihydrobenzofuran-5-yl)-1-methylethyl]-N-ethyl-(1-ethenesulfonylpiperidin-4-ylmethyl)amine as an oil (0.36 grams, 46%).

To a solution of methane sulfonamide (0.18 grams, 1.84 mmole) in dimethylformamide (2 ml) was added 60% sodium hydride (0.048 grams, 1.2 mmole) in mineral oil. The reaction mixture was heated at 120° C. for 30 minutes, and cooled to 100° C. A solution of (S)-N-[2-(2,3-dihydrobenzofuran-5-yl)-1-methylethyl]-N-ethyl-(1-ethenesulfonylpiperidin-4-ylmethyl)amine (0.36 grams, 0.92 mmol) in dimethylformamide was added all at once. The reaction mixture was heated at 100° C. for 40 minutes. The solvent was evaporated under reduced pressure and the residue was partitioned between dichloromethane and water. The organic layer was dried over potassium carbonate and evaporated to leave a residue, which was purified by flash chromatography using ethyl acetate. Appropriate fractions were combined and evaporated to give (S)-N-{2-[4-({[2-(2,3-dihydrobenzofuran-5-yl)-1-methylethyl] ethylamino}methyl)piperidine-1-sulfonyl]ethyl}-methanesulfonamide as an oil (0.32 grams, 71%). $M^+H$ 488. Analysis % of the hydrochloride salt: Found: C, 48.26; H, 7.09; N, 8.10. Requires: C, 48.59; H, 7.42; N, 7.73.

9B. Similarly, substituting 2-chloroethyl sulfonyl chloride with 3-chloropropyl sulfonyl chloride, and following the procedures described above in Example 9A, (S)-N-{2-[4-({[2-(2,3-dihydrobenzofuran-5-yl)-1-methylethyl] ethylamino}methyl)piperidine-1-sulfonyl]propyl}-methanesulfonamide, $M^+H$ 502, was prepared.

Example 10

Preparation of a Compounds of Formula Ij as Described in Scheme L Route (a)

10A. N-{2-[3-(Furan-2-carbonylamino)phenyl]-1-methylethyl}-N-propyl-(1-methanesulfonylpiperidin-4-ylmethyl)amine N-[2-(3-Nitrophenyl)-1-methylethyl)-N-propyl-(1-methanesulfonylpiperidin-4-ylmethyl)amine (500 mg) and 10% palladium on carbon (50 mg) were combined with ethanol (25 ml) and hydrogenated at 40 p.s.i. for 18 hours. The resulting solution was filtered and the solvent removed under vacuum. The residue was dissolved in ethyl acetate (10 ml) and a solution of potassium carbonate (500 mg) in water (5 ml) was added. The mixture was cooled in an ice bath. 2-Furoyl chloride (0.07 ml) was added and the entire mixture stirred for 3 hours. The layers were separated and the organic layer dried over magnesium sulfate, filtered, and the solvent removed. The resulting oil was taken up in isopropanol and 1 M hydrochloric acid (1.5 ml) in ether was added. The resulting salt was filtered and dried in a desiccator to give N-{2-[3-(furan-2-carbonylamino)phenyl]-1-methylethyl}-N-propyl-(1-methanesulfonylpiperidin-4-ylmethyl)amine hydrochloride, $M^+H$ 462.

10B. Similarly, substituting N-[2-(3-nitrophenyl)-1-methylethyl)-N-propyl-(1-methanesulfonylpiperidin-4-ylmethyl)amine with other amines, and optionally substituting 2-furoyl chloride with other carbonyl chlorides, and following the procedures described above in Example 10A, the following compounds of Formula Ij were prepared:

N-{2-[3-(Cyclohexanecarbonylamino)phenyl]-1-methylethyl}-N-propyl-[1-(morpholine-4-carbonyl) piperidin-4-ylmethyl]amine hydrochloride, $M^+H$ 513;

N-{2-[3-(2,5-Dioxo-pyrrolidine-1-carbonylamino) phenyl]-1-methylethyl}-N-propyl-[1-(morpholine-4-carbonyl)piperidin-4-ylmethyl]amine hydrochloride, $M^+H$ 485;

N-{2-[4-(Cyclohexanecarbonylamino)phenyl]-1-methylethyl}-N-propyl-[1-(morpholine-4-carbonyl) piperidin-4-ylmethyl]amine hydrochloride, $M^+H$ 513;

N-{2-[4-(Ethylcarbonylamino)phenyl]-1-methylethyl}-N-propyl-[1-(morpholine-4-carbonyl)piperidin-4-ylmethyl]amine hydrochloride, $M^+H$ 459;

N-{2-[4-(Morpholine-4-carbonylamino)phenyl]-1-methylethyl}-N-propyl-[1-(morpholine-4-carbonyl) piperidin-4-ylmethyl]amine hydrochloride, $M^+H$ 516;

N-{2-[3-(3-Methoxyphenylcarbonylamino)phenyl]-1-methylethyl}-N-propyl-[1-(morpholine-4-carbonyl) piperidin-4-ylmethyl]amine, $M^+H$ 537;

N-{2-[3-(4-Methoxyphenylcarbonylamino)phenyl]-1-methylethyl}-N-propyl-[1-(morpholine-4-carbonyl) piperidin-4-ylmethyl]amine, $M^+H$ 537;

N-{2-[3-(2-Methoxyphenylcarbonylamino)phenyl]-1-methylethyl}-N-propyl-[1-(morpholine-4-carbonyl) piperidin-4-ylmethyl]amine, $M^+H$ 537;

N-{2-[3-(Furan-2-carbonylamino)phenyl]-1-methylethyl}-N-propyl-[1-(morpholine-4-carbonyl) piperidin-4-ylmethyl]amine, $M^+H$ 497;

N-{2-[3-(Naphthalene-2-carbonylamino)phenyl]-1-methylethyl}-N-propyl-[1-(morpholine-4-carbonyl) piperidin-4-ylmethyl]amine, $M^+H$ 557;

N-{2-[3-(Thiophene-2-carbonylamino)phenyl]-1-methylethyl}-N-propyl-[1-(morpholine-4-carbonyl) piperidin-4-ylmethyl]amine, $M^+H$ 513;

N-{2-[3-(Naphthalene-1-carbonylamino)phenyl]-1-methylethyl}-N-propyl-[1-(morpholine-4-carbonyl) piperidin-4-ylmethyl]amine, $M^+H$ 557;

N-{2-[3-(4-Nitrophenylcarbonylamino)phenyl]-1-methylethyl}-N-propyl-[1-(morpholine-4-carbonyl)piperidin-4-ylmethyl]amine trifluoroacetate, M+H 551;

N-{2-[3-(Phenylcarbonylamino)phenyl]-1-methylethyl}-N-propyl-[1-(morpholine-4-carbonyl)piperidin-4-ylmethyl]amine trifluoroacetate, M+H 507;

N-{2-[3-(4-Chlorophenylcarbonylamino)phenyl]-1-methylethyl}-N-propyl-[1-(morpholine-4-carbonyl)piperidin-4-ylmethyl]amine, M+H 541;

N-{2-[3-(4-Bromophenylcarbonylamino)phenyl]-1-methylethyl}-N-propyl-[1-(morpholine-4-carbonyl)piperidin-4-ylmethyl]amine, M+H 585;

N-{2-[3-(4-Methylphenylcarbonylamino)phenyl]-1-methylethyl}-N-propyl-[1-(morpholine-4-carbonyl)piperidin-4-ylmethyl]amine, M+H 521;

N-{2-[3-(Isopropylcarbonylamino)phenyl]-1-methylethyl}-N-propyl-(1-methanesulfonylpiperidin-4-ylmethyl)amine hydrochloride, M+H 438;

N-{2-[3-(Phenylethylcarbonylamino)phenyl]-1-methylethyl}-N-propyl-(1-methanesulfonylpiperidin-4-ylmethyl)amine, M+H 500;

N-{2-[3-(Butylcarbonylamino)phenyl]-1-methylethyl}-N-propyl-(1-methanesulfonylpiperidin-4-ylmethyl)amine, M+H 452;

N-{2-[3-(Furan-2-carbonylamino)phenyl]-1-methylethyl}-N-propyl-(1-methanesulfonylpiperidin-4-ylmethyl)amine, M+H 462;

N-{2-[3-(4-Fluorophenylcarbonylamino)phenyl]-1-methylethyl}-N-propyl-(1-methanesulfonylpiperidin-4-ylmethyl)amine, M+H 490;

N-{2-[3-(Nonylcarbonylamino)phenyl]-1-methylethyl}-N-propyl-(1-methanesulfonylpiperidin-4-ylmethyl)amine hydrochloride, M+H 522;

N-{2-[3-(Cyclohexanecarbonylamino)phenyl]-1-methylethyl}-N-ethyl-(1-methanesulfonylpiperidin-4-ylmethyl)amine hydrochloride, M+H 464;

N-{2-[4-(Cyclohexanecarbonylamino)-phenyl]-1-methylethyl}-N-propyl-(1-methanesulfonylpiperidin-4-ylmethyl)amine, M+H 478;

N-{2-[4-(Furan-2-carbonylamino)-phenyl]-1-methylethyl}-N-propyl-(1-methanesulfonylpiperidin-4-ylmethyl)amine hydrochloride, M+H 462; and N-{2-[3-(Furan-2-carbonylamino)phenyl]-1-methylethyl}-N-ethyl-(1-methanesulfonylpiperidin-4-ylmethyl)amine hydrochloride, M+H 448.

Route (b)

10C. N-{2-[3-(4-sulfamoylphenylcarbonylamino)phenyl]-1-methylethyl}-N-propyl-[1-(morpholine-4-carbonyl)piperidine-4-ylmethyl]amine N-[2-(3-aminophenyl)-1-methyl ethyl]-N-propyl-[1-(morpholino-4-carbonyl)-piperidine-4-ylmethyl]amine (78 mg) was dissolved in N,N-dimethylformamide (2.5 ml)and 4-sulfamidobenzoic acid (40 mg) was added. To this solution was added in order 4-methylmorpholine (0.03 ml), 1-hydroxybenzotriazole (27 mg), and 1-[3-(dimethylamino)propyl]-3-ethylcarbodiimide hydrochloride (40 mg). The resulting mixture was stirred at room temperature under nitrogen for 18 hours, and then partitioned between water and ethyl acetate. The organic layer was separated and dried over sodium sulfate. The solvent was evaporated and the residue chromatographed over silica gel, eluting with 5% methanol in dichloromethane, to give N-{2-[3-(4-sulfamonylphenylcarbonylamino)phenyl]-1-methylethyl}-N-propyl-[1-(morpholine-4-carbonyl)piperidine-4-ylmethyl]amine (70 mg), M+H 586.

10D. Similarly, substituting N-[2-(3-aminophenyl)-1-methylethyl]-N-propyl-[1-(morpholino-4-carbonyl)piperidine-4-ylmethyl]amine with other amines of Formula Ii, and substituting 4-sulfamidobenzoic acid with other benzoic acid derivatives, and following the procedures described above in Example 10C, the following compounds of Formula Ij were prepared:

N-{2-[3-(4-Sulfamoylphenylcarbonylamino)phenyl]-1-methylethyl}-N-propyl-[1-(morpholine-4-carbonyl)piperidin-4-ylmethyl]amine hydrochloride, M+H 586;

N-{2-[3-(2,3-Dihydrobenzofuran-5-carbonylamino)phenyl]-1-methylethyl}-N-propyl-[1-(morpholine-4-carbonyl)piperidin-4-ylmethyl]amine hydrochloride, M+H 541;

N-{2-[3-(1H-Pyrazole-4-carbonylamino)phenyl]-1-methylethyl}-N-propyl-[1-(morpholine-4-carbonyl)piperidin-4-ylmethyl]amine hydrochloride, M+H 497;

N-{2-[3-(1-Oxide-pyridine-4-carbonylamino)phenyl]-1-methylethyl}-N-propyl-[1-(morpholine-4-carbonyl)piperidin-4-ylmethyl]amine hydrochloride, M+H 524;

N-{2-[3-(2,3-Dihydrobenzo[1,4]dioxine-6-carbonylamino)phenyl]-1-methylethyl}-N-propyl-[1-(morpholine-4-carbonyl)piperidin-4-ylmethyl]amine hydrochloride, M+H 565;

N-{2-[3-(1H-1,2,4-Triazole-3-carbonylamino)phenyl]-1-methylethyl}-N-propyl-[1-(morpholine-4-carbonyl)piperidin-4-ylmethyl]amine hydrochloride, M+H 498;

(R)-N-{2-[3-(4-Sulfamoylphenyl-carbonylamino)phenyl]-1-methylethyl}-N-propyl-[1-(isopropylaminocarbonyl)piperidin-4-ylmethyl]amine hydrochloride, M+H 558; and (R)-N-{2-[3-(Imidazole-4-carbonylamino)phenyl]-1-methylethyl}-N-propyl-[1-(isopropylaminocarbonyl)piperidin-4-ylmethyl]amine hydrochloride, M+H 469.

Route (c)

10E. (R)-N-{2-[3-(4-Methoxyphenylcarbonylamino)phenyl]-1-methylethyl}-N-propyl-[1-(morpholine-4-carbonyl)piperidine-4-ylmethyl]amine (R,R)-N-[2-(4-Nitrophenyl)-1-methylethyl]-N-propyl-(1-phenylethyl)amine hydrochloride was dissolved in ethanol (100 ml) and water (16 ml). To this solution was added iron powder (2.44 g) and ammonium formate (2.25 g). The mixture was heated at reflux for 3 hours, cooled to room temperature and filtered through a glass fiber filter. The filtrate was evaporated in vacuo, and the residue was partitioned between ethyl acetate and dilute sodium hydroxide. The organic layer was dried over sodium sulfate, filtered, and the solvent removed in vacuo to give (R,R)-N-[2-(4-aminophenyl)-1-methylethyl]-N-propyl-(1-phenylethyl)amine as a yellow syrup (2.9 g).

(R,R)-N-[2-(4-aminophenyl)-1-methylethyl]-N-propyl-(1-phenylethyl)amine (0.95 g) was dissolved in ethyl acetate (50 ml) and saturated potassium carbonate solution (50 ml). This mixture was cooled in an ice bath and 4-methoxybenzoyl chloride (0.55 g) was added. The mixture was stirred for 18 hours and the layers were separated. The organic layer was dried over sodium sulfate, filtered, and the solvent removed in vacuo. The residue was dissolved in isopropanol and 1M hydrochloric acid (1 eq) was added. Slow addition of ether induced crystallization. The crystals were filtered and dried in a desiccator for 18 hours to give (R,R)-N-{2-[3-(4-methoxyphenylcarbonylamino)phenyl]-1-methylethyl}-N-propyl-(1-phenylethyl)amine hydrochloride (0.98 g), M+H 431.

(R,R)-N-{2-[3-(4-methoxyphenylcarbonylamino)phenyl]-1-methylethyl}-N-propyl-(1-phenylethyl)amine (0.98 g) was dissolved in ethanol (100 ml) and added to 10% palladium on carbon (0.1 g). To this mixture was added ammonium formate (1.2 g), and the mixture heated at reflux for 2 hours, cooled to room temperature, and filtered. The filtrate was evaporated in vacuo, and the residue was partitioned between ethyl acetate and dilute sodium hydroxide. The organic layer was dried over sodium sulfate, filtered, and the solvent removed in vacuo to give [(R)-N-{2-[3-(4-methoxyphenylcarbonylamino)phenyl]-1-methylethyl}propylamine.

(R)-N-{2-[3-(4-Methoxyphenylcarbonylamino)phenyl]-1-methylethyl}-propylamine (0.32 g), dichloroethane (20 ml) and 1-(morpholine-4-carbonyl)piperidine-4-carboxaldehyde (0.32 g) and were stirred under nitrogen for 30 minutes. Sodium triacetoxyborohydride (0.5 g) was added, and the mixture stirred at room temperature for about 72 hours. The mixture was diluted with diethyl ether (50 ml) and 10% sodium hydroxide solution (20 ml). The organic layer was dried with sodium sulfate, filtered, and the solvent evaporated in vacuo. The residue was chromatographed, eluting with methanol/dichloromethane to give (R)-N-{2-[3-(4-methoxyphenylcarbonylamino)phenyl]-1-methylethyl}-N-propyl-[1-(morpholine-4-carbonyl)piperidine-4-ylmethyl]amine, (0.42 g), $[\alpha]_D^{25}$–42° (c 1.0 CH$_3$OH); M$^+$H 537.

10F. Similarly, substituting (R)-N-{2-[3-(4-methoxyphenylcarbonylamino)phenyl]-1-methylethyl}propylamine with other compounds of formula 4' and optionally substituting 1-(morpholine-4-carbonyl)piperidine-4-carboxaldehyde with other compounds of formula 17, and following the procedures described above in Example 10E, the following compounds of Formula Ij were prepared:

(S)-N-{2-[3-(Cyclohexanecarbonylamino)phenyl]-1-methylethyl}-N-propyl-[1-(morpholine-4-carbonyl)piperidin-4-ylmethyl]amine hydrochloride, $[\alpha]_D^{25}$+16.2° (c 1.0 CHCl$_3$), M$^+$H 513;

(R)-N-{2-[3-(Cyclohexanecarbonylamino)phenyl]-1-methylethyl}-N-propyl-[1-(morpholine-4-carbonyl)piperidin-4-ylmethyl]amine hydrochloride, $[\alpha]_D^{25}$–30° (c 1.0 CHCl$_3$), M$^+$H 513;

(S)-N-{2-[3-(Furan-2-carbonylamino)phenyl]-1-methylethyl}-N-propyl-(1-methanesulfonylpiperidin-4-ylmethyl)amine hydrochloride, M$^+$H 462;

(S)-N-{2-[3-(4-Fluorophenylcarbonylamino)phenyl]-1-methylethyl}-N-propyl-(1-methanesulfonylpiperidin-4-ylmethyl)amine, M$^+$H 490;

(S)-N-{2-[3-(Tetrahydrofuran-2-carbonylamino)phenyl]-1-methylethyl}-N-propyl-(1-methanesulfonylpiperidin-4-ylmethyl)amine hydrochloride, M$^+$H 466;

(S)-N-{2-[3-(Tetrahydrofuran-2-carbonylamino)phenyl]-1-methylethyl}-N-propyl-[1-(morpholine-4-carbonyl)piperidin-4-ylmethyl]amine hydrochloride, M$^+$H 501;

(S)-N-{2-[3-(4-Fluorophenylcarbonylamino)phenyl]-1-methylethyl}-N-propyl-[1-(morpholine-4-carbonyl)piperidin-4-ylmethyl]amine, M$^+$H 525;

(S)-N-{2-[3-(Cyclohexanecarbonylamino)phenyl]-1-methylethyl}-N-propyl-(1-methanesulfonylpiperidin-4-ylmethyl)amine hydrochloride, M$^+$H 478;

(S)-N-{2-[3-(4-Fluorophenylcarbonylamino)-4-methoxyphenyl]-1-methylethyl}-N-propyl-(1-methanesulfonylpiperidin-4-ylmethyl)amine hydrochloride, M$^+$H 502;

(S)-N-{2-[3-Fluorophenylcarbonylamino)-4-methoxyphenyl]-1-methylethyl}-N-propyl-[1-(morpholine-4-carbonyl)piperidin-4-ylmethyl]amine hydrochloride, M$^+$H 537;

N-{2-[3-(Morpholine-4-carbonylamino)phenyl]-1-methylethyl}-N-propyl-[1-(morpholine-4-carbonyl)piperidin-4-ylmethyl]amine hydrochloride, M$^+$H 516;

N-{2-[3-(3,4,5-Trimethoxyphenylcarbonylamino)phenyl]-1-methylethyl}-N-propyl-[1-(morpholine-4-carbonyl)piperidin-4-ylmethyl]amine, M$^+$H 597;

N-{2-[3-(3,5-Dichlorophenylcarbonylamino)phenyl]-1-methylethyl}-N-propyl-[1-(morpholine-4-carbonyl)piperidin-4-ylmethyl]amine hydrochloride, M$^+$H 575;

N-{2-[3-(Benzo[1,3]dioxole-5-carbonylamino)phenyl]-1-methylethyl}-N-propyl-[1-(morpholine-4-carbonyl)piperidin-4-ylmethyl]amine hydrochloride, M$^+$H 551;

N-{2-[3-(4-Trifluoromethylphenylcarbonylamino)phenyl]-1-methylethyl}-N-propyl-[1-(morpholine-4-carbonyl)piperidin-4-ylmethyl]amine hydrochloride, M$^+$H 575;

N-{2-[3-(4-tert-Butylphenylcarbonylamino)phenyl]-1-methylethyl}-N-propyl-[1-(morpholine-4-carbonyl)piperidin-4-ylmethyl]amine hydrochloride, M$^+$H 563;

N-{2-[3-(4-Methanesulfonylphenylcarbonylamino)phenyl]-1-methylethyl}-N-propyl-[1-(morpholine-4-carbonyl)piperidin-4-ylmethyl]amine hydrochloride, M$^+$H 585;

N-{2-[3-(Cyclohexanecarbonylamino)phenyl]-1-methylethyl}-N-ethyl-[1-(morpholine-4-carbonyl)piperidin-4-ylmethyl]amine hydrochloride, M$^+$H 499;

N-{2-[3-(4-Methylphenylcarbonylamino)phenyl]-1-methylethyl}-N-ethyl-[1-(morpholine-4-carbonyl)piperidin-4-ylmethyl]amine hydrochloride, M$^+$H 507;

N-{2-[3-(4-Methoxyphenylcarbonylamino)phenyl]-1-methylethyl}-N-ethyl-[1-(morpholine-4-carbonyl)piperidin-4-ylmethyl]amine hydrochloride, M$^+$H 523;

N-{2-[3-(Furan-2-carbonylamino)phenyl]-1-methylethyl}-N-ethyl-[1-(morpholine-4-carbonyl)piperidin-4-ylmethyl]amine hydrochloride, M$^+$H 483;

(R)-N-{2-[3-(4-Methanesulfonylphenylcarbonylamino)phenyl]-1-methylethyl}-N-propyl-(1-methanesulfonylpiperidin-4-ylmethyl)amine hydrochloride, M$^+$H 550;

N-{2-[3-(Pyridine-3-carbonylamino)phenyl]-1-methylethyl}-N-propyl-[1-(morpholine-4-carbonyl)piperidin-4-ylmethyl]amine dichloride, M$^+$H 508;

N-{2-[3-(4-Trifluoromethoxyphenylcarbonylamino)phenyl]-1-methylethyl}-N-propyl-[1-(morpholine-4-carbonyl)piperidin-4-ylmethyl]amine hydrochloride, M$^+$H 591;

N-{2-[3-(4-Ethylphenylcarbonylamino)phenyl]-1-methylethyl}-N-propyl-[1-(morpholine-4-carbonyl)piperidin-4-ylmethyl]amine hydrochloride, M$^+$H 535;

N-{2-[3-(Biphenylcarbonylamino)phenyl]-1-methylethyl}-N-propyl-[1-(morpholine-4-carbonyl)piperidin-4-ylmethyl]amine hydrochloride, M$^+$H 583;

(R)-N-{2-[3-(4-tert-Butylphenylcarbonylamino)phenyl]-1-methylethyl}-N-propyl-(1-methanesulfonylpiperidin-4-ylmethyl)amine hydrochloride, M$^+$H 528;

(R)-N-{2-[3-(4-Trifluoromethylphenylcarbonylamino)phenyl]-1-methylethyl}-N-propyl-(1-methanesulfonylpiperidin-4-ylmethyl)amine hydrochloride, M$^+$H 540;

N-{2-[3-(4-Cyanophenylcarbonylamino)phenyl]-1-methylethyl}-N-propyl-[1-(morpholine-4-carbonyl)piperidin-4-ylmethyl]amine hydrochloride, M$^+$H 532;

N-{2-[3-(4-Propylphenylcarbonylamino)phenyl]-1-methylethyl}-N-propyl-[1-(morpholine-4-carbonyl)piperidin-4-ylmethyl]amine hydrochloride, M+H 549;

N-{2-[3-(4-Butylphenylcarbonylamino)phenyl]-1-methylethyl}-N-propyl-[1-(morpholine-4-carbonyl)piperidin-4-ylmethyl]amine hydrochloride, M+H 563;

(R)-N-{2-[3-(4-Cyanophenylcarbonylamino)phenyl]-1-methylethyl}-N-propyl-(1-methanesulfonylpiperidin-4-ylmethyl)amine hydrochloride, M+H 497;

N-{2-[3-(4-tert-Butylphenylcarbonylamino)phenyl]-1-methylethyl}-N-butyl-[1-(morpholine-4-carbonyl)piperidin-4-ylmethyl]amine hydrochloride, M+H 577;

N-{2-[3-(4-Methoxyphenylcarbonylamino)phenyl]-1-methylethyl}-N-butyl-[1-(morpholine-4-carbonyl)piperidin-4-ylmethyl]amine hydrochloride, M+H 551;

N-{2-[3-(Cyclohexanecarbonylamino)phenyl]-1-methylethyl}-N-butyl-[1-(morpholine-4-carbonyl)piperidin-4-ylmethyl]amine hydrochloride, M+H 527;

N-{2-[3-(Furan-2-carbonylamino)phenyl]-1-methylethyl}-N-butyl-[1-(morpholine-4-carbonyl)piperidin-4-ylmethyl]amine hydrochloride, M+H 511;

N-{2-[3-(Benzo[1,3]dioxole-5-carbonylamino)phenyl]-1-methylethyl}-N-butyl-[1-(morpholine-4-carbonyl)piperidin-4-ylmethyl]amine hydrochloride, M+H 565;

N-{2-[3-(4-Methoxyphenylcarbonylamino)phenyl]-1-methylethyl}-N-pentyl-[1-(morpholine-4-carbonyl)piperidin-4-ylmethyl]amine hydrochloride, M+H 565;

N-{2-[3-(Pyridine-4-carbonylamino)phenyl]-1-methylethyl}-N-propyl-[1-(morpholine-4-carbonyl)piperidin-4-ylmethyl]amine dichloride, M+H 508;

N-{2-[3-(Benzo[1,3]dioxole-5-carbonylamino)phenyl]-1-methylethyl}-N-allyl-[1-(morpholine-4-carbonyl)piperidin-4-ylmethyl]amine hydrochloride, M+H 549;

N-{2-[3-(4-Trifluoromethylphenylcarbonylamino)phenyl]-1-methylethyl}-N-propyl-[1-(isopropylaminocarbonyl)piperidin-4-ylmethyl]amine hydrochloride, M+H 547;

N-{2-[3-(4-Methoxycarbonylphenylcarbonylamino)phenyl]-1-methylethyl}-N-propyl-[1-(morpholine-4-carbonyl)piperidin-4-ylmethyl]amine, M+H 537;

N-{2-[3-(4-Hydroxycarbonylphenylcarbonylamino)phenyl]-1-methylethyl}-N-propyl-[1-(morpholine-4-carbonyl)piperidin-4-ylmethyl]amine, M+H 565;

N-{2-[3-(2,3-Benzo[1,3]dioxole-5-carbonylamino)phenyl]-1-methylethyl}-N-(1-ethylpropyl)-[1-(morpholine-4-carbonyl)piperidin-4-ylmethyl]amine hydrochloride, M+H 579;

N-{2-[3-(6-Oxo-1,4,5,6-tetrahydropyridazine-3-carbonylamino)phenyl]-1-methylethyl}-N-propyl-[1-(diethylaminocarbonyl)piperidin-4-ylmethyl]amine hydrochloride, M+H 513;

N-{2-[3-(4-Fluorophenylcarbonylamino)-4-methoxyphenyl]-1-methylethyl}-N-propyl-[1-(morpholine-4-carbonyl)piperidin-4-ylmethyl]amine hydrochloride, m.p. 96–102° C., M+H 555;

(R)-N-{2-[3-(4-Fluorophenylcarbonylamino)-4-methoxyphenyl]-1-methylethyl}-N-propyl-[1-(morpholine-4-carbonyl)piperidin-4-ylmethyl]amine hydrochloride, m.p. 86–92° C., M+H 555;

N-{2-[3-(4-Methanesulfonylphenylcarbonylamino)phenyl]-1-methylethyl}-N-isopropyl-[1-(morpholine-4-carbonyl)piperidin-4-ylmethyl]amine hydrochloride, M+H 585;

N-{2-[3-(2,3-Benzo[1,3]dioxole-5-carbonylamino)phenyl]-1-methylethyl}-N-(2,2,2-trifluoroethyl)-[1-(dimethylaminocarbonyl)piperidin-4-ylmethyl]amine isopropionate, M+H 535; and N-{2-[3-(2,3-Benzo[1,3]dioxole-5-carbonylamino)phenyl]-1-methylethyl}-N-propyl-[1-(methylaminocarbonyl)piperidin-4-ylmethyl]amine hydrochloride, M+H 495.

Example 11

Preparation of a Compounds of Formula Ik as Described in Scheme M Route (a)

11A. N-{2-[4-(Morpholine-4-carbonylamino)phenyl]-1-methylethyl]-N-propyl-(1-methanesulfonylpiperidin-4-ylmethyl)amine N-[2-(4-aminophenyl)-1-methylethyl]-N-propyl-(1-methanesulfonyl-piperidin-4-ylmethyl)amine (60 mg) was dissolved in ethyl acetate (1 ml) and saturated potassium carbonate (1 ml). The mixture was cooled in an ice bath to 0° C. and morpholine-4-carbonyl chloride (0.03 ml) was added. After stirring for 30 minutes, the layers were separated. The organic layer was dried over magnesium sulfate, filtered, and the solvent removed to give N-{2-[4-(morpholine-4-carbonylamino)phenyl]-1-methylethyl]-N-propyl-(1-methanesulfonylpiperidin-4-ylmethyl)amine (90 mg) as a foam, M+H 481.

Route (b)

11B. N-[2-(3-Isopropylureidophenyl)-1-methylethyl]-N-ethyl-(1-methanesulfonylpiperidin-4-ylmethyl)amine hydrochloride To a solution of N-[2-(3-aminophenyl)-1-methylethyl]-N-ethyl-(piperidine-4-ylmethyl)amine (0.2 g, 0.567 mmol) in dichloromethane (12 ml) was added isopropyl isocyanate (0.765 mmol). The reaction mixture was stirred at 22° C. for 15 hours. The solvent was removed under reduced pressure. The product was isolated as the hydrochloride salt from ethyl ether to give N-[2-(3-isopropylureidophenyl)-1-methylethyl]-N-ethyl-(1-methanesulfonylpiperidin-4-ylmethyl)amine hydrochloride (0.205 g, 76%), M+H 439.

Route (c)

11C. N-[2-(3-Carbamoylaminophenyl)-1-methylethyl]-N-propyl-(1-methanesulfonylpiperidin-4-ylmethyl)amine A solution of potassium cyanate (9 mg) in water (0.5 ml) was added to a solution of N-[2-(3-aminophenyl)-1-methylethyl]-N-propyl-(1-methanesulfonylpiperidin-4-ylmethyl)amine (40 mg) in water (2 ml) and acetic acid (1 ml). The mixture was stirred at ambient temperature for about 72 hours and then basified to pH 9 with 10% sodium hydroxide. The solution was extracted with dichloromethane, and the organic phase dried over sodium sulfate, filtered, evaporated in vacuo to give N-[2-(3-carbamoylaminophenyl)-1-methylethyl]-N-propyl-(1-methanesulfonylpiperidin-4-ylmethyl)amine (35 mg), M+H 411.2

11D. Similarly, substituting N-[2-(3-aminophenyl)-1-methylethyl)-N-ethyl-(piperidin-4-ylmethyl)amine with other amines, and substituting isopropyl isocyanate with other isocyanates and following the procedures described above in Example 11B, the following compounds of Formula Ik were prepared:

N-{2-[3-(3-phenylureido)phenyl]-1-methylethyl}-N-propyl-[1-(morpholine-4-carbonyl)piperidin-4-ylmethyl]amine hydrochloride, M+H 559; and N-{2-[3-(3-phenylureido)phenyl]-1-methylethyl]-N-propyl-(1-methanesulfonylpiperidin-4-ylmethyl)amine hydrochloride, M+H 487.

Example 12

Preparation of a Compounds of Formula Il as Described in Scheme N

The following compounds of Formula Il were prepared in the same manner as compounds of Formula Ij, but substituting 2-furoyl chloride with a sulfonyl chloride, and following the procedures described above in Example 10A:

N-[2-(3-Methanesulfonylaminophenyl)-1-methylethyl]-N-propyl-[1-(morpholine-4-carbonyl)piperidin-4-ylmethyl]amine hydrochloride, $M^+H$ 481;

N-[2-(3-Methanesulfonylaminophenyl)-1-methylethyl]-N-propyl-(1-methanesulfonylpiperidin-4-ylmethyl)amine hydrochloride, $M^+H$ 445;

N-{2-[3-(4-Methylphenylsulfonylamino)phenyl]-1-methylethyl}-N-propyl-(1-methanesulfonylpiperidin-4-ylmethyl)amine, $M^+H$ 522;

N-[2-(4-Methanesulfonylaminophenyl)-1-methylethyl]-N-propyl-[1-(morpholine-4-carbonyl)piperidin-4-ylmethyl]amine hydrochloride, $M^+H$ 481;

N-{2-[4-(Methanesulfonylamino)phenyl]-1-methylethyl}-N-propyl-(1-methanesulfonylpiperidin-4-ylmethyl)amine hydrochloride, $M^+H$ 446; and N-{2-[3-(Benzenesulfonylamino)phenyl]-1-methylethyl}-N-propyl-[1-(morpholine-4-carbonyl)piperidin-4-ylmethyl)amine hydrochloride, $M^+H$ 543.

Example 13

Preparation of a Compounds of Formula Im as Described in Scheme O

N-{2-[3-(4-Dimethylaminosulfonylamino)phenyl]-1-methylethyl}-N-propyl-(1-methanesulfonylpiperidin-4-ylmethyl)amine N-[2-(4-Aminophenyl)-1-methylethyl]-N-propyl-(1-methanesulfonylpiperidin-4-ylmethyl)amine (50 mg) was dissolved in dichloromethane (2 ml) and pyridine (0.01 ml). The mixture was cooled in ice and dimethylsulfamoyl chloride (0.015 ml) was added. The mixture was kept at 5° C. for about 72 hours, and washed with saturated sodium bicarbonate. The organic layer was dried ($Na_2SO_4$), filtered and the solvent removed in vacuo to give N-{2-[3-(4-dimethylaminosulfonylamino)phenyl]-1-methylethyl}-N-propyl-(1-methanesulfonylpiperidin-4-ylmethyl)amine as an oil (19 mg), $M^+H$ 475.

Example 14

Preparation of a Compounds of Formula In as Described in Scheme P

N-[2-(4-Dimethylaminophenyl)-1-methylethyl]-N-propyl-[1-(morpholine-4-carbonyl)piperidin-4-ylmethyl]amine dihydrochloride A solution of N-[2-(4-aminophenyl)-1-methylethyl]-N-propyl-[1-(morpholine-4-carbonyl)piperidin-4-ylmethyl]amine (0.256 mmole) in formic acid (1.0 ml) and 37% formaldehyde (1.0 ml) was heated at 100° C. for 6 hours. The reaction mixture was brought to pH 10 with 3N sodium hydroxide solution and extracted with ethyl acetate (25 ml). The organic phase was dried over anhydrous sodium sulfate and concentrated under reduced pressure. The product was isolated as the hydrochloride salt from ethyl ether to give N-[2-(4-dimethylaminophenyl)-1-methylethyl]-N-propyl-[1-(morpholine-4-carbonyl)piperidin-4-ylmethyl]amine dihydrochloride (0.09 g, 77%), $M^+H$ 431.

Example 15

The following are representative pharmaceutical formulations containing a compound of Formula I.

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum k (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 0.2 g |
| sodium acetate buffer solution, 0.4M | 2.0 ml |
| HCl (1 N) or NaOH (1 N) | q.s. to suitable pH |
| water (distilled, sterile) | q.s. to 20 ml |

Topical Formulation

A topical formulation is prepared with the following ingredients:

| Ingredient | Amount, g |
| --- | --- |
| compound of this invention | 10 |
| Span 60 | 2 |
| TWEEN ® 60 | 2 |
| mineral oil | 5 |
| petrolatum | 10 |
| methyl paraben | 0.15 |
| propyl paraben | 0.05 |
| BHA (butylated hydroxy anisole) | 0.01 |
| water | q.s. to 100 |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
| --- | --- |
| compound of the invention | 500 mg |
| Witepsol ® H-15 | balance |

Nasal Spray Formulation

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–12 hours.

Example 16

Radioligand Binding Studies

The inhibitory activity of compounds of this invention in vitro was determined using a modification of the method described in Hegde, S. S. et al. *Br. J. Pharmacol.*, 1997, 120, 1409–1418.

Cell membranes from Chinese hamster ovary cells expressing the recombinant human muscarinic receptors ($m_1$–$m_5$) were employed. The assays were conducted with the radioligand [$^3$H]N-methyl scopolamine(0.4 nM, specific activity 84 Ci·mmol$^{-1}$) in a final volume of 0.25 ml Tris-Krebs buffer. Non-specific binding was defined with 1 $\mu$M atropine. Assays were performed using scintillation proximity assay technology. Competition-displacement curves were generated using 10 concentrations of test compounds and were analyzed by iterative curve fitting to a four parameter logistic equation. $pIC_{50}$ values (-log of the $IC_{50}$) were converted to pKi values using the Cheng-Prusoff equation.

Compounds of this invention were active in this assay.

Example 17

Anti-muscarinic Activity in Anesthetized Rats

The muscarinic receptor inhibitory activity of compounds of this invention in vivo was determined in rats using a modification of the method described in Hegde, S. S. et al. *Proceedings of the 26th Annual Meeting of the International Continence Society* (August 27th–30th) 1996, Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions and oxotremorine-induced saliva secretion was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a positive control. In a separate group of animals, the saliva secretory response to oxotremorine (0.1 mg/kg, iv) over a 10-minute period was determined after the animals were intravenously dosed with a single dose of the test compound. Saliva output was determined by placing pre-weighed cotton pads in the animals mouth and re-weighing these pads at 10-minute post-oxotremorine.

Compounds of this invention were active in this assay.

Example 18

Anti-muscarinic Activity in Anesthetized Dogs

The muscarinic receptor inhibitory activity of compounds of this invention in vivo was determined in dogs using a modification of the method described in Newgreen, D. T. et al. *J. Urol.*, 1996, 155 (Suppl. 5), 1156.

Female dogs were anesthetized with pentobarbital and instrumented for measurement of arterial pressure, heart rate and pelvic-nerve mediated bladder contractions and chorda-lingual nerve mediated saliva secretion. The pelvic and chorda-lingual nerves were stimulated for 20 seconds and 2 minutes, respectively, with a minimum of 10 minute interval between each set of stimulations . After two consistent control responses were obtained, the test compound was dosed in a cumulative fashion, 3 minutes prior to each stimulation of the pelvic and chorda-lingual nerves. Atropine (1.0 mg/kg, iv) was given as a positive control at the end of the study.

Compounds of this invention were active in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound selected from the group of compounds represented by Formula I:

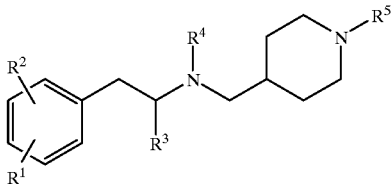

wherein:
R$^1$ is independently in each occurrence:
hydrogen, alkyl, alkyloxy, halogen, haloalkyl, or amino;
R$^2$ is independently in each occurrence:
(1) alkyl,
(2) alkyloxy,
(3) halogen,
(4) haloalkyl,
(5) nitro,
(6) heterocyclyl, unsubstituted or heterocyclyl optionally substituted with oxo,
(7) —O(CH$_2$)$_p$X wherein p is 0–6 and X is independently selected from haloalkyl or aryl,
(8) —NR$^7$R$^8$,
(9) —NR$^6$COR$^9$,
(10) —NR$^6$CONR$^7$R$^8$,
(11) —NR$^6$CSR$^9$,
(12) —NR$^6$CSNR$^7$R$^8$,
(13) —NR$^6$SO$_2$R$^9$,
(14) —NR$^6$SO$_2$NR$^7$R$^8$,
(15) —SR$^9$,
(16) —SOR$^9$,
(17) —SO$_2$R$^9$,
(18) —SO$_2$NR$^7$R$^8$; or R$^1$ and R$^2$ taken together with the ring to which they are attached form a 5- or 6-membered monocyclic saturated or unsaturated ring optionally containing 0, 1 or 2 heteroatoms independently selected from nitrogen, oxygen or sulfur;

R$^3$ and R$^4$ are independently in each occurrence:
lower alkyl, alkenyl, or cycloalkyl;

R$^5$ is independently in each occurrence:
(1) hydrogen,
(2) —COR$^9$,
(3) —COOR$^7$,
(4) —CONR$^7$R$^8$,
(5) —CO(CH$_2$)$_n$COR$^9$,
(6) —CO(CH$_2$)$_n$SO$_2$R$^9$,
(7) —CO(CH$_2$)$_n$CONR$^7$R$^8$,
(8) —CO(CH$_2$)$_n$SO$_2$NR$^7$R$^8$,
(9) —CO(CH$_2$)$_n$NR$^6$COR$^9$,
(10) —CO(CH$_2$)$_n$NR$^6$SO$_2$R$^9$,
(11) —CO(CH$_2$)$_n$NR$^6$CONR$^7$R$^8$,
(12) —CO(CH$_2$)$_n$NR$^6$SO$_2$NR$^7$R$^8$,
(13) —CSR$^9$,
(14) —CSNR$^7$R$^8$,
(15) —SO$_2$R$^9$,
(16) —SO$_2$NR$^7$R$^8$,
(17) —SO$_2$(CH$_2$)$_n$NR$^6$SO$_2$R$^9$, or
(18) —SO$_2$NR$^6$(CH$_2$)$_n$COOR$^7$;
wherein
n is 1–6;

R$^6$ and R$^7$ are independently in each occurrence:
hydrogen or lower alkyl;

R$^8$ is independently in each occurrence:
hydrogen, lower alkyl, cycloalkyl, aryl, or heteroaryl;
R$^9$ is independently in each occurrence:
(1) alkyl,
(2) cycloalkyl,
(3) arylalkyl,
(4) aryl, unsubstituted or mono-, di-, or tri-substituted aryl, the substituents being independently selected from lower alkyl, alkyloxy, halogen, hydroxyalkyl, haloalkyl, cyano, nitro, —CONR$^7$R$^8$, —COR$^7$, —COOR$^7$, —NR$^7$R$^8$, —NCOR$^9$, —SO$_2$R$^9$, —SO$_2$NR$^7$R$^8$, or —O(CH$_2$)$_p$X wherein p is 0–6 and X is haloalkyl or aryl,
(5) heterocyclyl, unsubstituted or mono- or di-substituted heterocyclyl, the substitutents independently selected from lower alkyl, hydroxy, hydroxyalkyl, oxo, —COR$^7$, or —COOR$^7$, or
(6) heteroaryl, unsubstituted or mono-, di-, or tri-substituted heteroaryl, the substituents being independently selected from lower alkyl, alkyloxy, halogen, hydroxyalkyl, haloalkyl, cyano, nitro, —CONR$^7$R$^8$, —COR$^7$, —COOR$^7$, —NR$^7$R$^8$, —NCOR$^9$, —SO$_2$R$^9$, —SO$_2$NR$^7$R$^8$, or —O(CH$_2$)$_p$X wherein p is 0–6 and X is haloalkyl or aryl;

as an individual isomer or as a racemic or non-racemic mixture of isomers, or a pharmaceutically acceptable salt thereof.

2. The compound of claim 1 wherein R$^3$ and R$^4$ are independently in each occurrence lower alkyl or cycloalkyl.

3. The compound of claim 2 wherein R$^3$ and R$^4$ are independently in each occurrence methyl, ethyl, propyl, isopropyl or cyclopropylmethyl.

4. The compound of claim 3 wherein R$^3$ is methyl, and R$^4$ is independently in each occurrence ethyl, propyl, isopropyl or cyclopropylmethyl.

5. The compound of claim 4 wherein R$^5$ is —SO$_2$R$^9$, —COR$^9$, —CONR$^7$R$^8$ or —CO(CH$_2$)$_n$NR$^6$SO$_2$R$^9$.

6. The compound of claim 5 wherein R$^5$ is —SO$_2$R$^9$.

7. The compound of claim 6 wherein R$^9$ is alkyl.

8. The compound of claim 7 wherein R$^9$ is methyl, ethyl, or propyl.

9. The compound of claim 5 wherein R$^5$ is —COR$^9$.

10. The compound of claim 9 wherein R$^9$ is heterocyclyl or heteroaryl.

11. The compound of claim 10 wherein R$^9$ is morpholino, piperidinyl, or 1,2,3,4-tetrahydro[1,5]naphthyridinyl.

12. The compound of claim 5 wherein R$^5$ is —CONR$^7$R$^8$.

13. The compound of claim 12 wherein R$^7$ and R$^8$ are independently in each occurrence lower alkyl.

14. The compound of claim 13 wherein R$^7$ and R$^8$ are independently in each occurrence methyl, ethyl, or propyl.

15. The compound of claim 5 wherein R$^5$ is —CO(CH$_2$)$_n$NR$^6$SO$_2$R$^9$.

16. The compound of claim 15 wherein n is 1–4, R$^6$ is hydrogen, and R$^9$ is alkyl.

17. The compound of claim 16 wherein R$^9$ is methyl, ethyl, or propyl.

18. The compound of claim 8 wherein R$^1$ and R$^2$ taken together with the ring to which they are attached form a 5- or 6-membered monocyclic saturated or unsaturated ring optionally containing 0, 1 or 2 heteroatoms independently selected from nitrogen, oxygen or sulfur, and in which the ring is unsubstituted or optionally mono-or di-substituted with lower alkyl or oxo.

19. The compound of claim 18 wherein R$^1$ and R$^2$ taken together with the ring to which they are attached form a 5- or 6-membered monocyclic saturated ring optionally containing 0, 1, or 2 oxygen heteroatoms, and in which the ring is unsubstituted or optionally mono- or di-substituted with lower alkyl or oxo.

20. The compound of claim 19 wherein $R^1$ and $R^2$ taken together with the ring to which they are attached form indanyl, 2,3-dihydrobenzofuran-5-yl, 2,3-dihydrobenzofuran-6-yl, 3,3-dimethyl-2,3,dihydrofuran-5-yl, 3,3-dimethyl-2,3,dihydrofuran-6-yl, or 2,3-dihydrobenzo[1,4]dioxin-6-yl.

21. The compound of claim 20 wherein $R^1$ and $R^2$ taken together with the ring to which they are attached form 2,3-dihydrobenzofuranyl; $R^3$ is methyl; $R^4$ is ethyl; and $R^9$ is methyl.

22. The compound of claim 5 wherein $R^1$ is hydrogen; and $R^2$ is alkyloxy, halogen, or haloalkyl.

23. The compound of claim 22 wherein $R^2$ is methoxy, ethoxy, propoxy, chloro, bromo, or trifluoromethyl.

24. The compound of claim 5 wherein $R^1$ is hydrogen; and $R^2$ is —$NR^7COR^9$.

25. The compound of claim 24 wherein $R^7$ is hydrogen, $R^9$ is aryl, unsubstituted or mono-, di-, or tri-substituted aryl, the substituents being selected from lower alkyl, alkyloxy, halogen, or haloalkyl.

26. The compound of claim 25 wherein $R^9$ is phenyl, unsubstituted or mono-, di-, or tri-substituted phenyl, the substituents being selected from methyl, ethyl, methoxy, ethoxy, chloro, or trifluoromethyl.

27. A compound of Formula I selected from:

N-[2-(2,3,-Dihydrobenzofuran-5-yl)-1-methylethyl]-N-ethyl-(1-methanesulfonylpiperidin-4-ylmethyl)amine;

N-[2-(2,3-Dihydrobenzofuran-5-yl)-1-methylethyl]-N-propyl-(1-methanesulfonylpiperidin-4-ylmethyl)amine;

N-[2-(2,3-Dihydrobenzofuran-6-yl)-1-methylethyl]-N-propyl-[1-(morpholine-4-carbonyl)piperidin-4-ylmethyl]amine;

N-[2-(2,3-Dihydrobenzofuran-6-yl)-1-methylethyl]-N-cyclopropylmethyl-[1-(morpholine-4-carbonyl)piperidin-4-ylmethyl)amine;

N-[2-(2,3-Dihydrobenzofuran-5-yl)-1-methylethyl]-N-ethyl-[1-(morpholine-4-carbonyl)piperidin-4-ylmethyl]amine;

N-[2-(2,3-Dihydrobenzofuran-5-yl)-1-methylethyl]-N-propyl-[1-(morpholine-4-carbonyl)piperidin-4-ylmethyl]amine;

N-[2-(2,3-Dihydrobenzo[1,4]dioxin-6-yl)-1-methylethyl]-N-ethyl-[1-(morpholine-4-carbonyl)piperidin-4-ylmethyl]amine;

(S)-N-{3-[4-({[2-(2,3-Dihydrobenzofuran-5-yl)-1-methylethyl]ethylamino}methyl)piperidin-1-yl]-3-oxopropyl}-methanesulfonamide;

N-[2-(Indan-5-yl)-1-methylethyl]-N-ethyl-(1-methanesulfonylpiperidin-4-ylmethyl)amine;

N-[2-(Indan-5-yl)-1-methylethyl]-N-propyl-(1-methanesulfonylpiperidin-4-ylmethyl)amine;

N-[2-(3,3-Dimethyl-2,3-dihydrobenzofuran-6-yl)-1-methylethyl]-N-ethyl-[1-(morpholine-4-carbonyl)piperidin-4-ylmethyl]amine;

N-[2-(3,3-Dimethyl-2,3,-dihydrobenzofuran-6-yl)-1-methylethyl]-N-ethyl-(1-methanesulfonylpiperidin-4-ylmethyl)amine;

N-[2-(4-Methoxyphenyl)-1-methylethyl]-N-ethyl-[1-(dimethylaminocarbonyl)piperidin-4-ylmethyl]amine;

N-[2-(3-Trifluoromethylphenyl)-1-methylethyl]-N-ethyl-[1-(dimethylaminocarbonyl)piperidin-4-ylmethyl]amine;

N-[2-(3-Trifluoromethylphenyl)-1-methylethyl]-N-ethyl-[1-(piperidine-1-carbonyl)piperidin-4-ylmethyl]amine;

N-[2-(4-Trifluoromethylphenyl)-1-methylethyl]-N-ethyl-[1-(piperidine-1-carbonyl)piperidin-4-ylmethyl]amine;

N-[2-(4-Trifluoromethylphenyl)-1-methylethyl]-N-ethyl-[1-(dimethylaminocarbonyl)piperidin-4-ylmethyl]amine;

N-[2-(3-Trifluoromethylphenyl)-1-methylethyl]-N-ethyl-[1-(morpholine-4-carbonyl)piperidin-4-ylmethyl]amine;

N-[2-(3-Trifluoromethylphenyl)-1-methylethyl]-N-ethyl-[1-(1,2,3,4-tetrahydro[1,5]naphthyridine-1-carbonyl)piperidin-4-ylmethyl]amine;

N-[2-(3-Chlorophenyl)-1-methylethyl]-N-ethyl-[1-(piperidine-1-carbonyl)piperidin-4-ylmethyl]amine;

N-[2-(3-Trifluoromethylphenyl)-1-methylethyl]-N-propyl-[1-(morpholine-4-carbonyl)piperidin-4-ylmethyl]amine;

N-{2-[3-(4-Methoxyphenylcarbonylamino)phenyl]-1-methylethyl}-N-propyl-[1-(morpholine-4-carbonyl)piperidin-4-ylmethyl]amine; or N-{2-[3-(4-Methylphenylcarbonylamino)-phenyl]-1-methylethyl}-N-propyl-[1-(morpholine-4-carbonyl)piperidin-4-ylmethyl]amine.

28. The compound of claim 1 or 27 wherein the pharmaceutically acceptable salt is a salt formed from hydrochloric acid, phosphoric acid, trifluoroacetic acid, or dibenzoyl-L-tartaric acid.

29. The pharmaceutical composition comprising a therapeutically effective amount of a compound of claim 1 or 27, in admixture with at least one pharmaceutically acceptable non-toxic carrier.

30. The method for treating a condition which can be ameliorated by a drug which blocks muscarinic receptors in a mammal in need of such treatment, which method comprises administering to such a mammal a therapeutically effective amount of a compound of claim 1 or 27.

31. The method of claim 30 wherein the condition is independently selected from gastrointestinal tract disorder, genitourinary tract disorder, or respiratory tract disorder.

32. The method of claim 31 wherein the condition is gastrointestinal tract disorder.

33. The method of claim 32 wherein the condition is selected from irritable bowel syndrome, diverticular disease, achalasia, gastrointestinal hypermotility disorder, or diarrhea.

34. The method of claim 31 wherein the condition is genitourinary tract disorder.

35. The method of claim 34 wherein the wherein the condition is selected from overactive bladder or stress incontinence.

* * * * *